US011104955B2

United States Patent
Greene et al.

(10) Patent No.: US 11,104,955 B2
(45) Date of Patent: Aug. 31, 2021

(54) MAP2K1 (MEK1) AS A THERAPEUTIC TARGET FOR ARTERIOVENOUS MALFORMATIONS AND ASSOCIATED DISORDERS

(71) Applicant: Children's Medical Center Corporation, Boston, MA (US)

(72) Inventors: Arin K. Greene, Wellesley, MA (US); Matthew Warman, Boston, MA (US); Yue Huang, Brookline, MA (US)

(73) Assignee: CHILDREN'S MEDICAL CENTER CORPORATION, Boston, MA (US)

( * ) Notice: Subject to any disclaimer, the term of this patent is extended or adjusted under 35 U.S.C. 154(b) by 0 days.

(21) Appl. No.: 16/474,976

(22) PCT Filed: Dec. 29, 2017

(86) PCT No.: PCT/US2017/069052
§ 371 (c)(1),
(2) Date: Jun. 28, 2019

(87) PCT Pub. No.: WO2018/126192
PCT Pub. Date: Jul. 5, 2018

(65) Prior Publication Data
US 2020/0024666 A1     Jan. 23, 2020

Related U.S. Application Data

(60) Provisional application No. 62/441,004, filed on Dec. 30, 2016.

(51) Int. Cl.
| *C12Q 1/6883* | (2018.01) |
| *A61P 9/00* | (2006.01) |
| *A61K 31/4523* | (2006.01) |
| *A61K 31/519* | (2006.01) |
| *A61K 45/06* | (2006.01) |
| *A61K 9/00* | (2006.01) |

(52) U.S. Cl.
CPC .......... *C12Q 1/6883* (2013.01); *A61K 9/0019* (2013.01); *A61K 31/4523* (2013.01); *A61K 31/519* (2013.01); *A61K 45/06* (2013.01); *A61P 9/00* (2018.01); *C12Q 2600/112* (2013.01); *C12Q 2600/156* (2013.01)

(58) Field of Classification Search
CPC ............ A61K 31/4184; A61K 31/4523; A61K 31/519; A61K 31/7052; A61K 45/06; A61P 9/00
See application file for complete search history.

(56) References Cited

U.S. PATENT DOCUMENTS

| 2006/0141472 A1 | 6/2006 | Vikkula et al. |
| 2012/0245180 A1 | 9/2012 | Auger et al. |
| 2013/0324548 A1 | 12/2013 | Denys et al. |
| 2014/0050665 A1 | 2/2014 | Henske et al. |
| 2016/0158194 A1* | 6/2016 | Silva .................... A61K 31/404 514/460 |
| 2016/0229836 A1 | 8/2016 | Stockwell et al. |
| 2019/0358230 A1* | 11/2019 | Gmachl ............... A61K 31/337 |

FOREIGN PATENT DOCUMENTS

WO     2016/187157 A1     11/2016

OTHER PUBLICATIONS

Gilmartin et al., "GSK1120212 (JTP-74057) Is an Inhibitor of MEK Activity and Activation with Favorable Pharmacokinetic Properties for Sustained In Vivo Pathway Inhibition", 2011, Clin. Cancer Res., 17(5), pp. 989-1000. (Year: 2011).*
Coldwell et al., "From the RSNA Refresher Courses; Embolotherapy: Agents, Clinical Applications, and Techniques", 1994, RadioGraphics, 14(3), pp. 623-643. (Year: 1994).*
Couto et al., "Somatic MAP2K1 Mutations Are Associated with Extracranial Arteriovenous Malformation", 2017, The American Journal of Human Genetics, 100(3), pp. 546-554. (Year: 2017).*
Smits et al., "Endothelial MAP2K1 mutations in arteriovenous malformation activate the RAS/MAPK pathway", 2020, Biochemical and Biophysical Research Communications, 529(2), pp. 450-454. (Year: 2020).*
Prior et al. A Comprehensive Survey of Ras Mutations in Cancer. Cancer Res (May 15, 2012) vol. 72, No. 10, pp. 2457767, Fig. 1, Table 2.
Arcila et al. MAP2K1 (MEK1) Mutations Define a Distinct Subset of Lung Adenocarcinoma Associated with Smoking. Clin Cancer Res (Apr. 15, 2015) vol. 21, No. 8, pp. 1935-1943, Fig. 1.

* cited by examiner

*Primary Examiner* — My-Chau T. Tran
(74) *Attorney, Agent, or Firm* — Nixon Peabody LLP; David S. Resnick

(57) ABSTRACT

The instant disclosure provides methods and compositions related to discovery of MAP2K (MEK1) as a therapeutic target for treatment or prevention of arteriovenous malformations (AVMs). Therapeutic and/or prophylactic uses and compositions of known MEK1 inhibitors, including small molecules and nucleic acid agents, are described.

13 Claims, 22 Drawing Sheets
Specification includes a Sequence Listing.

- CD31+Day6
- CD31+Day8
- CD31-Day4
- CD31-Day1

*PCA of cultured CD31$^+$ versus CD31$^-$ cells*

*violin plots*

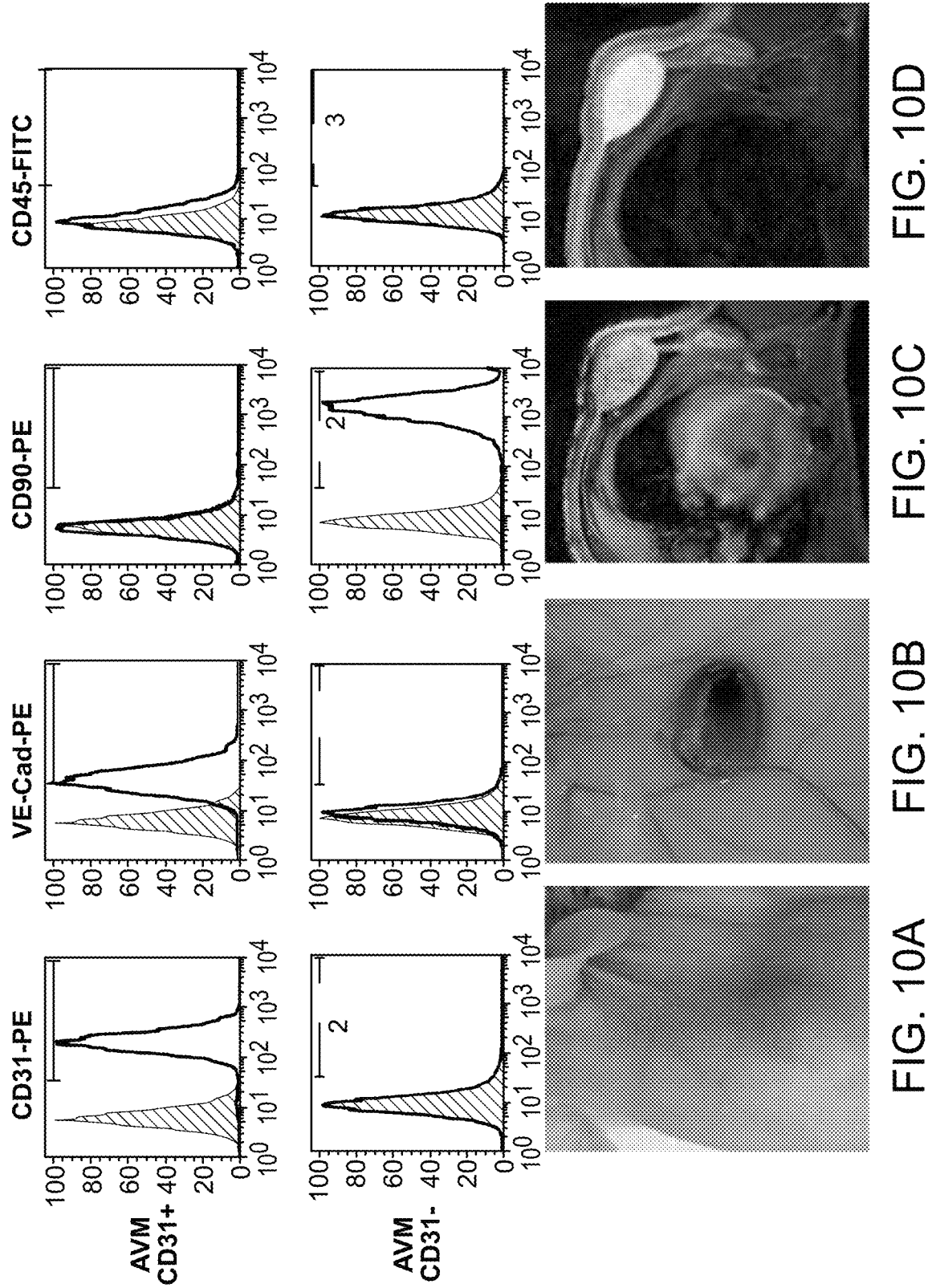

FIG. 11A
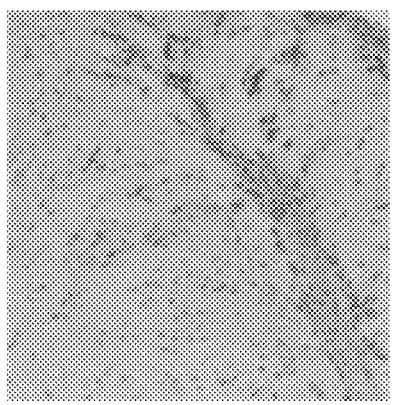
AVM CD31+
AVM CD31-
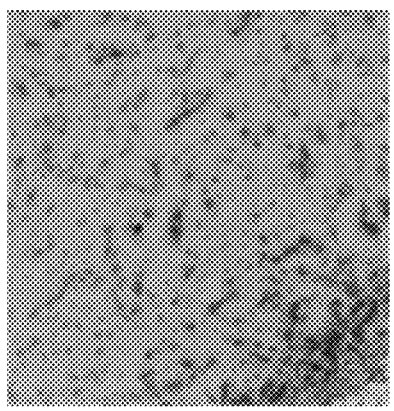
Control ECFC
AVM CD31-
FIG. 11B
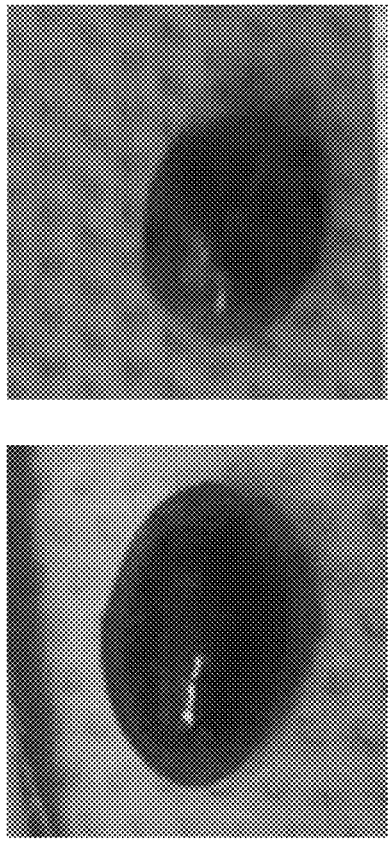
AVM CD31+
AVM CD31-
Control ECFC
AVM CD31-
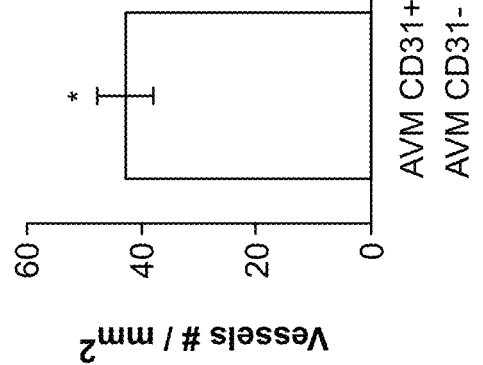
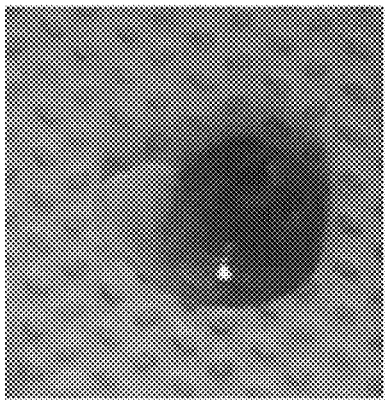
AVM CD31+
Control MSC
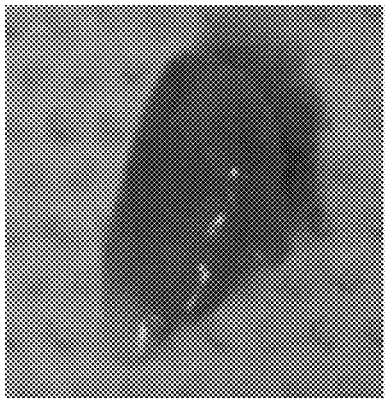
Control ECFC
Control MSC

MAP2K1 (MEK1) AS A THERAPEUTIC TARGET FOR ARTERIOVENOUS MALFORMATIONS AND ASSOCIATED DISORDERS

RELATED APPLICATIONS

This application is a 35 USC § 371 U.S. national stage application of International Application No. PCT/US17/69052 filed Dec. 29, 2017, which claims the benefit under 35 USC § 119(e) to U.S. Application Ser. No. 62/441,004 filed Dec. 30, 2016. The entire contents of these applications are incorporated herein by reference in their entirety.

STATEMENT REGARDING FEDERALLY SPONSORED RESEARCH OR DEVELOPMENT

This invention was made with government support under Grant nos. HD082606, HD081004 and AR064231, awarded by The National Institutes of Health. The government has certain rights in the invention.

SEQUENCE LISTING

This instant application contains a Sequence Listing which has been submitted electronically in ASCII format and is hereby incorporated by reference in its entirety. Said ASCII copy, created Jun. 27, 2019 is named 048218-553N01US_SL.txt and is 12,288 bytes.

BACKGROUND

Arteriovenous malformation (AVM) is a fast-flow, congenital vascular anomaly that may arise anywhere in the body. AVMs typically progress, causing destruction of surrounding tissue and, sometimes, cardiac overload. Sporadic extracranial AVMs are solitary and may be localized or regional. Rapid blood flow is demonstrable by Doppler ultrasonography. Magnetic resonance imaging reveals enhancement following contrast administration and signal voids consistent with fast-flow, while angiography shows the early filling of draining veins (FIG. 1). With time, arterial to venous shunting causes tissue ischemia that leads to pain, ulceration, bleeding, and destruction of adjacent tissues. AVMs are difficult to control; they often re-expand after embolization or resection, and pharmacologic therapy has, to date, been unavailable[2]. Embolization and/or resection are often followed by expansion. Therefore, there is a need in the field for the identification of therapeutics that ameliorate and/or prevent AVM.

SUMMARY

The instant disclosure is based, at least in part, upon the identification of MAP2K1 upregulatory mutations as the likely genetic basis for sporadic, extracranial AVM. Such identification has thereby inspired a new strategy for treatment or prevention of AVM in a subject—specifically, one based upon administration of a MAP2K1 (MEK1) inhibitor to the subject.

Targeting of MAP2K1 (MEK1) with one or more antagonists, including known antagonists such as trametinib, cobimetinib, binimetinib, selumetinib, antisense and/or RNAi agents, for treatment or prevention of AVM and/or an associated disease or disorder is specifically contemplated.

In one aspect, the instant disclosure provides a method for treating or preventing arteriovenous malformation (AVM) in a subject, the method involving identifying a subject having or at risk of AVM; and administering a MEK1 inhibitor to the subject, thereby treating or preventing AVM in the subject.

In one embodiment, the MEK1 inhibitor is a small molecule antagonist or an inhibitory nucleic acid.

In certain embodiments, the MEK1 inhibitor is trametinib, cobimetinib, binimetinib, selumetinib, or any combination thereof.

In some embodiments, an anti-angiogenic agent is administered to the subject, comprising sunitinib, angiostatin K1-3, arresten, DL-α-difluoromethyl-ornithine, fumagillin, genistein, staurosporine, (±)-thalidomide, tumstatin, axitinib, bortezomib, bosutinib gefitinib, pazopanib, semaxanib, sorafenib, vandetanib, vatalanib, canertinib, cilengitide, dovitinib, dasatinib, erlotinib, everolimus, imatinib, lapatinib, masutinib, marizomib, mubitinib, lestaurtinib, pazopanib, tandutinib, vismodegib or combinations thereof.

In some embodiments, an effective amount of one or more inhibitors of ERK1/2 are administered to the subject, comprising SCH772984, LY3214996, SC1, RasGAP, VX-11e, DEL-22379, Ulixertinib (BVD-523, VRT752271), GDC-0994, FR 180204, ERK5-IN-1, or combinations thereof.

In some embodiments, the AVM possesses a somatic MAP2K1 mutation, optionally a MAP2K1 mutation that upregulates MEK1 levels. In some embodiments, AVM possesses a mutation in one or more genes associated with the RAS/MAPK pathway, comprising: HRAS, KRAS, NRAS, ARAF, BRAF, RAF1, MAP2K2, MAPK1, MAPK3, MAP3K3. In certain embodiments, mutations in genes that cause lesions resembling AVM comprise RASA, PTEN, ENG, ACVRL1, SMAD4, GDF2 or combinations thereof.

In some embodiments, the AVM possesses a somatic MAP2K1 mutation and/or in one or more genes associated with a RAS/MAPK pathway. In some embodiments, the one or more genes associated with the RAS/MAPK pathway, comprise: HRAS, KRAS, NRAS, ARAF, BRAF, RAF1, MAP2K2, MAPK1, MAPK3, MAP3K3, or combinations thereof. In some embodiments the mutation in HRAS is p.Thr58_Ala59delinsValLeuAspVal and the somatic MAP2K1 mutation comprises: Lys57Asn (n=8), Gln56Pro (n=4), Gln58_Glu62 del (n=2), Phe53Leu/Asp67Tyr, or combinations thereof. In some embodiments, the somatic MAP2K1 mutations comprise p.F53L and p.D67Y in cis.

In certain embodiments, the AVM possesses one or more somatic MAP2K1 mutations recited in Table 2. Optionally, the AVM possesses somatic MAP2K1 mutations p.F53L and p.D67Y in cis.

The AVM can be in any location of the subject's body. In one embodiment, the AVM is an extracranial AVM. In certain embodiments, the AVM comprises a brain AVM, a spinal cord AVM, a facial AVM, a scalp AVM, an ear AVM, an upper lip AVM, an abdominal AVM, a limb AVM or any combinations thereof.

In certain embodiments, the AVM is a Stage I AVM.

In other embodiments, the AVM is a Stage II or Stage III AVM.

Optionally, the subject is a human.

In certain embodiments, the AVM location is one that is recited in Table 2.

In one embodiment, the MEK1 inhibitor is administered orally or by injection.

In some embodiments, the subject is human.

In another embodiment, the AVM is embolized or resected, and optionally no further expansion of the AVM occurs post-embolization and/or post-resection.

In an additional aspect, the instant disclosure provides a pharmaceutical composition for treating or preventing an AVM in a subject, the pharmaceutical composition including a MEK1 inhibitor and a pharmaceutically acceptable carrier or excipient.

DEFINITIONS

Unless defined otherwise, all technical and scientific terms used herein have the meaning commonly understood by a person skilled in the art to which the instant disclosure belongs. The following references provide one of skill with a general definition of many of the terms used in this disclosure: The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

An 'agent' is meant any small compound, antibody, nucleic acid molecule, or peptide or fragment thereof. An "agent" includes a "therapeutic agent" as defined herein below.

By "ameliorate" is meant decrease, suppress, attenuate, diminish, arrest, or stabilize the development or progression of a disease.

An "agonist" as used herein is a molecule which enhances the biological function of a protein. The agonist may thereby bind to the target protein to elicit its functions. However, agonists which do not bind the protein are also envisioned. The agonist may enhance the biological function of the protein directly or indirectly. Agonists which increase expression of certain genes are envisioned within the scope of particular embodiments of the instant disclosure. Suitable agonists will be evident to those of skill in the art. For the present disclosure it is not necessary that the agonist enhances the function of the target protein directly. Rather, agonists are also envisioned which stabilize or enhance the function of one or more proteins upstream in a pathway that eventually leads to activation of targeted protein. Alternatively, the agonist may inhibit the function of a negative transcriptional regulator of the target protein, wherein the transcriptional regulator acts upstream in a pathway that eventually represses transcription of the target protein.

An "antagonist" may refer to a molecule that interferes with the activity or binding of another molecule, for example, by competing for the one or more binding sites of an agonist, but does not induce an active response.

By "vascular anomaly" is meant a localized defect in blood vessels that can affect each part of the vasculature (capillaries, arteries, veins, lymphatics or a combination of these). Such defects are often characterized by an increased number of vessels and vessels that are both enlarged and sinuous. Some vascular anomalies are congenital and therefore present at birth, others appear within weeks to years after birth and others are acquired by trauma or during pregnancy. Inherited vascular anomalies have been described and are often present with a number of lesions that increase with patients' age. Vascular anomalies can also be a part of a syndrome and, occasionally, they can be acquired by trauma. Common forms of vascular anomaly include hemangioma, kaposiform hamangioendothelioma, pyogenic granuloma, capillary malformation, lymphatic malformation, venous malformation and arteriovenous malformation.

By "arteriovenous malformation" or "AVM" is meant an abnormal connection between arteries and veins, bypassing the capillary system. Such forms of vascular anomaly often occur in the central nervous system (usually cerebral AVM), but can also appear in any location. Although many AVMs are asymptomatic, they can cause intense pain or bleeding or lead to other serious medical problems.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Any compositions or methods provided herein can be combined with one or more of any of the other compositions and methods provided herein.

By "effective amount" is meant the amount of an agent required to ameliorate the symptoms of a disease relative to an untreated patient. The effective amount of active agent(s) used to practice the present disclosure for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "inhibitory nucleic acid" is meant a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Chitosan compositions are useful for the delivery of polynucleotides, such as inhibitory nucleic acid molecules, useful for the treatment or prevention of pathogen infection and related disease. Typically, a nucleic acid inhibitor comprises at least a portion of a target nucleic acid molecule, or an ortholog thereof, or comprises at least a portion of the complementary strand of a target nucleic acid molecule. For example, an inhibitory nucleic acid molecule comprises at least a portion of any or all of the nucleic acids delineated herein.

As used herein, "obtaining" as in "obtaining an agent" includes synthesizing, purchasing, or otherwise acquiring the agent.

Unless specifically stated or obvious from context, as used herein, the term "or" is understood to be inclusive. Unless specifically stated or obvious from context, as used herein, the terms "a", "an", and "the" are understood to be singular or plural.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

By "reference" is meant a standard or control, e.g., a standard or control condition.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

By "reduces" is meant a negative alteration of at least 10%, 25%, 50%, 75%, or 100%.

By "siRNA" is meant a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal; for example, they may be introduced systemically via the bloodstream. Such siRNAs are used to downregulate mRNA levels or promoter activity.

By "subject" is meant a mammal, including, but not limited to, a human or non-human mammal, such as a bovine, equine, canine, ovine, or feline.

A "therapeutically effective amount" is an amount sufficient to effect beneficial or desired results, including clinical results. An effective amount can be administered in one or more administrations.

As used herein, the terms "treat," "treating," "treatment," and the like refer to reducing or ameliorating a disorder and/or symptoms (e.g., AVM or other AVM-associated disease or disorder) associated therewith. It will be appreciated that, although not precluded, treating a disorder or condition does not require that the disorder, condition or symptoms associated therewith be completely eliminated.

Any compositions or methods provided herein can be combined with one or more of any of the other compositions and methods provided herein.

Other features and advantages of the instant disclosure will be apparent to those skilled in the art from the following detailed description and claims.

BRIEF DESCRIPTION OF THE DRAWINGS

FIGS. 1A to 1E show solitary extracranial AVMs. FIG. 1A shows a photograph of participant 23 during childhood (stage I) and FIG. 1B shows participant 23 during adulthood (stage III). Progressive growth of the facial AVM was seen. FIG. 1C shows coronal magnetic resonance image illustrating the extent of the lesion with multiple signal voids consistent with fast-flow (white arrows). FIG. 1D displays an angiogram showing tortuous arteries (white arrows) that feed the AVM, the "nidus" (dotted oval) where there are direct communications between numerous small arteries and veins, and early filling of draining veins (black arrows). FIG. 1E shows a hematoxylin and eosin stained section of participant 23's affected tissue, obtained following initial resection. The large feeder artery (asterisk), hyper-muscularized veins (arrows), and an area where arteries and veins connect in the absence of a normal capillary bed (dotted oval) were observed. FIGS. 1F to 1I show photographs of other AVMs that contain somatic MAP2K1 mutations. FIG. 1F shows participant 2, possessing a scalp AVM (stage III); FIG. 1G shows participant 6, possessing an ear AVM (stage I); FIG. 1H shows participant 12, possessing an upper lip AVM (stage I); and FIG. 1I shows participant 19, possessing an abdominal AVM (stage II).

FIG. 2A displays a graph depicting the depth-of-coverage across the exome for 10 affected tissue samples and 3 unaffected tissue samples. Note 90-fold coverage for 90% of the exome obtained for each AVM sample. FIG. 2B displays Integrative Genomic Viewer screenshots showing reads containing variant and reference alleles for 4 AVM samples. Total read depth at the site of the somatic mutation is indicated as "-fold" coverage. Note 4 reads in participant 19 indicated that the p.F53L and p.D67Y somatic mutations were in cis. FIG. 2C displays a schematic diagram of the MEK1 protein with approximate locations of the D, negative regulatory, and core kinase domains indicated. Note that AVM somatic mutations clustered near the negative regulatory domain. The arrows for "F53L" and "D67Y" indicate that p.F53L and p.D67Y variant were found in cis in a single individual. All other variants were found in 2 or more study participants.

FIG. 3A shows a photograph of an upper labial AVM in participant 13 from which CD31+ and CD31− cells were separated. FIG. 3B displays an angiogram prior to resection showing arteriovenous shunting. FIG. 3C shows ddPCR assay results performed on DNA extracted from the AVM (resected tissue), endothelial (CD31+) and non-endothelial (CD31−) cells, and peripheral blood. Droplets containing mutant only, mutant and wild-type, or wild-type only alleles appear in left upper, right upper, and right lower quadrants, respectively (empty droplets are in the left lower quadrant). Percentages of mutant alleles in each sample are indicated (droplet counts are provided in Table 2).

(FIG. 6A) An 11 year-old female underwent resection of a right cheek AVM. The lesion tested negative for the 5 MAP2K1 mutations by ddPCR. ECs from her AVM were isolated and subjected to WES which identified the HRAS mutation. The mutation was not found in her white blood cell DNA. (FIG. 6B) Preoperative angiogram shows the AVM with tortuous arterial feeding vessels (black arrow), a nidus abnormally connecting arteries and veins (circle), and early filling of draining veins (white arrow). (FIG. 6C) MRI illustrates significant adipose tissue of right cheek, which is not present in MAP2K1-AVMs (white arrow). (FIG. 6D) ddPCR graph illustrates the HRAS mutation in isolated ECs (CD31$^+$) from her lesion; mutant allele frequency was 45% (circle; blue droplets left upper quadrant). (FIG. 6E) The mutation then was confirmed in her whole AVM specimen; mutant allele frequency was 5.6% (circle; blue droplets left upper quadrant).

(FIG. 9A) Single cell RNA-seq libraries are prepared with 10× Genomics technology, massively parallel sequenced on the Illumina platform, followed by data deconvolution and analysis using standard pipelines. (FIG. 9B) Multi-dimensional principle components analysis performed on single cell RNAseq from an AVM. CD31$^+$ ECs were maintained in culture for 6 or 8 passages (blue and red dots) and CD31$^-$ non-ECs from the same specimen were kept in culture for 4 and 7 passages (green and purple dots). Individual cells are localized in multi-dimensional space (each dot represents a single cell) based on their gene expression. Note the mutant CD31$^+$ ECs overlap in PCA space and are clearly distinguishable from the non-ECs. (FIG. 9C) Violin plots depict examples of transcripts typical of ECs and non-ECs. Note the CD31+ AVM cells express CDH5/VE-Cadherin, whereas the CD31− cells express PDGFRB. Comparisons and gene discovery will be made by comparing wild-type ECs with mutant ECs, co-cultures of wild-type and mutant ECs, and co-cultures of WT and mutant ECs with pericytes.

FIGS. 10A-10D show human-derived AVM cells form vascularized implants in mice. (Above) Flow cytometry shows homogeneous AVM ECs (top row) and non-ECs (bottom row) from freshly collected human AVM tissue prior to their implantation into immunodeficient mice. AVM-ECs contained an HRAS mutation. (Below), Illustration of vascularized implants. (FIG. 10A) 14 days following implantation of CD31+ and CD31− cells in matrigel shows blue, blood filled implant under the skin. (FIG. 10B) Implant prior to explantation shows it is vascularized with multiple feeding vessels. (FIG. 10C) MR illustrates well-demarcated implant. (FIG. 10D) The implant enhances following contrast administration confirming it is vascularized and consistent with imaging features of human AVM. CD31, VE-Cad=EC markers. CD90=mesenchymal marker. CD45=hematopoietic marker.

FIGS. 11A, 11B show that AVM ECs are required to form excessively vascularized implants in mice. (FIG. 11A) AVM ECs combined with either AVM non-ECs (CD31$^-$) or control non-ECs (MSC) form significantly more vascularized implants compared to control ECs combined with AVM non-ECs (CD31) or control non-ECs (MSC). (FIG. 11B) Microvessel density shows significantly more blood vessels in implants containing AVM-derived ECs (CD31$^+$) (62 vessels/mm$^2$), compared to control ECs (28 vessels/mm$^2$) (p<0.01). AVM ECs contained an HRAS mutation.

DETAILED DESCRIPTION

Figure 1A:
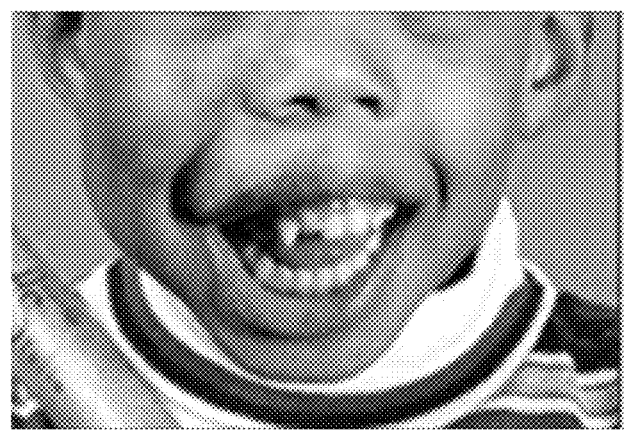
FIGS. 1A to 1I depict AVMs.
Figure 1B:
Figure 1C:
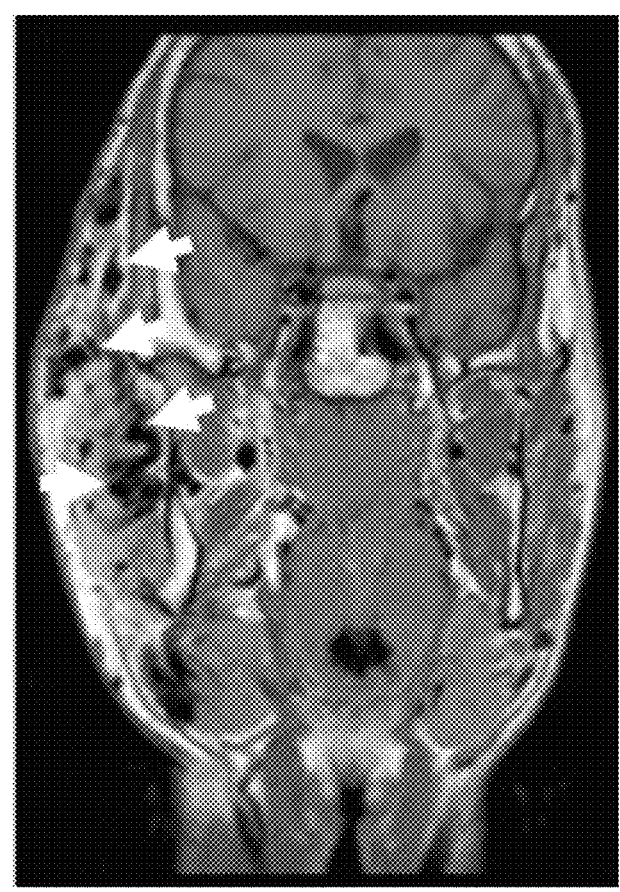
Figure 1D:
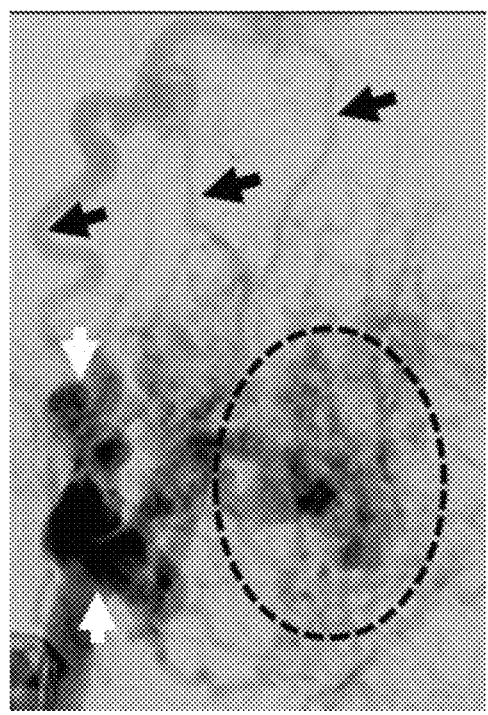
Figure 1E:
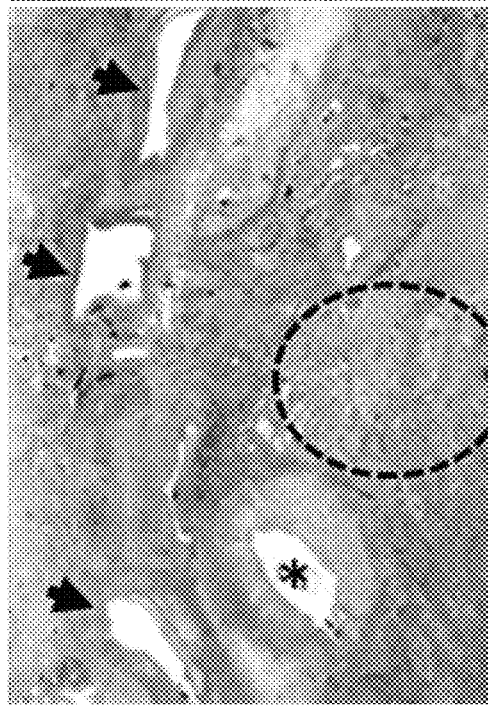
Figure 1F:
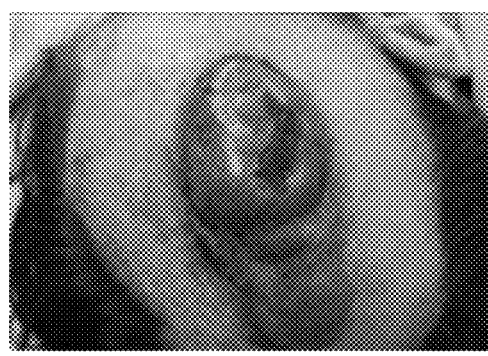
Figure 1G:
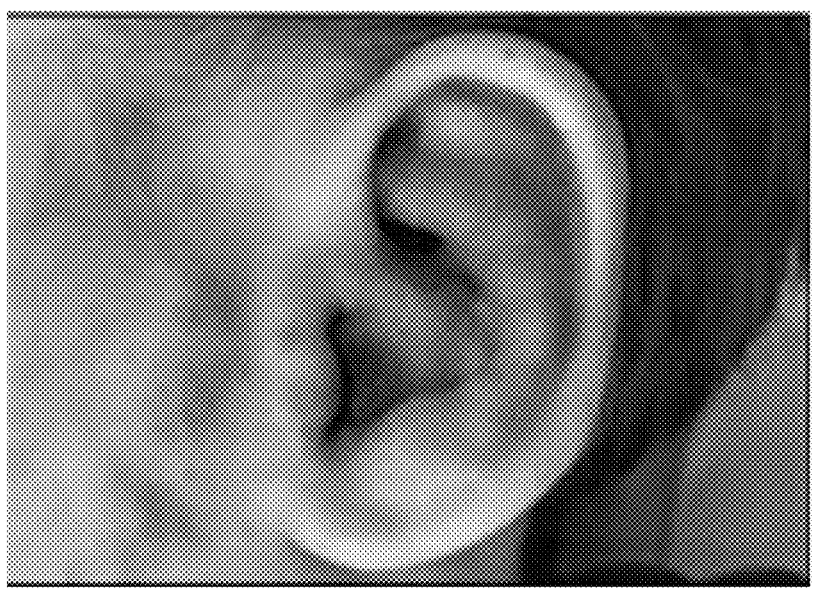
Figure 1H:
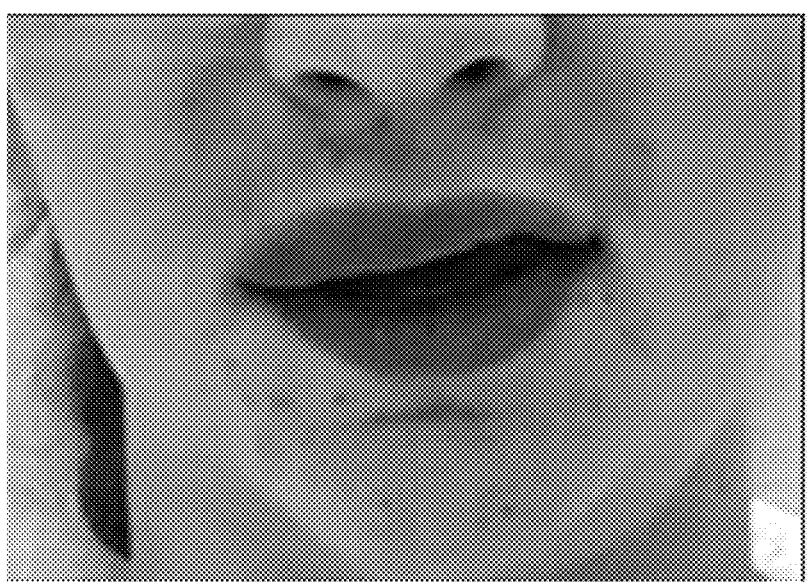
Figure 1I:
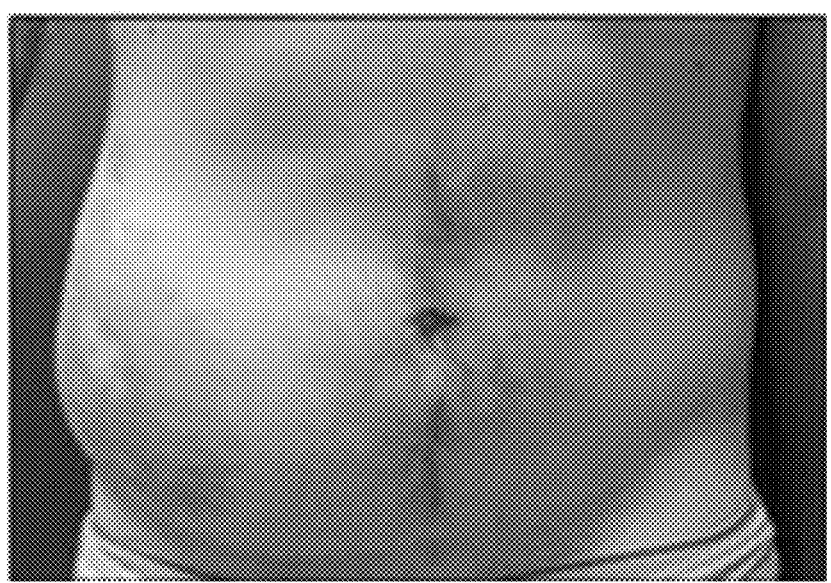
Figure 2A:
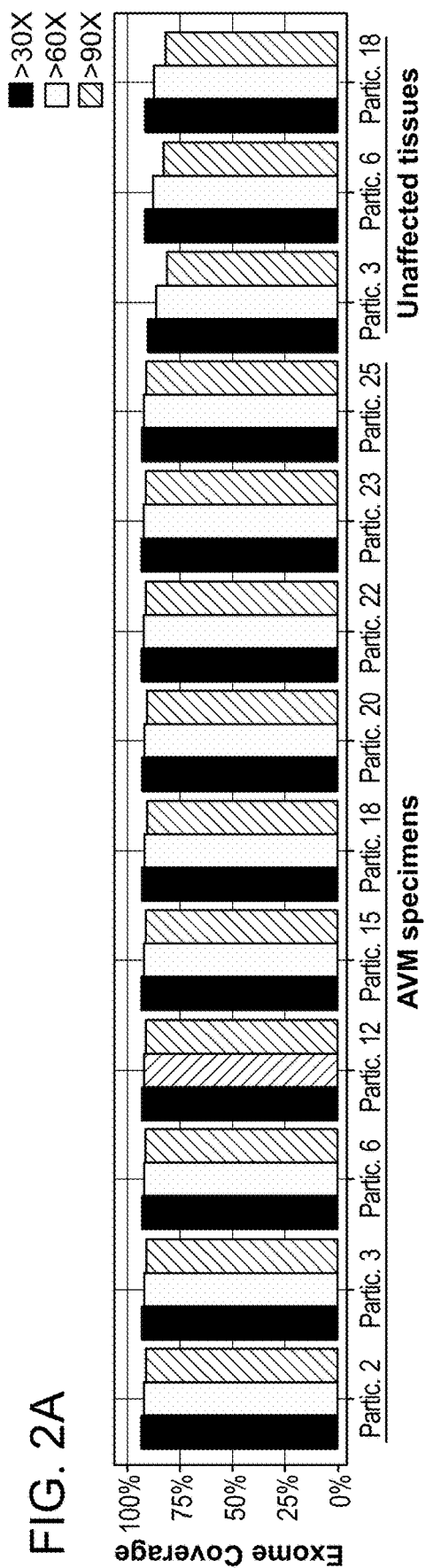
FIGS. 2A to 2C depict somatic mutation detection in AVMs following whole-exome sequencing.
Figure 2B:
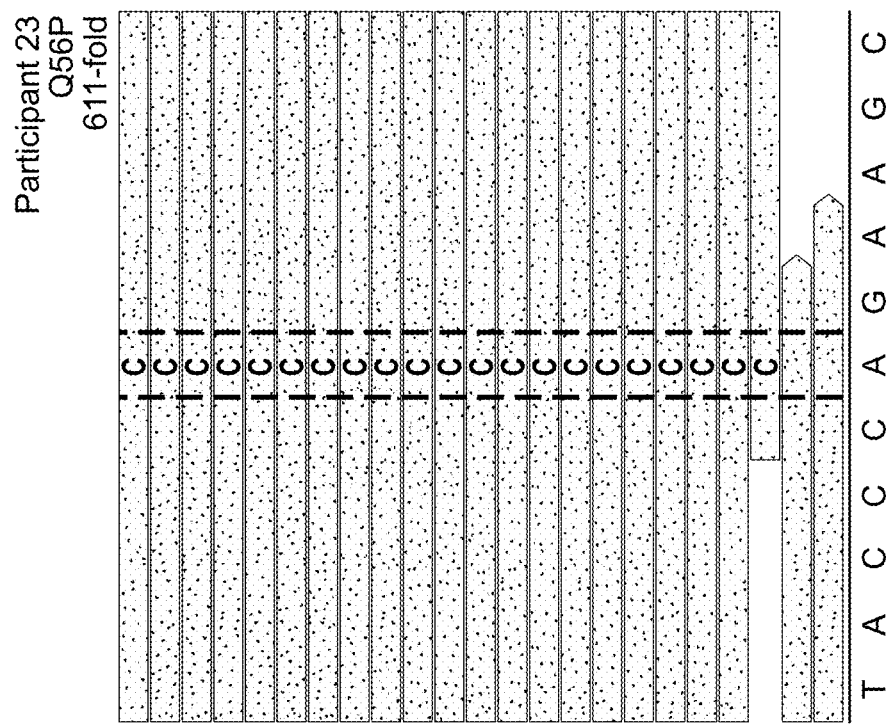
Figure 2B:
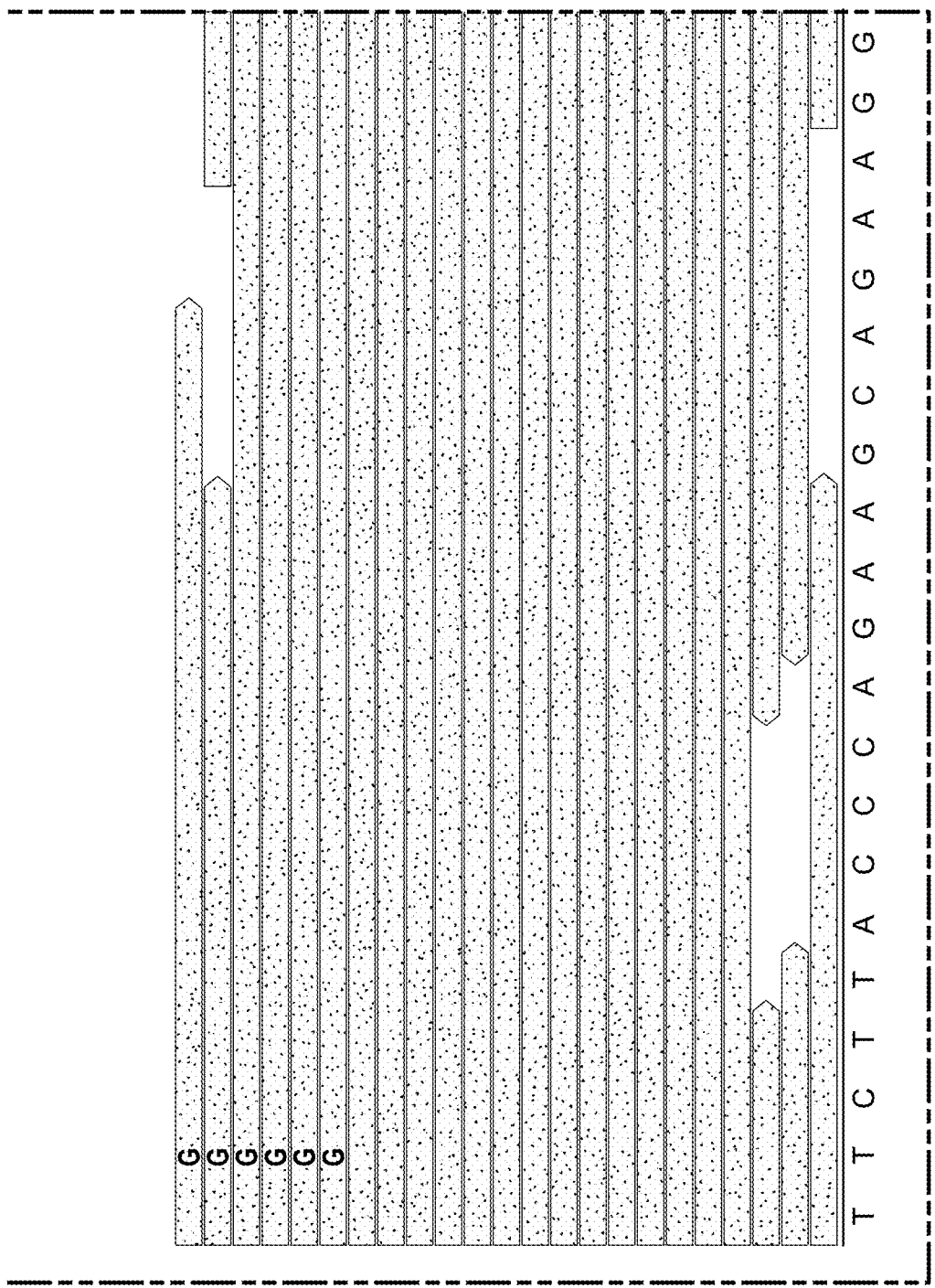
Figure 2B:
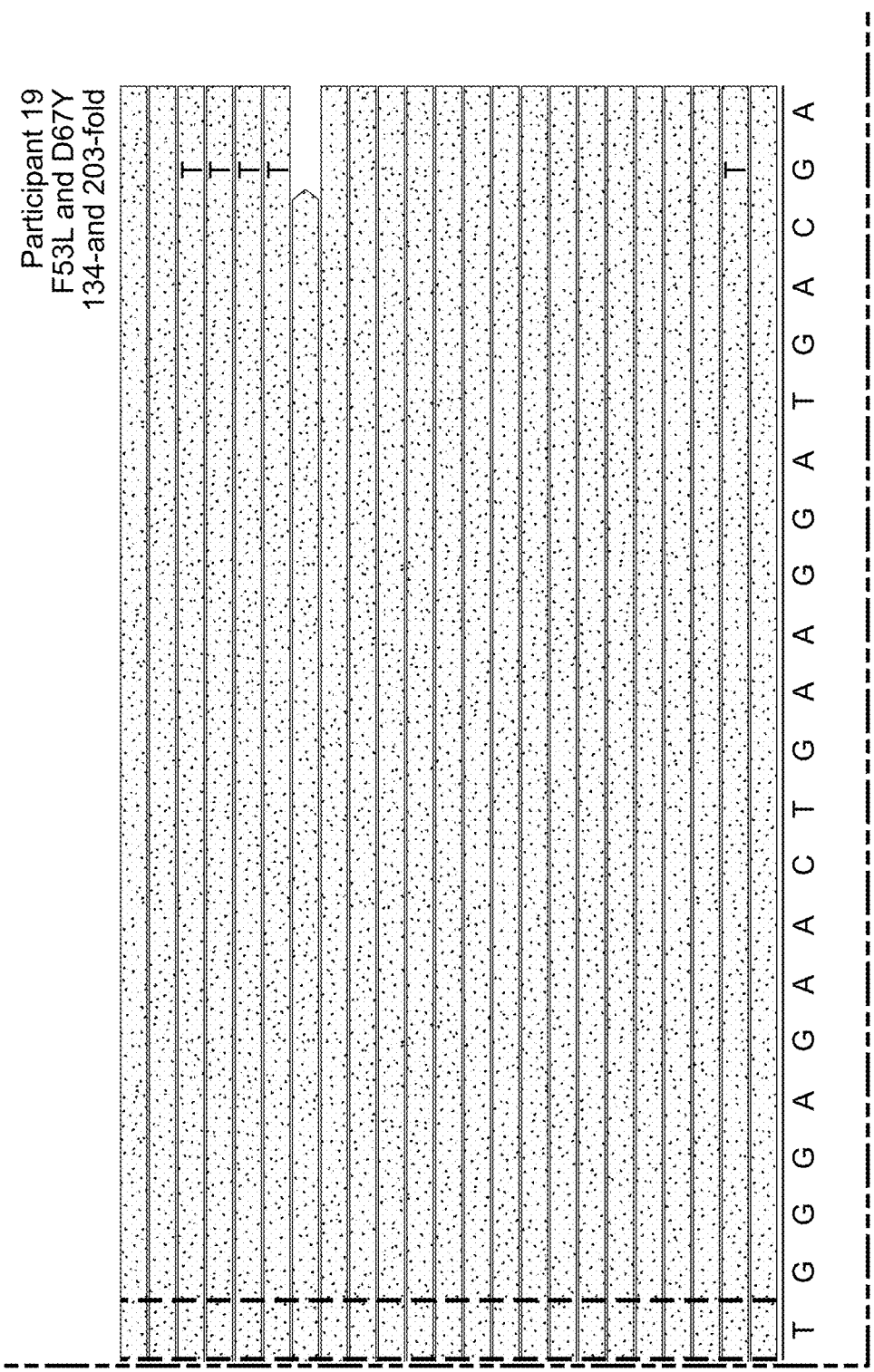
Figure 2B:
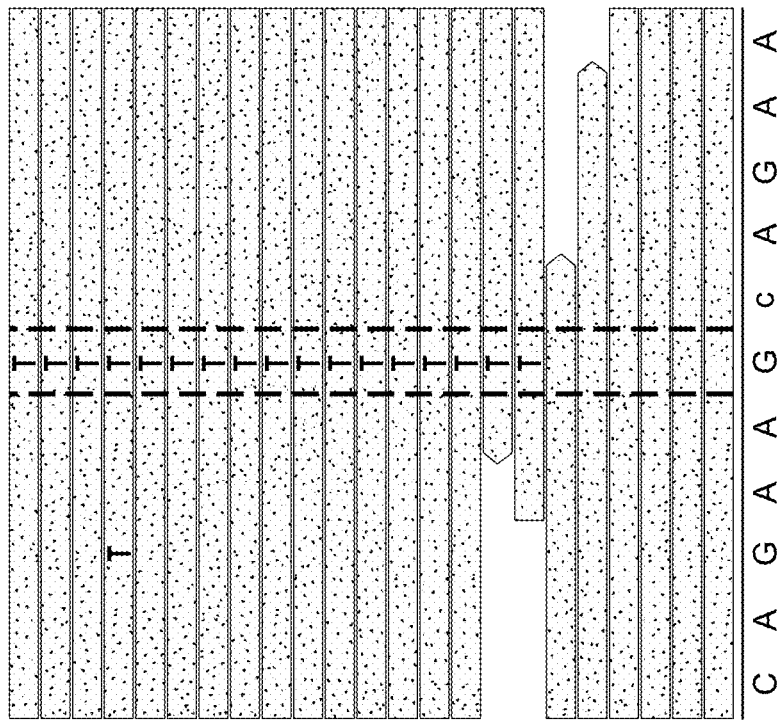
Figure 2B:
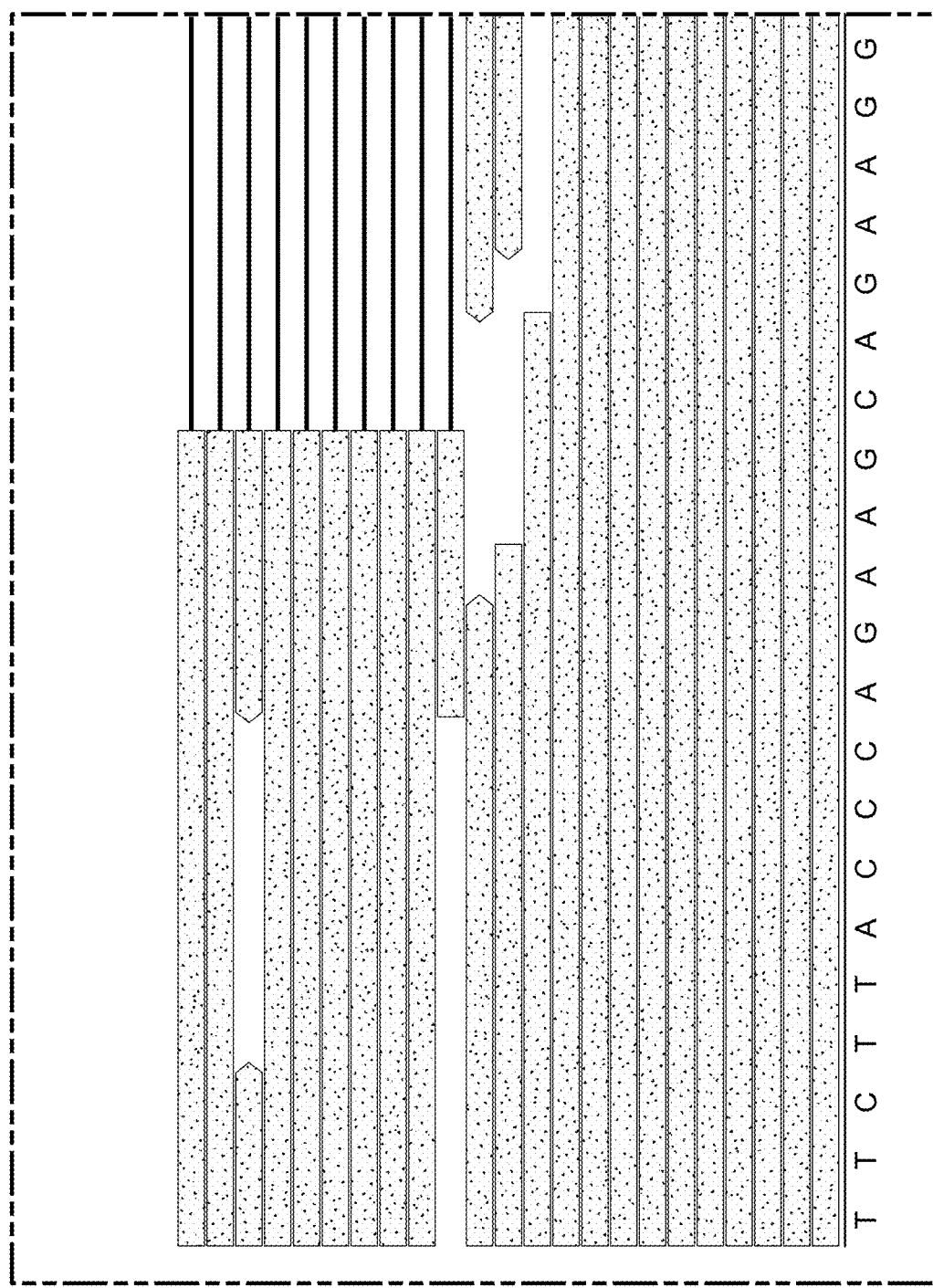
Figure 2B:
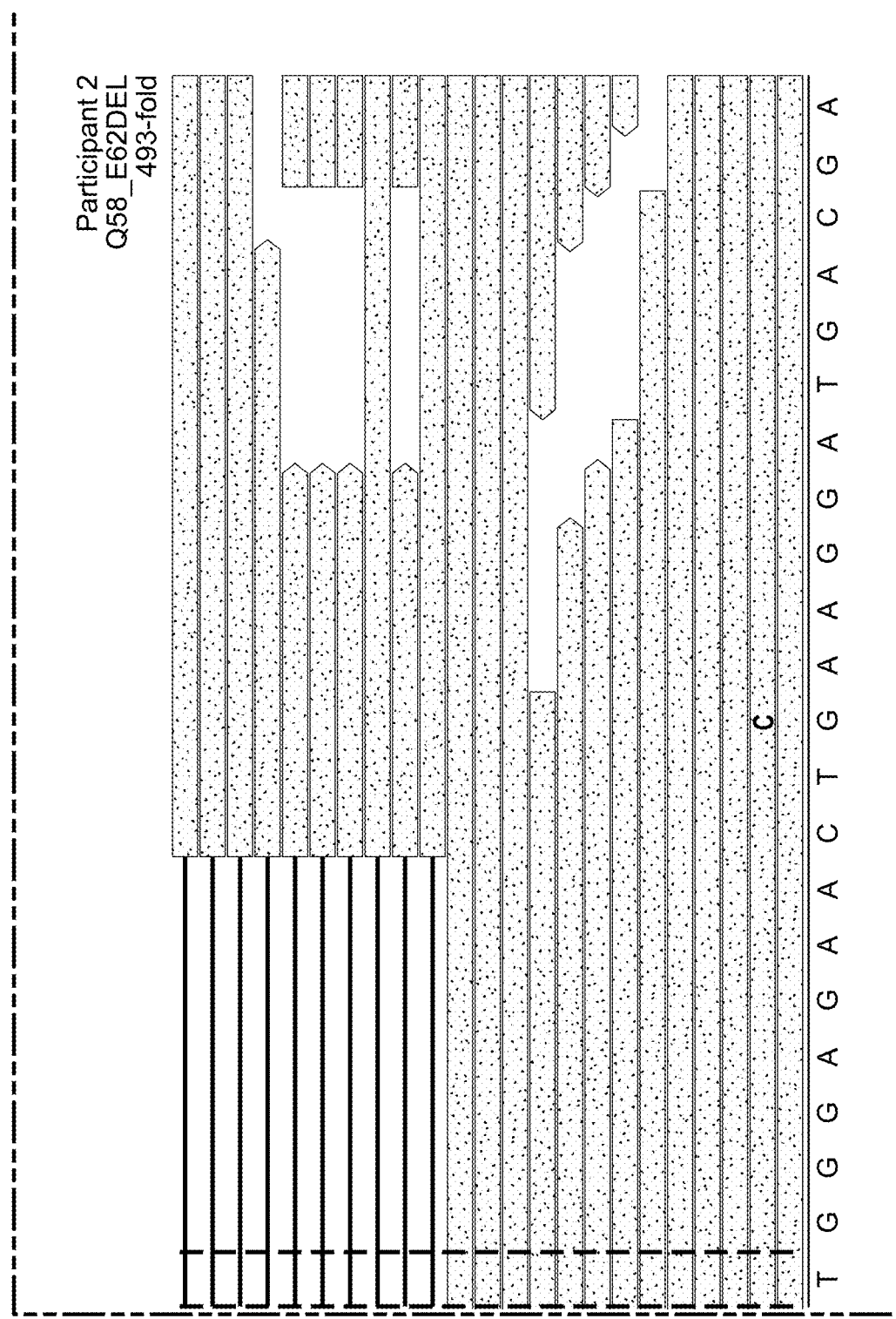
Figure 2C:
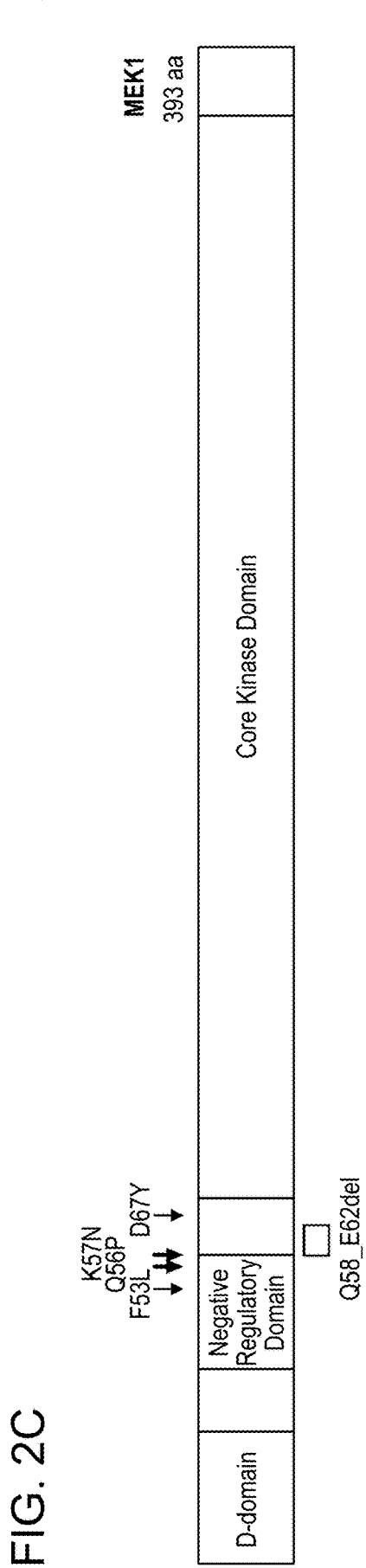

The instant disclosure is based, at least in part, upon the discovery that. Discovery of such a role for MAP2K1 (MEK1), at least in part, indicates that inhibition of MEK1 can treat or prevent a vascular anomaly in a subject, particularly arteriovenous malformation(s) in a subject. Vascular anomalies (i.e., arteriovenous malformation, hemangioma, kaposiform hamangioendothelioma, pyogenic granuloma, capillary malformation, lymphatic malformation and venous malformation) can be effectively treated or prevented in a subject and/or model system via administration of a therapeutically effective/prophylactically effective amount of a MEK1 inhibitor to the subject and/or model system. Use of known MEK1 inhibitors, including small molecule compounds (e.g., trametinib, cobimetinib, binimetinib and selumetinib) and inhibitory nucleic acids is expressly contemplated.

Additional aspects and embodiments of the instant disclosure are described below.

Vascular Anomalies

A vascular anomaly is a kind of birthmark caused by a disorder of the vascular development, although it is not always present at birth. A vascular anomaly is a localized defect in blood vessels that can affect each part of the vasculature (capillaries, arteries, veins, lymphatics or a combination of these). These defects are characterized by an increased number of vessels and vessels that are both enlarged and sinuous. Some vascular anomalies are congenital and therefore present at birth, others appear within weeks to years after birth and others are acquired by trauma or during pregnancy. Inherited vascular anomalies are also described and often present with a number of lesions that increase with patients' age. Vascular anomalies can also be a part of a syndrome and, occasionally, they can be acquired by trauma. The estimated prevalence of vascular anomalies is 4.5% (Greene, A K (January 2011). "Vascular anomalies: current overview of the field.". *Clinics in plastic surgery.* 38 (1): 1-5). Vascular anomalies can occur throughout the whole body (skin, bone, liver, intestines, i.e.), but in 60% of patients vascular anomalies are localized in the head and neck region (Ernemann, U; Kramer, U; Miller, S; Bisdas, S; Rebmann, H; Breuninger, H; Zwick, C; Hoffmann, J (July 2010). "Current concepts in the classification, diagnosis and treatment of vascular anomalies.". European journal of radiology. 75 (1): 2-11). Vascular anomalies can present in various ways. Vascular anomalies that are situated deep below the skin, appear blue and are often called cavernous. Superficial vascular anomalies appear as red-coloured stains and are associated with vascular anomalies affecting the dermis. Historically, vascular anomalies have been labeled with descriptive terms, according to the food they resembled (port wine, strawberry, cherry, salmon patch). This imprecise terminology has caused diagnostic confusion, blocked communication and even caused incorrect treatment, as it does not differentiate between various vascular anomalies (Hassanein, A H; Mulliken, J B; Fishman, S J; Greene, A K (January 2011). "Evaluation of terminology for vascular anomalies in current literature.". *Plastic and Reconstructive Surgery.* 127 (1): 347-51). However, in 1982, Mulliken introduced a classification that replaced these descriptive terms and gave direction to the management of various vascular anomalies. This classification, based on clinical features, natural history and cellular characteristics, divides vascular anomalies into two groups: vascular tumors and vascular malformations (Mulliken, J B; Glowacki, J (March 1982). "Hemangiomas and vascular malformations in infants and children: a classification based on endothelial characteristics.". *Plastic and Reconstructive Surgery.* 69 (3): 412-22). Although the appearance of both vascular tumors and vascular malformations can resemble, there are important differences between both.

Vascular Malformations

Vascular malformation is a collective term for different disorders of the vasculature (errors in vascular development). It can be a disorder of the capillaries, arteries, veins and lymphatic vessels or a disorder of a combination of these (lesions are named based on the primary vessel that is malformed). A vascular malformation consists of a cluster of deformed vessels, due to an error in vascular development (dysmorphogenesis). However, endothelial turnover is stable in these defects. Congenital vascular malformations are always already present at birth, although they are not always visible. In contrast to vascular tumors, vascular malformations do not have a growth phase, nor an involution phase. Vascular malformations tend to grow proportionately with the child (Chim, H; Drolet, B; Duffy, K; Koshima, I; Gosain, A K (August 2010). "Vascular anomalies and lymphedema.". *Plastic and Reconstructive Surgery.* 126 (2): 55e-69e). Vascular malformations never regress, but persist throughout life. Vascular malformations can be divided into slow-flow, fast-flow and complex-combined types (Enjolras, O (2007). "Introduction: ISSVA Classification". Color atlas of vascular tumors and vascular malformations. Cambridge [u.a.]: Cambridge University Press).

Slow-Flow Vascular Malformations

Capillary malformation (also known as port-wine stains): Capillary malformations are flat, reddish lesions that typically affect the skin, mostly around the head and the neck, and which darken with age, in contrast to birthmarks such as salmon patch, Nevus simplex or vascular stain, which lighten or disappear within the first few years of life. Capillary malformations constitute 11% of the vascular malformations (Greene, A K (January 2011). "Vascular anomalies: current overview of the field.". *Clinics in plastic surgery.* 38 (1): 1-5). Syndromes associated with capillary malformations are: Sturge-Weber syndrome and Klippel-Trenaunay syndrome (Enjolras, O (2007). "Introduction: ISSVA Classification". Color atlas of vascular tumors and vascular malformations. Cambridge [u.a.]: Cambridge University Press). Capillary malformations can be treated with IPL-(Intensed-pulsed-light)-therapy or surgical reduction (Ernemann, U; Kramer, U; Miller, S; Bisdas, S; Rebmann, H; Breuninger, H; Zwick, C; Hoffmann, J (July 2010). "Current concepts in the classification, diagnosis and treatment of vascular anomalies.". *European journal of radiology.* 75 (1): 2-11).

Venous malformation is a bluish lesion compressible on palpation; the masses enlarge with physical activity or if in a dependent position. The bluish lesion is caused by dilated venous vessels. Venous malformations can be painful in the morning due to stasis and microthrombi within the veins. Venous malformations usually occur in the head and neck (Chim, H; Drolet, B; Duffy, K; Koshima, I; Gosain, A K (August 2010). "Vascular anomalies and lymphedema.". *Plastic and Reconstructive Surgery.* 126 (2): 55e-69e). Venous malformations are the most common vascular anomaly, making up 40% of all vascular malformations (Greene, A K (January 2011). "Vascular anomalies: current overview of the field.". *Clinics in plastic surgery.* 38 (1): 1-5). They can be treated with sclerotherapy and surgical reduction (Ernemann, U; Kramer, U; Miller, S; Bisdas, S; Rebmann, H; Breuninger, H; Zwick, C; Hoffmann, J (July 2010). "Current concepts in the classification, diagnosis and treatment of vascular anomalies.". *European journal of radiology.* 75 (1): 2-11).

Lymphatic malformation is a benign growth of the lymphatic system (Perkins J A, Manning S C, Tempero R M, Cunningham M J, Edmonds J L, Hoffer F A, Egbert M A (June 2010). "Lymphatic malformations: current cellular and clinical investigations.". *Otolaryngology—head and neck surgery: official journal of American Academy of Otolaryngology—Head and Neck Surgery.* 142 (6): 789-94). They result from a blockage or defect of the lymphatic vessels as they are forming. 28% of all vascular malformations are lymphatic malformations (Greene, A K (January 2011). "Vascular anomalies: current overview of the field.". *Clinics in plastic surgery.* 38 (1): 1-5). Lymphatic malformations can be treated with sclerotherapy and surgical reduction (Ernemann, U; Kramer, U; Miller, S; Bisdas, S; Rebmann, H; Breuninger, H; Zwick, C; Hoffmann, J (July 2010). "Current concepts in the classification, diagnosis and treatment of vascular anomalies.". *European journal of radiology.* 75 (1): 2-11).

Fast Flow Vascular Malformations

Fast-flow malformations are malformations involving arteries. They constitute about 14% of all vascular malformations (Greene, A K (January 2011). "Vascular anomalies: current overview of the field.". *Clinics in plastic surgery.* 38 (1): 1-5).

Arterial Malformation

Arteriovenous fistula (AVF): a lesion with a direct communication via fistulae between an artery and a vein (Ernemann, U; Kramer, U; Miller, S; Bisdas, S; Rebmann, H; Breuninger, H; Zwick, C; Hoffmann, J (July 2010). "Current concepts in the classification, diagnosis and treatment of vascular anomalies.". *European journal of radiology.* 75 (1): 2-11).

Arteriovenous malformation: a lesion with a direct connection between an artery and a vein, without an intervening capillary bed, but with an interposed nidus of dysplastic vascular channels in between (Chim, H; Drolet, B; Duffy, K; Koshima, I; Gosain, A K (August 2010). "Vascular anomalies and lymphedema.". *Plastic and Reconstructive Surgery.* 126 (2): 55e-69e).

Combined-Complex Vascular Malformations

A combination of various vascular malformations. They are 'complex' because they involve a combination of two different types of vessels.

CVM: capillary venous malformation
CLM: capillary lymphatic malformation
LVM: lymphatic venous malformation
CLVM: capillary lymphatic venous malformation. CLVM is associated with Klippel-Trenaunay syndrome
AVM-LM: Arteriovenous malformation-lymphatic malformation
CM-AVM: capillary malformation-arteriovenous malformation (Enjolras, O (2007). "Introduction: ISSVA Classification". Color atlas of vascular tumors and vascular malformations. Cambridge [u.a.]: Cambridge University Press).

Arteriovenous Malformations (AVMs)

Arteriovenous malformation (AVM) is an abnormal connection between arteries and veins, bypassing the capillary system. This vascular anomaly is widely known because of its occurrence in the central nervous system (usually cerebral AVM), but can appear in any location. Although many AVMs are asymptomatic, they can cause intense pain or bleeding or lead to other serious medical problems.

AVMs are usually congenital and belong to the RASopathies. The genetic transmission patterns of AVM, if any, are unknown. AVM is not generally thought to be an inherited disorder, unless in the context of a specific hereditary syndrome.

Symptoms of AVM vary according to the location of the malformation. Roughly 88% (National Institute of Neurological Disorders and Stroke) of people affected with AVM are asymptomatic; often the malformation is discovered as part of an autopsy or during treatment of an unrelated disorder (called in medicine "an incidental finding"); in rare cases its expansion or a micro-bleed from an AVM in the brain can cause epilepsy, neurological deficit or pain.

The most general symptoms of a cerebral AVM include headache and epilepsy, with more specific symptoms occurring that normally depend on the location of the malformation and the individual. Such possible symptoms include (Arteriovenous Malformation Information Page at NINDS):

Difficulties with movement coordination, including muscle weakness and even paralysis;

vertigo (dizziness);

Difficulties of speech (dysarthria) and communication, such as aphasia;

Difficulties with everyday activities, such as apraxia;

Abnormal sensations (numbness, tingling, or spontaneous pain);

Memory and thought-related problems, such as confusion, dementia or hallucinations.

Cerebral AVMs may present in a number of ways

Hemorrhage (45% of cases) Acute onset of severe headache. May be described as the worst headache of the patient's life. Depending on the location of hemorrhage, may be associated with new fixed neurologic deficit. In unruptured brain AVMs, the risk of spontaneous hemorrhage may be as low as 1% per year. After a first rupture, the annual bleeding risk may increase to more than 5% (Stapf, C.; Mast, H.; Sciacca, R. R.; Choi, J. H.; Khaw, A. V.; Connolly, E. S.; Pile-Spellman, J.; Mohr, J. P. (2006). *Neurology.* 66 (9): 1350-5).

Seizure or brain seizure (46%) Depending on place of AVM it can cause loss of vision in one place.

Headache (34%)

Progressive neurologic deficit (21%) May be caused by mass effect or venous dilatations. Presence and nature of deficit depend on location of lesion and the draining veins (Choi, J. H.; Mast, H.; Hartmann, A.; Marshall, R. S.; Pile-Spellman, J.; Mohr, J. P.; Stapf, C. (2009). *Journal of the Neurological Sciences.* 287 (1-2): 126-30).

Pediatric patients Heart failure

Macrocephaly

Prominent scalp veins

Pulmonary arteriovenous malformations

In the lungs, pulmonary arteriovenous malformations have no symptoms in up to 29% of cases (Goodenberger D M (2008). *Fishman's Pulmonary Diseases and Disorders* (4th ed.). McGraw-Hill. p. 1470).

In a normal functioning human body, arteries carry blood away from the heart to the lungs or the rest of the body, where the blood passes through capillaries, and veins return the blood to heart. An AVM interferes with this process by forming a direct connection of the arteries and veins. AVMs can cause intense pain and lead to serious medical problems. Although AVMs are often associated with the brain and spinal cord, they can develop in any part of the body.

Arteries and veins are part of the human cardiovascular system. Normally, the arteries in the vascular system carry oxygen-rich blood, except in the case of the pulmonary artery. Structurally, arteries divide and sub-divide repeatedly, eventually forming a sponge-like capillary bed. Blood moves through the capillaries, giving up oxygen and taking up waste products, including $CO_2$, from the surrounding cells. Capillaries in turn successively join together to form veins that carry blood away. The heart acts to pump blood through arteries and uptake the venous blood.

An AVM lacks the dampening effect of capillaries on the blood flow, which means that the AVM can get progressively larger over time as the amount of blood flowing through it increases, forcing the heart to work harder to keep up with the extra blood flow. It also causes the surrounding area to be deprived of the functions of the capillaries—removal of $CO_2$ and delivery of nutrients to the cells. The resulting tangle of blood vessels, often called a nidus (Latin for "nest"), has no capillaries. It can be extremely fragile and prone to bleeding because of the abnormally direct connections between high-pressure arteries and low-pressure veins. The resultant sign, audible via stethoscope, is a rhythmic, whooshing sound caused by excessively rapid blood flow through the arteries and veins. It has been given the term "bruit", French for noise. On some occasions a patient with a brain AVM may become aware of the noise, which can compromise hearing and interfere with sleep in addition to causing psychological distress.

AVMs are diagnosed primarily by the following methods:

Computerized tomography (CT) scan is a noninvasive X-ray to view the anatomical structures within the brain to detect blood in or around the brain. A newer technology called CT angiography involves the injection of contrast into the blood stream to view the arteries of the brain. This type of test provides the best pictures of blood vessels through angiography and soft tissues through CT.

Magnetic resonance imaging (MRI) scan is a noninvasive test, which uses a magnetic field and radio-frequency waves to give a detailed view of the soft tissues of the brain.

Magnetic resonance angiography (MRA)—scans created using magnetic resonance imaging to specifically image the blood vessels and structures of the brain. A magnetic resonance angiogram can be an invasive procedure, involving the introduction of contrast dyes (e.g., gadolinium MR contrast agents) into the vasculature of a patient using a catheter inserted into an artery and passed through the blood vessels to the brain. Once the catheter is in place, the contrast dye is injected into the bloodstream and the MR images are taken. Additionally or alternatively, flow-dependent or other contrast-free magnetic resonance imaging techniques can be used to determine the location and other properties of the vasculature.

AVMs can occur in various parts of the body:

brain, spleen (Agrawal, Aditya; Whitehouse, Richard; Johnson, Robert W.; Augustine, Titus (2006). *Journal of Vascular Surgery.* 44 (6): 1345-9)

lung (Chowdhury, Ujjwal K.; Kothari, Shyam S.; Bishnoi, Arvind K.; Gupta, Ruchika; Mittal, Chander M.; Reddy, Srikrishna (2009). *Heart, Lung and Circulation.* 18 (2): 135-9)

kidney (Barley, Fay L.; Kessel, David; Nicholson, Tony; Robertson, Iain (2006). *CardioVascular and Interventional Radiology.* 29 (6): 1084-7)

spinal cord (Kishi, K; Shirai, S; Sonomura, T; Sato, M (2005). *The British Journal of Radiology.* 78 (927): 252-4)

liver (Bauer, Tilman; Britton, Peter; Lomas, David; Wight, Derek G. D.; Friend, Peter J.; Alexander, Graeme J. M. (1995). *Journal of Hepatology.* 22 (5): 586-90)

intercostal space (Rivera, Peter P.; Kole, Max K.; Pelz, David M.; Gulka, Irene B.; McKenzie, F. Neil; Lownie, Stephen P. (2006). *American Journal of Roentgenology.* 187 (5): W503-6)

iris (Shields, Jerry A.; Streicher, Theodor F. E.; Spirkova, Jane H. J.; Stubna, Michal; Shields, Carol L. (2006). *Archives of Ophthalmology.* 124 (3): 370-5)

spermatic cord (Sountoulides, Petros; Bantis, Athanasios; Asouhidou, Irene; Aggelonidou, Hellen (2007). *Journal of Medical Case Reports.* 1: 110)

Extremities—arm, shoulder, etc.

AVMs may occur in isolation or as a part of another disease (for example, Von Hippel-Lindau disease or hereditary hemorrhagic telangiectasia).

AVMs have been shown to be associated with aortic stenosis (Batur, Pelin; Stewart, William J.; Isaacson, J. Harry (2003). *Archives of Internal Medicine.* 163 (15): 1821-4).

Bleeding from an AVM can be relatively mild or devastating. It can cause severe and less often fatal strokes. If a cerebral AVM is detected before a stroke occurs, usually the arteries feeding blood into the nidus can be closed off to avert the danger. However, interventional therapy may also be relatively risky.

Treatment for brain AVMs can be symptomatic, and patients should be followed by a neurologist for any seizures, headaches or focal deficits. AVM-specific treatment may also involve endovascular embolization, neurosurgery or radiosurgery (Arteriovenous Malformation Information Page at NINDS). Embolization, that is, cutting off the blood supply to the AVM with coils or particles or glue introduced by a radiographically guided catheter, may be used in addition to neurosurgery or radiosurgery, but is rarely successful in isolation except in smaller AVMs. Gamma knife may also be used.

The Spetzler-Martin grading system developed at the Barrow Neurological Institute is utilized by neurosurgeons to determine operative versus nonoperative management of AVMs.

Arteriovenous malformation (AVM) is a devastating disease without a cure. Drugs are not available for AVM and they are treated with resection or embolization; unfortunately, almost all AVMs regrow following these interventions.

The current disclosure is based, at least in part, upon discovery of the cause of sporadic, extracranial AVMs to be a somatic mutation in the gene MAP2K1 (MEK1). Germline mutations in this gene previously have been shown to cause cardio-facio-cutaneous syndrome. Somatic mutations in MAP2K1 previously have been found in melanoma and lung cancer. However, the instant disclosure is believed to be the first example of a somatic mutation in this gene causing a vascular anomaly. Currently, MAP2K1 inhibitors are being used orally for melanoma.

MAP2K1 (MEK1)

MAPK was originally called "extracellular signal-regulated kinase" (ERK) and "microtubule associated protein kinase" (MAPK). "MAP2K1" or "MEK1", also referred to as "dual specificity mitogen-activated protein kinase kinase 1", acts as an essential component of the MAP kinase signal transduction pathway. Binding of extracellular ligands such as growth factors, cytokines and hormones to their cell-surface receptors activates RAS and this initiates RAF1 activation. RAF1 then further activates the dual-specificity protein kinases MAP2K1/MEK1 and MAP2K2/MEK2. Both MAP2K1/MEK1 and MAP2K2/MEK2 function specifically in the MAPK/ERK cascade, and catalyze the concomitant phosphorylation of a threonine and a tyrosine residue located in the extracellular signal-regulated kinases MAPK3/ERK1 and MAPK1/ERK2, leading to their activation and further transduction of the signal within the MAPK/ERK cascade. Depending on the cellular context, this pathway mediates diverse biological functions such as cell growth, adhesion, survival and differentiation, predominantly through the regulation of transcription, metabolism and cytoskeletal rearrangements. One target of the MAPK/ERK cascade is peroxisome proliferator-activated receptor gamma (PPARG), a nuclear receptor that promotes differentiation and apoptosis. MAP2K1/MEK1 has been shown to export PPARG from the nucleus. The MAPK/ERK cascade is also involved in the regulation of endosomal dynamics, including lysosome processing and endosome cycling through the perinuclear recycling compartment (PNRC), as well as in the fragmentation of the Golgi apparatus during mitosis.

Ras proteins such as HRAS mediate the activation of RAF proteins such as RAF1 or BRAF which in turn activate extracellular signal-regulated kinases (ERK) through MAPK (mitogen-activated protein kinases) and ERK kinases MAP2K1/MEK1 and MAP2K2/MEK2. Activation occurs through phosphorylation of Ser-218 and Ser-222. MAP2K1/MEK1 is also the target of negative feed-back regulation by its substrate kinases, such as MAPK1/ERK2. These phosphorylate MAP2K1/MEK1 on Thr-292, thereby facilitating dephosphorylation of the activating residues Ser-218 and Ser-222. Inhibited by serine/threonine phosphatase 2A (By similarity). Many inhibitors have been identified including pyrrole derivatives, TAK-733 (one of a series of 8-methylpyrido[2,3-d]pyrimidine-4,7(3H,8H)-dione derivatives), CH4987655 and RDEA119/BAY 869766.

```
A representative human MAP2K1 nucleic acid
sequence is NM_002755 (SEQ ID NO: 1):
AGGCGAGGCTTCCCCTTCCCCGCCCCTCCCCCGGCCTCCAGTCCCTCC

CAGGGCCGCTTCGCAGAGCGGCTAGGAGCACGGCGGCGGCGGCACTTT

CCCCGGCAGGAGCTGGAGCTGGGCTCTGGTGCGCGCGCGGCTGTGCCG

CCCGAGCCGGAGGGACTGGTTGGTTGAGAGAGAGAGAGGAAGGGAATC

CCGGGCTGCCGAACCGCACGTTCAGCCCGCTCCGCTCCTGCAGGGCAG

CCTTTCGGCTCTCTGCGCGCGAAGCCGAGTCCCGGGCGGGTGGGCGG

GGGTCCACTGAGACCGCTACCGGCCCCTCGGCGCTGACGGGACCGCGC

GGGGCGCACCCGCTGAAGGCAGCCCCGGGGCCCGCGGCCCGGACTTGG

TCCTGCGCAGCGGGCGCGGGGCAGCGCAGCGGGAGGAAGCGAGAGGTG

CTGCCCTCCCCCCGGAGTTGGAAGCGCGTTACCCGGGTCCAAAATGCC

CAAGAAGAAGCCGACGCCCATCCAGCTGAACCCGGCCCCCGACGGCTC

TGCAGTTAACGGGACCAGCTCTGCGGAGACCAACTTGGAGGCCTTGCA

GAAGAAGCTGGAGGAGCTAGAGCTTGATGAGCAGCAGCGAAAGCGCCT

TGAGGCCTTTCTTACCCAGAAGCAGAAGGTGGGAGAACTGAAGGATGA

CGACTTTGAGAAGATCAGTGAGCTGGGGGCTGGCAATGGCGGTGTGGT

GTTCAAGGTCTCCCACAAGCCTTCTGGCCTGGTCATGGCCAGAAAGCT

AATTCATCTGGAGATCAAACCCGCAATCCGGAACCAGATCATAAGGGA

GCTGCAGGTTCTGCATGAGTGCAACTCTCCGTACATCGTGGGCTTCTA

TGGTGCGTTCTACAGCGATGGCGAGATCAGTATCTGCATGGAGCACAT

GGATGGAGGTTCTCTGGATCAAGTCCTGAAGAAAGCTGGAAGAATTCC

TGAACAAATTTTAGGAAAAGTTAGCATTGCTGTAATAAAAGGCCTGAC

ATATCTGAGGGAGAAGCACAAGATCATGCACAGAGATGTCAAGCCCTC
```

```
CAACATCCTAGTCAACTCCCGTGGGGAGATCAAGCTCTGTGACTTTGG

GGTCAGCGGGCAGCTCATCGACTCCATGGCCAACTCCTTCGTGGGCAC

AAGGTCCTACATGTCGCCAGAAAGACTCCAGGGGACTCATTACTCTGT

GCAGTCAGACATCTGGAGCATGGGACTGTCTCTGGTAGAGATGGCGGT

TGGGAGGTATCCCATCCCTCCTCCAGATGCCAAGGAGCTGGAGCTGAT

GTTTGGGTGCCAGGTGGAAGGAGATGCGGCTGAGACCCCACCCAGGCC

AAGGACCCCGGGAGGCCCCTTAGCTCATACGGAATGGACAGCCGACC

TCCCATGGCAATTTTTGAGTTGTTGGATTACATAGTCAACGAGCCTCC

TCCAAAACTGCCCAGTGGAGTGTTCAGTCTGGAATTTCAAGATTTTGT

GAATAAATGCTTAATAAAAAACCCCGCAGAGAGAGCAGATTTGAAGCA

ACTCATGGTTCATGCTTTTATCAAGAGATCTGATGCTGAGGAAGTGGA

TTTTGCAGGTTGGCTCTGCTCCACCATCGGCCTTAACCAGCCCAGCAC

ACCAACCCATGCTGCTGGCGTCTAAGTGTTTGGGAAGCAACAAAGAGC

GAGTCCCCTGCCCGGTGGTTTGCCATGTCGCTTTTGGGCCTCCTTCCC

ATGCCTGTCTCTGTTCAGATGTGCATTTCACCTGTGACAAAGGATGAA

GAACACAGCATGTGCCAAGATTCTACTCTTGTCATTTTTAATATTACT

GTCTTTATTCTTATTACTATTATTGTTCCCCTAAGTGGATTGGCTTTG

TGCTTGGGGCTATTTGTGTGTATGCTGATGATCAAAACCTGTGCCAGG

CTGAATTACAGTGAAATTTTGGTGAATGTGGGTAGTCATTCTTACAAT

TGCACTGCTGTTCCTGCTCCATGACTGGCTGTCTGCCTGTATTTTCGG

GATTCTTTGACATTTGGTGGTACTTTATTCTTGCTGGGCATACTTTCT

CTCTAGGAGGGAGCCTTGTGAGATCCTTCACAGGCAGTGCATGTGAAG

CATGCTTTGCTGCTATGAAAATGAGCATCAGAGAGTGTACATCATGTT

ATTTTATTATTATTATTTGCTTTTCATGTAGAACTCAGCAGTTGACAT

CCAAATCTAGCCAGAGCCCTTCACTGCCATGATAGCTGGGGCTTCACC

AGTCTGTCTACTGTGGTGATCTGTAGACTTCTGGTTGTATTTCTATAT

TTATTTTCAGTATACTGTGTGGGATACTTAGTGGTATGTCTCTTTAAG

TTTTGATTAATGTTTCTTAAATGGAATTATTTTGAATGTCACAAATTG

ATCAAGATATTAAAATGTCGGATTTATCTTTCCCCATATCCAAGTACC

AATGCTGTTGTAAACAACGTGTATAGTGCCTAAAATTGTATGAAAATC

CTTTTAACCATTTTAACCTAGATGTTTAACAAATCTAATCTCTTATTC

TAATAAATACTATGAAATAAAAAAAAAAGGATGAAAGCTAAAAAAA

AAAAAAAAAA
```

The corresponding human MEK1 (MAP2K1) protein
sequence is NP_002746.1 (SEQ ID NO: 2):
MPKKKPTPIQLNPAPDGSAVNGTSSAETNLEALQKKLEELELDEQQRK

RLEAFLTQKQKVGELKDDDFEKISELGAGNGGVVFKVSHKPSGLVMAR

KLIHLEIKPAIRNQIIRELQVLHECNSPYIVGFYGAFYSDGEISICME

HMDGGSLDQVLKKAGRIPEQILGKVSIAVIKGLTYLREKHKIMHRDVK

PSNILVNSRGEIKLCDFGVSGQLIDSMANSFVGTRSYMSPERLQGTHY

SVQSDIWSMGLSLVEMAVGRYPIPPPDAKELELMFGCQVEGDAAETPP

RPRTPGRPLSSYGMDSRPPMAIFELLDYIVNEPPPKLPSGVFSLEFQD

FVNKCLIKNPAERADLKQLMVHAFIKRSDAEEVDFAGWLCSTIGLNQP

STPTHAAGV

MAP2K1 (MEK1) Inhibitors

Known MAP2K1 (MEK1) inhibitors include the following:

Trametinib:

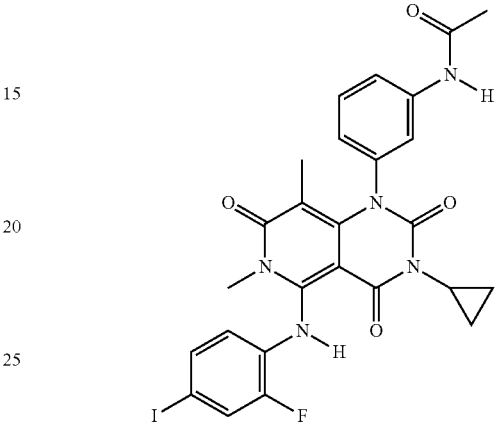

N-(3-{3-Cyclopropyl-5-[(2-fluoro-4-iodophenyl)amino]-6,
8-dimethyl-2,4,7-trioxo-3,4,6,7-tetrahydropyrido[4,3-d]
pyrimidin-1(2H)-yl}phenyl)acetamide Cobimetinib:

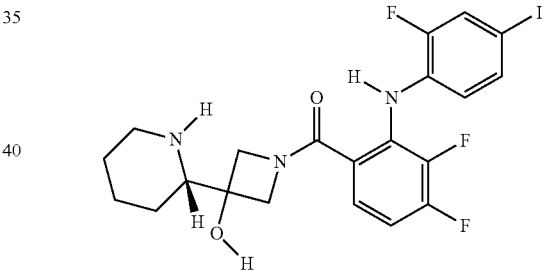

(S)-[3,4-Difluoro-2-(2-fluoro-4-iodophenylamino)phenyl]
[3-hydroxy-3-(piperidin-2-yl)azetidin-1-yl] methanone Binimetinib:

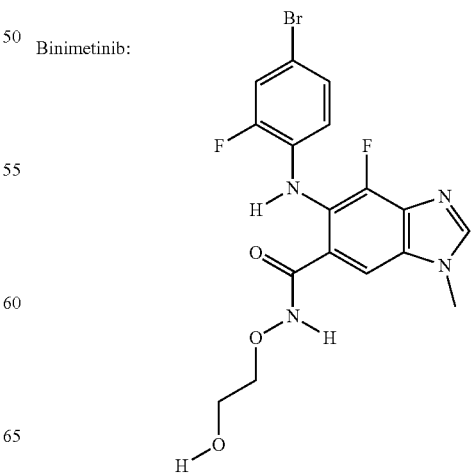

5-((4-bromo-2-fluorophenyl)amino)-4-fluoro-N-(2-hydroxyethoxy)-1-methyl-1H-benzo[d]imidazole-6-carboxamide Selumetinib:

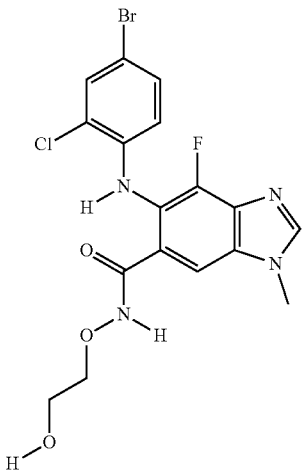

6-(4-bromo-2-chloroanilino)-7-fluoro-N-(2-hydroxyethoxy)-3-methylbenzimidazole-5-carboxamide.

Additional MAP2K1 (MEK1) inhibitors that can be used include PD-325901, CI-1040, PD035901 or TAK-933.

MEK1 and its paralog MEK2, phosphorylate ERK1 and ERK2. MAPK signaling is activated by receptor tyrosine kinases, integrins, and G-protein coupled receptors, and is modulated by cross-talk with several other signaling pathways including the AKT-mTOR pathway. The MAP2K1 mutations likely alter the function of MEK1 by producing a hypermorphic or neomorphic effect, since they have been shown to increase ERK1 and ERK2 phosphorylation in tumors and in cultured cells. Accordingly, in certain embodiments, an inhibitor of ERK1/2 phosphorylation is administered to a patient, comprising: SCH772984, LY3214996, SC1, RasGAP, VX-11e, DEL-22379, Ulixertinib (BVD-523, VRT752271), GDC-0994, FR 180204, ERK5-IN-1, or combinations thereof.

Inhibition of MAP2K1 (MEK1) by administration of inhibitory nucleic acids (e.g., dsRNAs, siRNAs, antisense oligonucleotides, etc.) is also explicitly contemplated. Nucleases, such as, CRISPR-Cas9 methods can also be used to excise and replace MAP2K1 alleles identified to carry a deleterious mutation. Such methods can be performed upon the cells of a subject in vivo or ex vivo. Use of any combination of the above and/or other known MEK1 inhibitors is also contemplated.

Nucleases

Methods of the invention may be used to remove mutated genetic material from a subject, without interfering with the integrity of the subject's genetic material. A nuclease may be used to specifically target MAP2K1 mutations in a subject, such as for example, Lys57As, Gln56Pro, Gln58_Glu62 del and/or Phe53Leu/Asp67Tyr which are excised by the nuclease. Targeting of the MAP2K1 mutations can be done using a sequence-specific moiety such as a guide DNA that targets MAP2K1 mutations for destruction by the nuclease and does not target the host cell genome. In some embodiments, a nuclease and guide DNA (gDNA) or guide RNA (gRNA) that together target and selectively edit or destroy MAP2K1 mutations is used. In certain embodiments, a delivery vehicle delivers a wild-type MAP2K1 polynucleotide, oligonucleotide, polypeptide or peptides thereof. The delivery vehicle can be specifically targeted to endothelial cells.

Any suitable nuclease systems can be used including, for example, Argonaute family of endonucleases, clustered regularly interspaced short palindromic repeat (CRISPR) nucleases, zinc-finger nucleases (ZFNs), transcription activator-like effector nucleases (TALENs), meganucleases, other endo- or exo-nucleases, or combinations thereof. See Schiffer, 2012, *J Virol* 88(17):8920-8936, incorporated by reference. In certain embodiments, the system is an Argonaute nuclease system.

In certain embodiments, a composition for excising an MAP2K1 mutation in vitro or in vivo, comprises an isolated nucleic acid sequence encoding an Argonaute endonuclease and at least one guide DNA (gDNA), guide RNA (gRNA), or combinations thereof, each guide nucleic acid sequence being complementary to a target nucleic acid sequence wherein the target nucleic acid sequence comprises one or more MAP2K1 mutations.

Argonautes are a family of endonucleases that use 5' phosphorylated short single-stranded nucleic acids as guides to cleave targets (Swarts, D. C. et al. The evolutionary journey of Argonaute proteins. *Nat. Struct. Mol. Biol.* 21, 743-753 (2014)). Similar to Cas9, Argonautes have key roles in gene expression repression and defense against foreign nucleic acids (Swarts, D. C. et al. *Nat. Struct. Mol. Biol.* 21, 743-753 (2014); Makarova, K. S., et al. *Biol. Direct* 4, 29 (2009). Molloy, S. *Nat. Rev. Microbiol.* 11, 743 (2013); Vogel, J. *Science* 344, 972-973 (2014). Swarts, D. C. et al. *Nature* 507, 258-261 (2014); Olovnikov, I., et al. *Mol. Cell* 51, 594-605 (2013)). However, Argonautes differ from Cas9 in many ways (Swarts, D. C. et al. The evolutionary journey of Argonaute proteins. *Nat. Struct. Mol. Biol.* 21, 743-753 (2014)). Cas9 only exist in prokaryotes, whereas Argonautes are preserved through evolution and exist in virtually all organisms; although most Argonautes associate with single-stranded (ss)RNAs and have a central role in RNA silencing, some Argonautes bind ssDNAs and cleave target DNAs (Swarts, D. C. et al. *Nature* 507, 258-261 (2014); Swarts, D. C. et al. *Nucleic Acids Res.* 43, 5120-5129 (2015)). Guide RNAs must have a 3' RNA-RNA hybridization structure for correct Cas9 binding, whereas no specific consensus secondary structure of guides is required for Argonaute binding; whereas Cas9 can only cleave a target upstream of a PAM, there is no specific sequence on targets required for Argonaute. Once Argonaute and guides bind, they affect the physicochemical characteristics of each other and work as a whole with kinetic properties more typical of nucleic-acid-binding proteins (Salomon, W. E., et al. *Cell* 162, 84-95 (2015)).

The useful features of NgAgo for genome editing include the following: (i) it has a low tolerance to guide-target mismatch. (ii) 5' phosphorylated short ssDNAs are rare in mammalian cells, which minimizes the possibility of cellular oligonucleotides misguiding NgAgo. (iii) NgAgo follows a 'one-guide-faithful' rule, that is, a guide can only be loaded when NgAgo protein is in the process of expression, and, once loaded, NgAgo cannot swap its gDNA with other free ssDNA at 37° C.

Accordingly, in certain embodiments, Argonaute endonucleases comprise those which associate with single stranded RNA (ssRNA) or single stranded DNA (ssDNA). In certain embodiments, the Argonaute is derived from *Natronobacterium gregoryi*. In other embodiments, the *Natronobacterium gregoryi* Argonaute (NgAgo) is a wild type NgAgo, a modified NgAgo, or a fragment of a wild type or modified NgAgo. The NgAgo can be modified to increase nucleic acid binding affinity and/or specificity, alter an enzymatic activity, and/or change another property of the protein.

Another nuclease that is contemplated is the CRISPR system. CRISPR (Clustered Regularly Interspaced Short Palindromic Repeats) is found in bacteria and is believed to protect the bacteria from phage infection. It has recently been used as a means to alter gene expression in eukaryotic DNA, but has not been proposed more broadly as a way to disrupt genomic material. Rather, it has been used to introduce insertions or deletions as a way of increasing or decreasing transcription in the DNA of a targeted cell or population of cells. See for example, Horvath et al., *Science* (2010) 327:167-170; Terns et al., *Current Opinion in Microbiology* (2011) 14:321-327; Bhaya et al., *Annu Rev Genet* (2011) 45:273-297; Wiedenheft et al., *Nature* (2012) 482: 331-338); Jinek M et al., *Science* (2012) 337:816-821; Cong L et al., *Science* (2013) 339:819-823; Jinek M et al., (2013) *eLife* 2:e00471; Mali P et al. (2013) *Science* 339:823-826; Qi L S et al. (2013) *Cell* 152:1173-1183; Gilbert L A et al. (2013) *Cell* 154:442-451; Yang H et al. (2013) *Cell* 154: 1370-1379; and Wang H et al. (2013) *Cell* 153:910-918).

CRISPR methodologies employ a nuclease, CRISPR-associated (Cas), that complexes with small RNAs as guides (gRNAs) to cleave DNA in a sequence-specific manner upstream of the protospacer adjacent motif (PAM) in any genomic location. CRISPR may use separate guide RNAs known as the crRNA and tracrRNA. These two separate RNAs have been combined into a single RNA to enable site-specific mammalian genome cutting through the design of a short guide RNA. Cas and guide RNA (gRNA) may be synthesized by known methods. Cas/guide-RNA (gRNA) uses a non-specific DNA cleavage protein Cas, and an RNA oligonucleotide to hybridize to target and recruit the Cas/gRNA complex. See Chang et al., 2013, *Cell Res.* 23:465-472; Hwang et al., 2013, *Nat. Biotechnol.* 31:227-229; Xiao et al., 2013, *Nucl. Acids Res.* 1-11.

Three types (I-III) of CRISPR systems have been identified. CRISPR clusters contain spacers, the sequences complementary to antecedent mobile elements. CRISPR clusters are transcribed and processed into mature CRISPR RNA (crRNA). In embodiments, the CRISPR/Cas system can be a type I, a type II, or a type III system. Non-limiting examples of suitable CRISPR/Cas proteins include Cas3, Cas4, Cas5, Cas5e (or CasD), Cas6, Cas6e, Cas6f, Cas7, Cas8a1, Cas8a2, Cas8b, Cas8c, Cas9, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cu1966.

In type II CRISPR systems, correct processing of pre-crRNA requires a trans-encoded small RNA (tracrRNA), endogenous nuclease 3 (rnc) and a Cas9 protein. The tracrRNA serves as a guide for nuclease 3-aided processing of pre-crRNA. Subsequently, Cas9/crRNA/tracrRNA endonucleolytically cleaves linear or circular dsDNA target complementary to the spacer. The target strand not complementary to crRNA is first cut endonucleolytically, then trimmed 3'-5' exonucleolytically. In nature, DNA-binding and cleavage typically requires protein and both RNA species. However, guide RNAs can be engineered so as to incorporate aspects of both the crRNA and tracrRNA into a single RNA molecule. (See, e.g., Jinek M., et al. 2012 *Science* 337:816-821 the entire contents of which is hereby incorporated by reference). The tracrRNA and spacer RNA together are often referred to as guide RNA, which is typically between 17 and 20 nucleotides in length. The two RNA species can be joined to form one hybrid RNA molecule referred to herein as "guide RNA" (gRNA). When complexed with CAS9, the CAS9-guide RNA complex will find and specifically cut the correct DNA targets. (Pennisi, E. 2013 *Science* 341 (6148): 833-836). Thus, reference herein to a gRNA "targeted to" a component, including a specific protein, of a genome refers to a CRISPR-Cas system gRNA that hybridizes with the specified target sequence, whereby the gRNA hybridizes to the targeted sequence and the CRISPR-associated Cas9 nuclease cleaves the targeted genomic material, e.g. MAP2K1 mutations.

In certain embodiments, the CRISPR/Cas proteins comprise at least one RNA recognition and/or RNA binding domain. RNA recognition and/or RNA binding domains interact with guide RNAs. CRISPR/Cas proteins can also comprise nuclease domains (i.e., DNase or RNase domains), DNA binding domains, helicase domains, RNase domains, protein-protein interaction domains, dimerization domains, as well as other domains.

In one embodiment, the RNA-guided endonuclease is derived from a type II CRISPR/Cas system. The CRISPR-associated endonuclease, Cas9, belongs to the type II CRISPR/Cas system and has strong endonuclease activity to cut target DNA. Cas9 is guided by a mature crRNA that contains about 20 base pairs (bp) of unique target sequence (called spacer) and a trans-activated small RNA (tracrRNA) that serves as a guide for ribonuclease III-aided processing of pre-crRNA. The crRNA:tracrRNA duplex directs Cas9 to target DNA via complementary base pairing between the spacer on the crRNA and the complementary sequence (called protospacer) on the target DNA. Cas9 recognizes a trinucleotide (NGG) protospacer adjacent motif (PAM) to specify the cut site (the $3^{rd}$ nucleotide from PAM). The crRNA and tracrRNA can be expressed separately or engineered into an artificial fusion small guide RNA (sgRNA) via a synthetic stem loop (AGAAAU) to mimic the natural crRNA/tracrRNA duplex. Such sgRNA, like shRNA, can be synthesized or in vitro transcribed for direct RNA transfection or expressed from U6 or H1-promoted RNA expression vector, although cleavage efficiencies of the artificial sgRNA are lower than those for systems with the crRNA and tracrRNA expressed separately.

In other embodiments. the CRISPR/Cas-like protein can be a wild type CRISPR/Cas protein, a modified CRISPR/Cas protein, or a fragment of a wild type or modified CRISPR/Cas protein. The CRISPR/Cas-like protein can be modified to increase nucleic acid binding affinity and/or specificity, alter an enzymatic activity, and/or change another property of the protein. For example, nuclease (i.e., DNase, RNase) domains of the CRISPR/Cas-like protein can be modified, deleted, or inactivated. Alternatively, the CRISPR/Cas-like protein can be truncated to remove domains that are not essential for the function of the fusion protein. The CRISPR/Cas-like protein can also be truncated or modified to optimize the activity of the effector domain of the fusion protein.

The CRISPR-associated endonuclease Cas9 nuclease can have a nucleotide sequence identical to the wild type *Streptococcus pyogenes* sequence. The CRISPR-associated endonuclease may be a sequence from other species, for example other *Streptococcus* species, such as thermophiles. The Cas9 nuclease sequence can be derived from other species including, but not limited to: *Nocardiopsis dassonvillei, Streptomyces pristinaespiralis, Streptomyces viridochromogenes, Streptomyces roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas sp., Crocosphaera watsonii, Cyanothece sp., Microcystis aeruginosa, Synechococcus sp., Acetohalobium arabaticum,*

*Ammonifex degensii, Caldicelulosiruptor becscii, Candidatus desulforudis, Clostridium botulinum, Clostridium difficle, Finegoldia magna, Natranaerobius thermophiles, Pelotomaculum thermopropionicum, Acidithiobacillus caldus, Acidithiobacillus ferrooxidans, Allochromatium vinosum, Marinobacter sp., Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc sp., Arthrospira maxima, Arthrospira platensis, Arthrospira sp., Lyngbya sp., Microcoleus chthonoplastes, Oscillatoria sp., Petrotoga mobilis, Thermosipho africanus,* or *Acaryochloris marina. Pseudomonas aeruginosa, Escherichia coli,* or other sequenced bacteria genomes and archaea, or other prokaryotic microorganisms may also be a source of the Cas9 sequence utilized in the embodiments disclosed herein.

In some embodiments, the CRISPR/Cas-like protein can be derived from a wild type Cas9 protein or fragment thereof. In other embodiments, the CRISPR/Cas-like protein can be derived from modified Cas9 protein. For example, the amino acid sequence of the Cas9 protein can be modified to alter one or more properties (e.g., nuclease activity, affinity, stability, etc.) of the protein. Alternatively, domains of the Cas9 protein not involved in RNA-guided cleavage can be eliminated from the protein such that the modified Cas9 protein is smaller than the wild type Cas9 protein.

The wild type *Streptococcus pyogenes* Cas9 sequence can be modified. The nucleic acid sequence can be codon optimized for efficient expression in mammalian cells, i.e., "humanized." sequence can be for example, the Cas9 nuclease sequence encoded by any of the expression vectors listed in Genbank accession numbers KM099231.1 GI:669193757; KM099232.1 GI:669193761; or KM099233.1 GI:669193765. Alternatively, the Cas9 nuclease sequence can be for example, the sequence contained within a commercially available vector such as PX330 or PX260 from Addgene (Cambridge, Mass.). In some embodiments, the Cas9 endonuclease can have an amino acid sequence that is a variant or a fragment of any of the Cas9 endonuclease sequences of Genbank accession numbers KM099231.1 GI:669193757; KM099232.1 GI:669193761; or KM099233.1 GI:669193765 or Cas9 amino acid sequence of PX330 or PX260 (Addgene, Cambridge, Mass.). The Cas9 nucleotide sequence can be modified to encode biologically active variants of Cas9, and these variants can have or can include, for example, an amino acid sequence that differs from a wild type Cas9 by virtue of containing one or more mutations (e.g., an addition, deletion, or substitution mutation or a combination of such mutations). One or more of the substitution mutations can be a substitution (e.g., a conservative amino acid substitution). For example, a biologically active variant of a Cas9 polypeptide can have an amino acid sequence with at least or about 50% sequence identity (e.g., at least or about 50%, 55%, 60%, 65%, 70%, 75%, 80%, 85%, 90%, 95%, 97%, 98%, or 99% sequence identity) to a wild type Cas9 polypeptide. Conservative amino acid substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. The amino acid residues in the Cas9 amino acid sequence can be non-naturally occurring amino acid residues. Naturally occurring amino acid residues include those naturally encoded by the genetic code as well as non-standard amino acids (e.g., amino acids having the D-configuration instead of the L-configuration). The present peptides can also include amino acid residues that are modified versions of standard residues (e.g. pyrolysine can be used in place of lysine and selenocysteine can be used in place of cysteine). Non-naturally occurring amino acid residues are those that have not been found in nature, but that conform to the basic formula of an amino acid and can be incorporated into a peptide. These include D-alloisoleucine(2R,3S)-2-amino-3-methylpentanoic acid and L-cyclopentyl glycine (S)-2-amino-2-cyclopentyl acetic acid. For other examples, one can consult textbooks or the worldwide web (a site currently maintained by the California Institute of Technology displays structures of non-natural amino acids that have been successfully incorporated into functional proteins).

Guide RNA sequences according to the present invention can be sense or anti-sense sequences. The guide RNA sequence generally includes a proto-spacer adjacent motif (PAM). The sequence of the PAM can vary depending upon the specificity requirements of the CRISPR endonuclease used. In the CRISPR-Cas system derived from *S. pyogenes*, the target DNA typically immediately precedes a 5'-NGG proto-spacer adjacent motif (PAM). Thus, for the *S. pyogenes* Cas9, the PAM sequence can be AGG, TGG, CGG or GGG. Other Cas9 orthologs may have different PAM specificities. For example, Cas9 from *S. thermophilus* requires 5'-NNAGAA for CRISPR 1 and 5'-NGGNG for CRISPR3 and *Neiseria meningitidis* requires 5'-NNNNGATT. The specific sequence of the guide RNA may vary, but, regardless of the sequence, useful guide RNA sequences will be those that minimize off-target effects while achieving high efficiency and complete ablation of MAP2K1 mutations. The length of the guide RNA sequence can vary from about 20 to about 60 or more nucleotides, for example about 20, about 21, about 22, about 23, about 24, about 25, about 26, about 27, about 28, about 29, about 30, about 31, about 32, about 33, about 34, about 35, about 36, about 37, about 38, about 39, about 40, about 45, about 50, about 55, about 60 or more nucleotides.

The guide RNA sequence can be configured as a single sequence or as a combination of one or more different sequences, e.g., a multiplex configuration. Multiplex configurations can include combinations of two, three, four, five, six, seven, eight, nine, ten, or more different guide RNAs. Accordingly, in some embodiments, a polynucleotide sequence encoding at least one gRNA may encode two distinct gRNA sequences. In other embodiments, one polynucleotide encodes for one gRNA; a second polynucleotide encodes for a second gRNA; a third polynucleotide encodes for a third gRNA, etc., wherein each gRNA is complementary to distinct sequences of a target nucleic acid sequence. In other embodiments, a polynucleotide sequence encodes for two or more distinct gRNA sequences. In other embodiments, a polynucleotide encodes multiple gRNA sequences having overlapping target nucleic acid sequences. The combinations of gRNAs encoded by the polynucleotides is limited only by the imagination of the user.

Delivery Vehicles

Delivery vehicles as used herein, include any types of molecules for delivery of the compositions embodied herein, both for in vitro or in vivo delivery. Examples, include, without limitation: expression vectors, nanoparticles, colloidal compositions, lipids, liposomes, nanosomes, carbohydrates, organic or inorganic compositions and the like.

Any suitable method can be used to deliver the compositions to the endothelial cells (EC) or tissues. For example, an MEK1 inhibitor, a nuclease or the gene encoding the nuclease may be delivered by injection, orally, or by hydrodynamic delivery. In certain embodiments, the nucleases, e.g. CRISPR/Cas, Argonautes etc., or the gene encoding the nuclease may be delivered to systematic circulation or may be delivered or otherwise localized to a specific tissue type. The nuclease or gene encoding the nuclease may be modified or programmed to be active under only certain conditions such as by using a tissue-specific promoter so that the encoded nuclease is preferentially or only transcribed in certain tissue types.

In some embodiments, a delivery vehicle is an expression vector, wherein the expression vector encodes a desired nucleic acid sequence. In certain embodiments, the vector comprises an isolated nucleic acid sequence encoding a Clustered Regularly Interspaced Short Palindromic Repeat (CRISPR)-associated endonuclease and at least one guide RNA (gRNA), the gRNA being complementary to a target nucleic acid sequence in subject's genome. In certain embodiments, the nuclease is a Cas9 endonuclease and a guide RNA that specifically targets a MAP2K1 mutation comprising Lys57Asn (n=8), Gln56Pro (n=4), Gln58_Glu62 del (n=2), Phe53Leu/Asp67Tyr, or combinations thereof. The Cas9 endonuclease and the guide RNA may be co-expressed in a host cell infected by a virus.

In some embodiments, the compositions of the invention can be formulated as a nanoparticle, for example, nanoparticles comprised of a core of high molecular weight linear polyethylenimine (LPEI) complexed with DNA and surrounded by a shell of polyethyleneglycol modified (PEGylated) low molecular weight LPEI. In some embodiments, the compositions can be formulated as a nanoparticle encapsulating the compositions embodied herein. L-PEI has been used to efficiently deliver genes in vivo into a wide range of organs such as lung, brain, pancreas, retina, bladder as well as tumor.

In some embodiments of the invention, liposomes are used to effectuate transfection into a cell or tissue. The pharmacology of a liposomal formulation of nucleic acid is largely determined by the extent to which the nucleic acid is encapsulated inside the liposome bilayer. Encapsulated nucleic acid is protected from nuclease degradation, while those merely associated with the surface of the liposome is not protected. Encapsulated nucleic acid shares the extended circulation lifetime and biodistribution of the intact liposome, while those that are surface associated adopt the pharmacology of naked nucleic acid once they disassociate from the liposome. Nucleic acids may be entrapped within liposomes with conventional passive loading technologies, such as ethanol drop method (as in SALP), reverse-phase evaporation method, and ethanol dilution method (as in SNALP).

Liposomal delivery systems provide stable formulation, provide improved pharmacokinetics, and a degree of 'passive' or 'physiological' targeting to tissues. Encapsulation of hydrophilic and hydrophobic materials, such as potential chemotherapy agents, are known. See for example U.S. Pat. No. 5,466,468 to Schneider, which discloses parenterally administrable liposome formulation comprising synthetic lipids; U.S. Pat. No. 5,580,571, to Hostetler et al. which discloses nucleoside analogues conjugated to phospholipids; U.S. Pat. No. 5,626,869 to Nyqvist, which discloses pharmaceutical compositions wherein the pharmaceutically active compound is heparin or a fragment thereof contained in a defined lipid system comprising at least one amphipathic and polar lipid component and at least one nonpolar lipid component.

Liposomes and polymerosomes can contain a plurality of solutions and compounds. In certain embodiments, the complexes of the invention are coupled to or encapsulated in polymersomes. As a class of artificial vesicles, polymersomes are tiny hollow spheres that enclose a solution, made using amphiphilic synthetic block copolymers to form the vesicle membrane. Common polymersomes contain an aqueous solution in their core and are useful for encapsulating and protecting sensitive molecules, such as drugs, enzymes, other proteins and peptides, and DNA and RNA fragments. The polymersome membrane provides a physical barrier that isolates the encapsulated material from external materials, such as those found in biological systems. Polymerosomes can be generated from double emulsions by known techniques, see Lorenceau et al., 2005, Generation of Polymerosomes from Double-Emulsions, Langmuir 21(20): 9183-6, incorporated by reference.

In some embodiments of the invention, non-viral vectors are modified to effectuate targeted delivery and transfection. PEGylation (i.e. modifying the surface with polyethyleneglycol) is the predominant method used to reduce the opsonization and aggregation of non-viral vectors and minimize the clearance by reticuloendothelial system, leading to a prolonged circulation lifetime after intravenous (i.v.) administration. PEGylated nanoparticles are therefore often referred as "stealth" nanoparticles.

Pharmaceutical Compositions

Certain aspects of the instant disclosure pertain to pharmaceutical compositions of the compounds of the disclosure. The pharmaceutical compositions of the disclosure typically comprise a compound of the instant disclosure and a pharmaceutically acceptable carrier. As used herein "pharmaceutically acceptable carrier" includes any and all solvents, dispersion media, coatings, antibacterial and antifungal agents, isotonic and absorption delaying agents, and the like that are physiologically compatible. The type of carrier can be selected based upon the intended route of administration. In various embodiments, the carrier is suitable for intravenous, intraperitoneal, subcutaneous, intramuscular, topical, transdermal or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the instant disclosure is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the compounds can be administered in a time release formulation, for example in a composition which includes a slow release polymer, or in a fat pad described herein. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are generally known to those skilled in the art.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, certain methods of preparation are vacuum drying and freeze-drying which yields a powder of the active ingredient plus any additional desired ingredient from a previously sterile-filtered solution thereof.

Depending on the route of administration, the compound may be coated in a material to protect it from the action of enzymes, acids and other natural conditions which may inactivate the agent. For example, the compound can be administered to a subject in an appropriate carrier or diluent co-administered with enzyme inhibitors or in an appropriate carrier such as liposomes. Pharmaceutically acceptable diluents include saline and aqueous buffer solutions. Enzyme inhibitors include pancreatic trypsin inhibitor, diisopropylfluoro-phosphate (DEP) and trasylol. Liposomes include water-in-oil-in-water emulsions as well as conventional liposomes (Strejan, et al., (1984) *J. Neuroimmunol* 7:27). Dispersions can also be prepared in glycerol, liquid polyethylene glycols, and mixtures thereof and in oils. Under ordinary conditions of storage and use, these preparations may contain a preservative to prevent the growth of microorganisms.

The active agent in the composition (i.e., MEK1 inhibitor) preferably is formulated in the composition in a therapeutically effective amount. A "therapeutically effective amount" refers to an amount effective, at dosages and for periods of time necessary, to achieve the desired therapeutic result to thereby influence the therapeutic course of a particular disease state. A therapeutically effective amount of an active agent may vary according to factors such as the disease state, age, sex, and weight of the individual, and the ability of the agent to elicit a desired response in the individual. Dosage regimens may be adjusted to provide the optimum therapeutic response. A therapeutically effective amount is also one in which any toxic or detrimental effects of the agent are outweighed by the therapeutically beneficial effects. In another embodiment, the active agent is formulated in the composition in a prophylactically effective amount. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The amount of active compound in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the instant disclosure are dictated by and directly dependent on (a) the unique characteristics of the active compound and the particular therapeutic effect to be achieved, and (b) the limitations inherent in the art of compounding such an active compound for the treatment of sensitivity in individuals.

Exemplary dosages of compounds (e.g., MEK1 inhibitor) of the instant disclosure include e.g., about 0.0001% to 5%, about 0.0001% to 1%, about 0.0001% to 0.1%, about 0.001% to 0.1%, about 0.005%-0.1%, about 0.01% to 0.1%, about 0.01% to 0.05% and about 0.05% to 0.1%.

The compound(s) of the instant disclosure can be administered in a manner that prolongs the duration of the bioavailability of the compound(s), increases the duration of action of the compound(s) and the release time frame of the compound by an amount selected from the group consisting of at least 3 hours, at least 6 hours, at least 12 hours, at least 24 hours, at least 48 hours, at least 72 hours, at least 4 days, at least 5 days, at least 6 days, at least 7 days, at least 2 weeks, at least 3 weeks, and at least a month, over that of the compound(s) in the absence of the duration-extending administration. Optionally, the duration of any or all of the preceding effects is extended by at least 30 minutes, at least an hour, at least 2 hours, at least 3 hours, at least 6 hours, at least 12 hours, at least 24 hours, at least 48 hours, at least 72 hours, at least 4 days, at least 5 days, at least 6 days, at least 7 days, at least 2 weeks, at least 3 weeks or at least a month.

A compound of the instant disclosure can be formulated into a pharmaceutical composition wherein the compound is the only active agent therein. Alternatively, the pharmaceutical composition can contain additional active agents. For example, two or more compounds of the instant disclosure may be used in combination. Moreover, a compound of the instant disclosure can be combined with one or more other agents that have modulatory effects on AVM.

Combination Therapies

MAP2K1 mutations in endothelial cells (ECs) indicate that MAP2K1 is important for angiogenesis. Endothelial proliferation, migration, and tube formation are dependent on ERK phosphorylation in ECs. Inhibition of MEK-ERK signaling causes EC apoptosis and retraction of sprouting tubules. Thus, the findings described in detail in the examples section that AVMs contain MAP2K1-activating mutations in resident ECs evidences that the mutation likely increases angiogenesis.

Accordingly in certain embodiments, a method of treatment comprises administration of one or anti-angiogenic agents. The anti-angiogenic agent may be administered together with the MEK1 inhibitors or at different times. In certain embodiments, the anti-angiogenic agent(s) is formulated with the pharmaceutical composition comprising one or more MEK1 inhibitors.

In certain embodiments, a pharmaceutical composition comprises a therapeutically effective amount of one or more MEK1 inhibitors and a pharmaceutically acceptable carrier. In certain embodiments, the pharmaceutical composition further comprises a therapeutically effective amount of one or more anti-angiogenic agents. In some embodiments, the one or more anti-angiogenic agents comprise sunitinib, angiostatin K1-3, arresten, DL-α-difluoromethyl-ornithine, fumagillin, genistein, staurosporine, (±)-thalidomide, tumstatin, axitinib, bortezomib, bosutinib gefitinib, pazopanib, semaxanib, sorafenib, vandetanib, vatalanib, canertinib, cilengitide, dovitinib, dasatinib, erlotinib, everolimus, imatinib, lapatinib, masutinib, marizomib, mubitinib, lestaurtinib, pazopanib, tandutinib, vismodegib or combinations thereof.

In certain embodiments, a subject is further treated with one or more one or more inhibitors of ERK1/2 phosphorylation. Accordingly, in certain embodiments, the pharmaceutical composition comprises one or more inhibitors of ERK1/2 phosphorylation comprising SCH772984, LY3214996, SC1, RasGAP, VX-11e, DEL-22379, Ulixertinib (BVD-523, VRT752271), GDC-0994, FR 180204, ERK5-IN-1, or combinations thereof Kits The instant disclosure also includes kits that include a composition of the instant disclosure, optionally also including a compound (e.g., a MEK1 inhibitor), and instructions for use.

This disclosure is further illustrated by the following examples which should not be construed as limiting. The contents of all references, patents, and published patent applications cited throughout this application, as well as the figures, are incorporated herein by reference.

EXAMPLES

Overview

AVMs are characteristically abnormal connections between arteries and veins that are missing normal high-resistance capillary beds (FIG. 1)[1]. Extracranial AVMs were studied to identify their biological basis. Whole-exome sequencing (WES) and whole-genome sequencing (WGS) were performed on AVM tissue obtained from affected individuals. Endothelial cells were separated from non-endothelial cells by immune-affinity purification. Droplet digital PCR (ddPCR) was then used to confirm mutations found by WES and WGS, to determine if mutant alleles were enriched in endothelial or non-endothelial cells, and to screen additional AVM specimens. WES and WGS detected in 7 of 10 specimens, and ddPCR confirmed, somatic mutations in mitogen activated protein kinase kinase 1 (MAP2K1; NM_002755), the gene that encodes MAP-extracellular signal-regulated kinase 1 (MEK1; NP_002746.1). Mutant alleles were enriched in endothelial cells and were not present in blood or saliva. Nine of 15 additional AVM specimens contained mutant MAP2K1 alleles. Identified mutations were missense or small in-frame deletions that affected amino acid residues within or adjacent to the protein's negative regulatory domain. Several of these mutations have been previously identified in cancers and were shown to increase MEM activity. To summarize the below findings, somatic mutations in MAP2K1 were identified as a common cause of extracranial AVM. Without wishing to be bound by theory, the likely mechanism for AVM development was endothelial cell dysfunction due to increased MEK1 activity. MEK1 inhibitors, which have been previously approved to treat several forms of cancer, were thereby newly identified as prophylactic or therapeutic agents for individuals with or at risk of developing extracranial AVM.

Example 1: Materials and Methods

Informed consent was obtained from study participants. AVM specimens were collected during a clinically-indicated procedure. Affected tissue was flash-frozen and stored at −80° C.; two tissue specimens were also processed to separate endothelial cells from other cell types. Cells were isolated as previously described[3]. Specimens were digested with collagenase A (Roche) and dispase (BD Biosciences), filtered through a 70-μm strainer, incubated with anti-cluster of differentiation 31 protein (anti-CD31) antibody that was conjugated to magnetic Dynabeads (Invitrogen) in order to separate endothelial from non-endothelial cells, and then cultured. CD31$^+$ cells were grown in endothelial cell growth medium and CD31$^-$ cells were cultured in mesenchymal stem cell growth medium (both from Lonza). DNA was extracted from frozen tissue, cells, and blood (considered unaffected tissue) using DNAeasy Blood & Tissue Kit (Qiagen). Saliva, also an unaffected tissue, was collected using Oragene Discover saliva kits (DNA Genotek) and DNA was extracted using the prepIT-L2P extraction kit (DNA Genotek).

Standard whole-exome sequencing (WES) was performed as previously described[4]. Deep WES and WGS were done by Macrogen on Illumina platforms using 101 basepair (bp) and 150 bp paired-end reads, respectively. Raw sequencing reads were aligned to the GRCh37 human reference genome using the Burrows-Wheeler Aligner[5]. The aligned reads were processed by Picard and the Genome Analysis Tool Kit[6] for the removal of duplicated and error-prone reads, indel realignment, and base-quality recalibration. Candidate somatic mutations were identified using the single-sample (when only AVM DNA was available) and paired-sample (when AVM and blood/saliva DNA were available) modes of MosaicHunter[7].

Somatic mutations with at least 2% mutant allele fraction and at least 5 reads supporting the variant allele were considered in subsequent analyses. Common variants that were annotated in the Single Nucleotide Polymorphism[8], 1000 Genomes Project[9], Exome Sequencing Project[10], or Exome Aggregation Consortium[11] databases were excluded. Among the protein-altering mutations, only those predicted to be deleterious by Polymorphism Phenotyping (PolyPhen2) or Sorting Intolerant From Tolerant (SIFT) algorithms[12,13] were analyzed further. Several specimens were found to contain somatic missense mutations in a single gene (MAP2K1). Therefore, the mutation-negative samples were reanalyzed by lowering the detection threshold to ≥1% mutant allele fraction and ≥3 reads supporting the variant allele, and short indels in addition to missense mutations in MAP2K1 were sought. This lower threshold was also employed for screening genes encoding other components in the RAt Sarcoma (RAS)/MAPK pathway.

Example 2: Confirmation and Quantitation of Mutant Allele Frequencies in Specimens ddPCR assays[14] were developed for each of the mutations identified by WES and WGS. These assays were used to confirm and quantify the mutant allele frequency in each specimen. When available, ddPCR was performed on participants' endothelial cells, non-endothelial cells, blood and saliva. Additional AVM specimens, which were not included in the initial WES or WGS studies, also were screened for mutations by ddPCR. When an alternative mutation was suspected because a pseudocluster (i.e., droplets exhibiting altered probe binding during target sequence amplification) was observed in the ddPCR assay, 100 amplimers from the target region were subcloned and Sanger sequenced. ddPCR assays were also performed using lesional DNA from other vascular anomalies, including infantile hemangioma, congenital hemangioma, capillary malformation, lymphatic malformation, venous malformation, and verrucous venous malformation.

Ten AVM specimens, including matched unaffected tissue specimens from 3 of the study participants, underwent deep WES yielding average on-target depths between 224-fold and 281-fold for the AVM samples and between 135-fold and 176-fold for the unaffected tissues. Coverage ≥30-fold and ≥90-fold were obtained for 90 to 93% and 81 to 92% of the exomes, respectively (FIG. 2). Five AVM specimens and 3 matched unaffected tissue specimens were subjected to WGS, yielding average depths between 108-fold and 145-fold for AVM tissue and 37-fold and 50-fold for unaffected tissue; all WGS specimens also underwent WES. AVMs had between 0 and 4 genes with putative protein-altering somatic mutations, but only MAP2K1, encoding the dual specificity mitogen-activated protein kinase MEK1, contained somatic mutations (p.K57N or p.Q56P) in multiple samples (Table 1). Each AVM sample had ≥105-fold coverage over the entire MAP2K1 coding sequence.

TABLE 1

MAP2K1 Variant Identification and Filtering for 10 AVM Samples Subjected to Deep Whole-Exome Sequencing

| | Participant | | | | | | | | | |
|---|---|---|---|---|---|---|---|---|---|---|
| | 2 | 3 | 6 | 12 | 15 | 18 | 20 | 22 | 23 | 25 |
| Somatic mosaic sites identified by MosaicHunter with ≥ 2% variant allele fraction and ≥ 5 variant reads | 34 | 32 | 24 | 14 | 21 | 15 | 22 | 33 | 38 | 63 |
| Considering only variants not present in the general population | 7 | 6 | 9 | 3 | 3 | 3 | 2 | 8 | 2 | 43 |
| Considering only non-synonymous mutations | 2 | 0 | 1 | 1 | 0 | 1 | 0 | 1 | 2 | 7 |
| Considering only mutations predicted to be defeterious | 2 | 0 | 1 | 1 | 0 | 1 | 0 | 0 | 2 | 4 |
| Genes harboring variants found with the above criteria | PALM2-AKAP2, HAUS7 | N/A | MAP2K1 | MAP2K1 | N/A | MAP2K1 | N/A | N/A | MAP2K1, EPPK1 | ZBTB41, OR8B8, FREM2, ACADVL |
| MAP2K1 mutation containing samples found using initial or less stringent criteria (variant/total WES reads) | p.Q58_E62def (10/493) | — | p.K57N (13/646) | p.Q56P 45/625 | — | p.K57N (17/529) | p.K57N (9/584) | p.K57N (6/583) | p.Q56P (21/611) | — |

Figure 3A:
FIGS. 3A to 3C show AVM endothelial cells enriched for the MAP2K1 mutation.
Figure 3B:
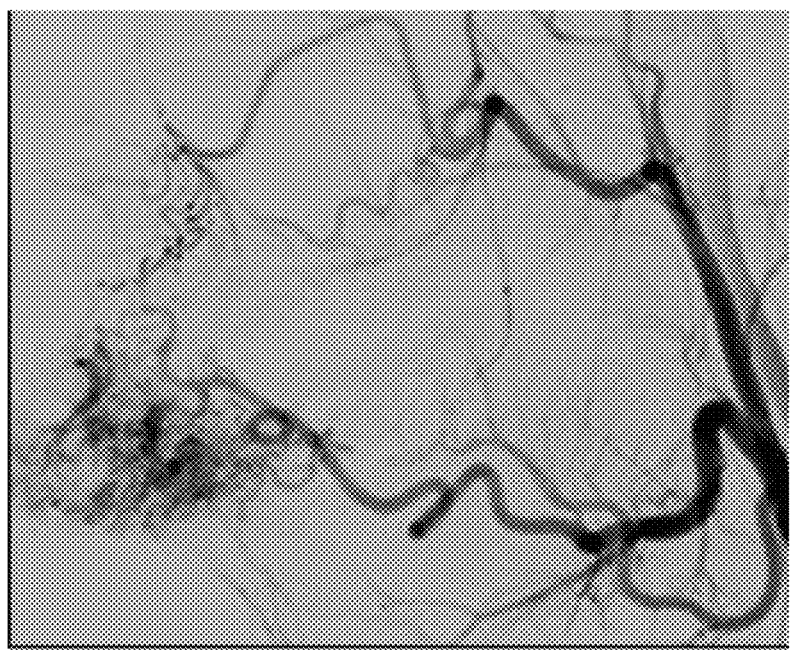
Figure 3C:
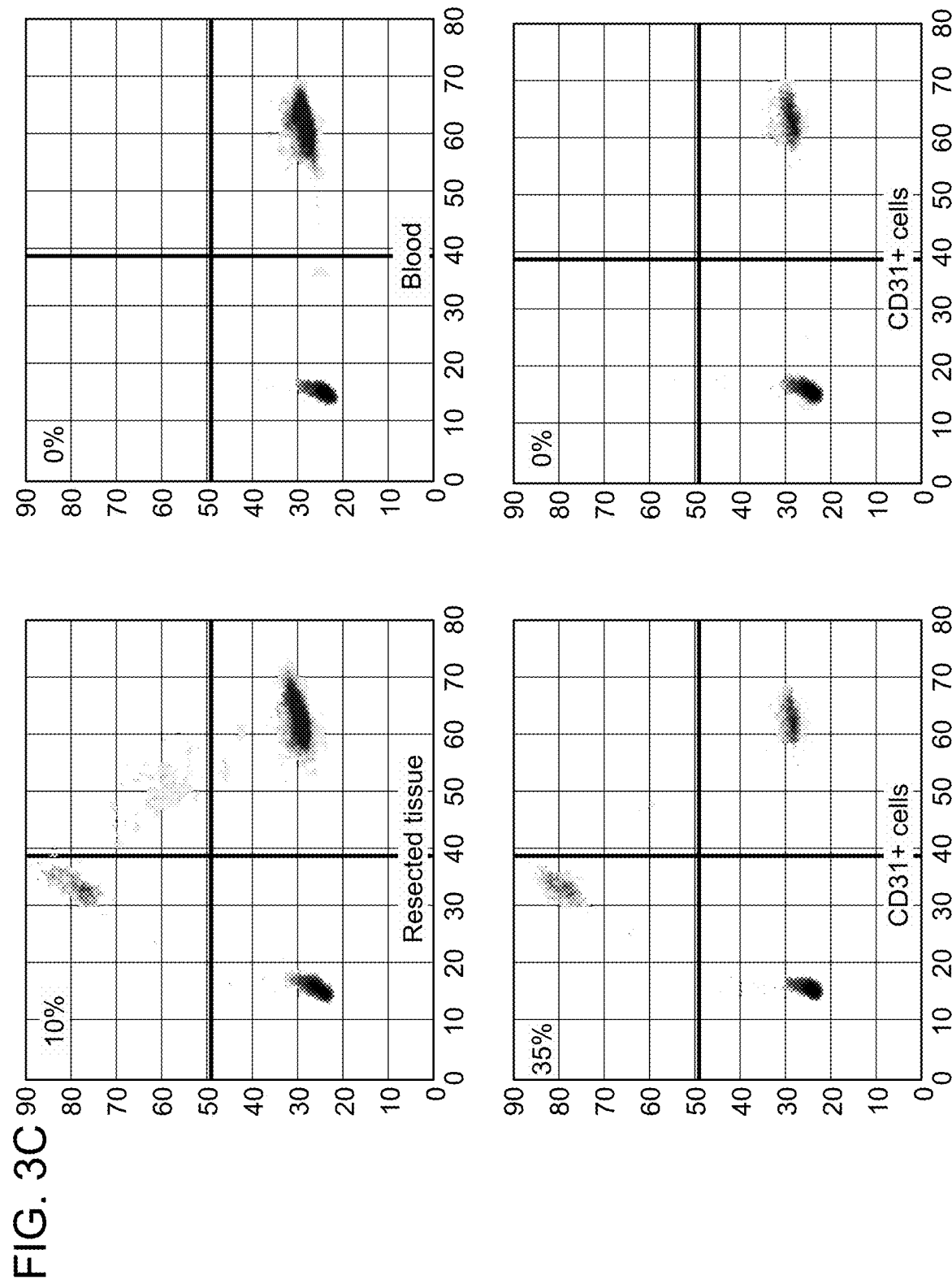
Figure 4:
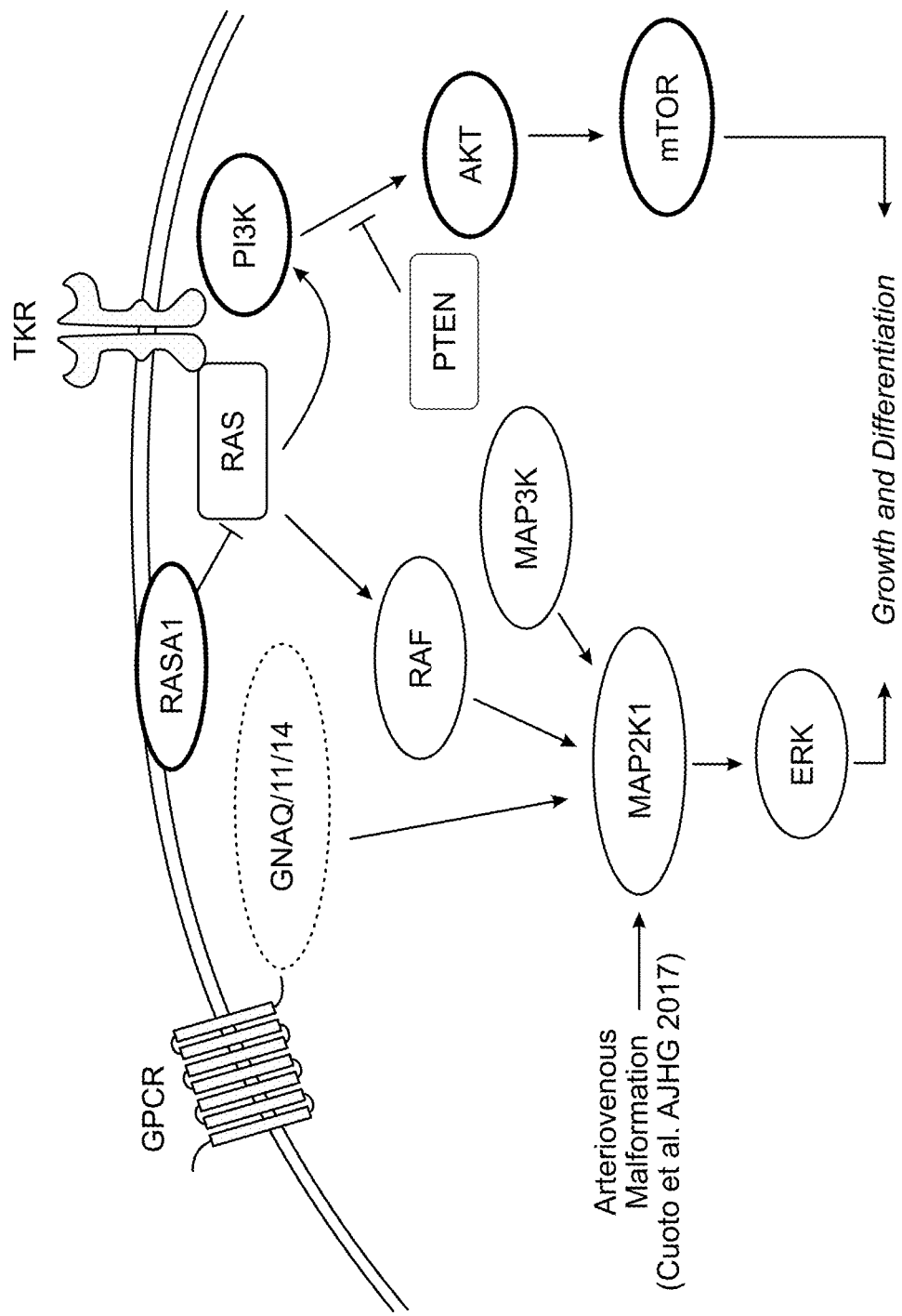
FIG. 4 is a schematic illustration showing the MAP2K1 signaling pathway.

After adjusting filtering criteria for the WES and WGS data to increase the sensitivity of detecting somatic MAP2K1 mutations by looking for indels and for mutant allele frequencies <2%, 3 additional samples subjected to deep WES were found to have MAP2K1 mutations (p.K57N [n=2], p.Q58_E62del [n=1]) (Table 1). Another AVM specimen that had undergone standard WES harbored 2 somatic MAP2K1 mutations p.F53L and p.D67Y in cis.

ddPCR was used to confirm the MAP2K1 mutations found in deep WES (n=7). ddPCR was also used to screen for somatic mutations in 15 additional individuals (3 without mutations detected by deep WES, 5 without mutations detected by standard WES, and 10 who had not been previously examined). Nine out of these 15 individuals had MAP2K1 mutations detected by ddPCR. One person had a ddPCR pseudocluster that upon subcloning and sequencing was found to represent the same 15-bp deletion (p.Q58_E62del) that was previously detected by WES in another individual. Additionally, in 3 of the affected tissue specimens that had endothelial cells separated from non-endothelial cells, mutant MAP2K1 alleles were only present in the endothelial cells (FIG. 3 and Table 2).

TABLE 2

MAP2K1 Mutaltion Detection in 25 Participants with AVM

| Participant | Age | Sex | Location Stage | DNA Source[a] | Mutation[b] | WES[c] | WGS[c] | ddPCR[d,e] |
|---|---|---|---|---|---|---|---|---|
| 1 | 5 yo | M | Lip Stage II | Frozen | Q56P | 7% 3/45 | — | 11% 231/2628 |
| | 6 yo | | | Frozen | Q56P | — | — | 2% 49/2764 |
| | | | | Saliva | nd | — | — | 0% 0/931 |
| 2 | 7 yo | M | Scalp Stage III | Frozen | Q58_E62del | 2% 10/493 | 3% 2/58 | 6%[f] 954/15592 |
| | | | | Saliva | nd | — | — | 0% 0/1745 |
| 3 | 9 yo | F | Thigh Stage III | Frozen | nd | 0% 0/633 | 0% 0/68 | 0% 0/4828 |
| | | | | Blood | nd | 0% 1/348[g] | 0% 0/31 | 0% 0/5006 |
| 4 | 9 yo | M | Forehead Stage II | Frozen | K57N | — | — | 0% 138/2654 |
| | | | | Blood | nd | — | — | 0% 0/2062 |
| 5 | 11 yo | F | Cheek Stage II | Frozen | K57N | — | — | 5% 124/3445 |
| | | | | Frozen | K57N | — | — | 8% 105/1379 |
| | | | | CD31+ Cells[a], p 3 | K57N | — | — | 31% 187/437 |

TABLE 2-continued

MAP2K1 Mutaltion Detection in 25 Participants with AVM

| Participant | Age | Sex | Location Stage | DNA Source[a] | Mutation[b] | WES[c] | WGS[c] | ddPCR[d,e] |
|---|---|---|---|---|---|---|---|---|
| | | | | CD31⁻ Cells[a], p 3 | nd | — | — | 0% 0/624 |
| | | | | Saliva | nd | — | — | 0% 0/1274 |
| 6 | 11 yo | M | Ear Stage I | Frozen | K57N | 2% 13/646 | — | 8% 157/2208 |
| | | | | Blood | nd | 0% 0/271 | 0% 0/35 | 0% 0/6913 |
| 7 | 12 yo | F | Cheek Stage II | Frozen | nd | 0% 0/37 | — | 0% 0/3207 |
| | | | | Saliva | nd | — | — | 0% 0/4085 |
| 8 | 12 yo | F | Ear Stage I | Frozen | K57N | 4% 2/52 | — | 13% 414/3498 |
| | | | | Saliva | nd | — | — | 0% 0/965 |
| 9 | 13 yo | M | Foot Stage III | Frozen | nd | — | — | 0% 0/2461 |
| | | | | Saliva | nd | — | — | 0% 0/1926 |
| 10 | 13 yo | F | Lip Stage II | Frozen | K57N | — | — | 7% 172/3117 |
| | | | | Saliva | nd | — | — | 0% 0/533 |
| 11 | 13 yo | M | Forehead Stage II | Frozen | K57N | — | — | 4% 68/2066 |
| | | | | Blood | nd | — | — | 0% 0/3698 |
| 12 | 14 yo | F | Lip Stage I | Frozen | Q56P | 7% 45/625 | — | 9% 210/2334 |
| 13 | 14 yo | F | Lip Stage II | Frozen | Q56P | — | — | 8% 172/2980 |
| | | | | Frozen | Q56P | — | — | 6% 102/1821 |
| | | | | Frozen | Q56P | — | — | 10% 209/2655 |
| | | | | CD31⁺ Cells[a], p 5 | Q56P | — | — | 35% 175/514 |
| | | | | CD31⁻ Cells[a], p 2 | Q56P | — | — | 0% 0/563 |
| | | | | Blood | nd | — | — | 0% 0/2396 |
| 14 | 15 yo | M | Knee Stage I | Frozen | Q58_E62del | — | — | 10%[e] 1336/12887 |
| 15 | 15 yo | M | Cheek Stage III | Frozen | nd | 0% 0/675 | 0% 0/143 | 0% 0/3708 |
| 16 | 17 yo | M | Forehead Stage II | Frozen | nd | — | — | 0% 0/4025 |
| | | | | Saliva | nd | — | — | 0% 0/1396 |
| 17 | 18 yo | F | Lip Stage II | Frozen | nd | 0% 0/30 | — | 0% 0/3757 |
| | | | | Saliva | nd | — | — | 0% 0/2458 |
| 18 | 21 yo | M | Ear Stage II | Frozen | K57N | 3% 17/529 | 4% 3/69 | 7% 155/2559 |
| | | | | CD31⁺ Cells[a], p 4 | K57N | — | — | 53% 468/946 |
| | | | | CD31⁻ Cells[a], p 4 | nd | — | — | 0% 0/765 |
| | | | | Blood | nd | 0% 0/250 | 0% 0/25 | 0% 0/3681 |
| 19 | 22 yo | M | Abdomen Stage II | Frozen | F53L | 5% 6/134 | — | 1% 9/1318 |
| | | | | | D67Y | 5% 10/203 | — | 1% 7/1336 |
| | | | | Blood | nd | 0% 0/15 | — | — |

TABLE 2-continued

MAP2K1 Mutaltion Detection in 25 Participants with AVM

| Participant | Age | Sex | Location Stage | DNA Source[a] | Mutation[b] | WES[c] | WGS[c] | ddPCR[d,e] |
|---|---|---|---|---|---|---|---|---|
| 20 | 22 yo | M | Scalp Stage I | Frozen | K57N | 2% 9/584 | — | 4% 63/2660 |
|  |  |  |  | Blood | nd | — | — | 0% 0/3171 |
| 21 | 23 yo | M | Face Stage III | Frozen | nd | — | — | 0% 0/4061 |
| 22 | 24 yo | M | Cheek Stage I | Frozen | K57N | 1% 6/583 | — | 5% 100/2531 |
|  |  |  |  | Saliva | nd | — | — | 0% 0/807 |
| 23 | 32 yo | M | Cheek Stage III | Frozen | Q56P | 3% 21/611 | 4% 2/47 | 7% 128/2103 |
|  |  |  |  | Saliva | nd | — | — | 0% 0/1494 |
| 24 | 39 yo | F | Scalp Stage III | Frozen | nd | — | — | 0% 0/3640 |
| 25 | 65 yo | F | Nose Stage II | Frozen | nd | 0% 0/656 | — | 0% 0/2642 |
|  |  |  |  | Saliva | nd | — | — | 0% 0/1325 |

[a]For cultured CD31$^+$ and CD31$^-$ cells, the passage number (p) at the time DNA was extracted in indicated.
[b]The effect of the mutation at the protein level is indicated.
[c]Mutant allele percentages are provided as whole numbers and are calculated from the number of mutant reads/total reads at that locus.
[d]Mutant allele percentages are provided as whole numbers and are calculated by counting droplets that contain mutant, mutant + wild type, and wild – type amplimers. For simplicity, the ratio of mutant amplimer containing droplets/all amplimer containing droplets is shown.
[e]When no MAP2K1 mutation was detected in affected tissue, the denominator for the ddPCR assay is the sum of WT droplets for the 4 individual assays.
[f]Because no ddPCR assay was developed for this mutation, the mutant allele percentages were determined using pseudocluster counts, which were observed with each of the other missense mutant ddPCR probes.
[g]This variant (p.D67Y) cannot be precluded from being a true positive somatic mutation; however this variant was not detected in 3,867 DNA containing ddPCR droplets from affected tissue, nor in ddPCR droplets from the same blood sample. Therefore, the WES result is likely a false positive finding.
"nd" indicates no mutant alleles were detected.
"—" indicates no study was performed.

In 13 participants who had affected tissue that contained a MAP2K1 mutation and a paired unaffected. tissue sample studied by ddPCR, none of the unaffected tissue samples contained mutant MAP2K1 alleles. No mutant MAP2K1 alleles were identified in affected tissue from individuals possessing other types of vascular anomalies. Three AVM specimens that had WES did not have a detectable MAP2K1 mutation. DNA sequence from these specimens was therefore re-examined at reduced stringency for mutations in other RAS/MAPK signaling pathway components (HRAS, KRAS, ARAF, BRAF, RAF1, MAP2K2, MAPK1, and MAPK3) as well as for previously reported AVM-associated genes (RASA, PTEN, ENG, ACVRL1, SMAD4, GDF). No suspicious somatic mutations were found.

CONCLUSION

The most common type of AVM occurs sporadically and is solitary. The prevalence of AVMs is unknown. The Vascular Anomalies Center at Boston Children's Hospital annually evaluates ~50 new patients with extracranial AVM[15]. Solitary, extracranial AVM is not heritable, has similar incidence in males and females, and exhibits variable severity. These features are typical of disorders caused by a somatic mutation[16] and are consistent with the finding of somatic MAP2K1 mutations in 16 of 25 tissue specimens. Solitary AVMs progress through 4 clinical stages: stage I lesions are typically small, warm to the touch, and exhibit arteriovenous shunting by Doppler ultrasonography. Stage II lesions enlarge significantly, become pulsatile, and develop venous dilatation. Stage III AVMs exhibit pain, ulceration, and/or bleeding. Stage IV lesions are characterized by cardiac failure[2,17]. The possibility that somatic MAP2K1 mutations arise as a consequence of AVM expansion, rather than being the cause of AVM cannot be excluded. Arguing against the former interpretation is the presence of mutations in stage I lesions (FIG. 1 and Table 2) and the absence of mutations in other enlarging vascular malformations. The instant discovery of MAP2K1 mutations solely within the endothelial cells strongly suggested this cell type was responsible for the malformation process. Mutated endothelial cells may have been unable to form a capillary network between developing arteries and veins, resulting in the AVM phenotype.

MAP2K1 mutations were identified in 64% of the AVM specimens examined; the remaining samples may have contained mutations at levels below the detection limit, in regions of the gene not interrogated by ddPCR, or in other genes. AVMs also occur in individuals segregating three Mendelian genetic diseases; however, these AVMs are clinically, radiologically, and/or histologically distinct from AVMs possessing MAP2K1 mutations. AVMs associated with hereditary hemorrhagic telangiectasia (HHT [MIM: 187300, 175050, 600376]), caused by mutations in ENG, ACVRL1, SMAD4, or GDF, have been described as multifocal, small, and affecting lungs, gastrointestinal system, and brain[18]. Families segregating RASA1 mutations have capillary malformation-arteriovenous malformation (CM-AVM [MIM: 608354]). This syndrome is characterized by multiple, small, cutaneous fast-flow lesions; some patients also have intracranial or extracranial AVMs[19]. Multiple, intramuscular AVMs have been shown to occur in patients with phosphatase and tensin homolog (PTEN) hamartoma-tumor syndrome [MIM: 601728][20].

The MAP2K1 protein product MEK1 plays an important role in the RAS/MAPK signaling pathway that controls numerous cellular and developmental processes[21,22]. The somatic mutations identified herein clustered within or adjacent to the protein's negative regulatory domain (FIG. 2); they have previously been observed in neoplasms, including melanoma, lung cancer, and hematopoietic malignancies[23-28], and have been shown to constitutively increase MEK1 activity[29-31]. MEK1 and its paralog MEK2, phosphorylate ERK1 and ERK2. MAPK signaling is activated by receptor tyrosine kinases, integrins, and G-protein coupled receptors, and is modulated by cross-talk with several other signaling pathways including the AKT-mTOR pathway[22]. Somatic mutations affecting proteins upstream of MEK1 occur in cancer and other types of vascular malformations[4,22,32-37]. Without wishing to be bound by theory, the MAP2K1 mutations detected herein in AVMs likely altered the function of MEK1 by producing a hypermorphic or neomorphic effect, since these mutations have previously been shown to increase ERK1 and ERK2 phosphorylation in tumors and in cultured cells. Consistent with this hypothesis, mice that were heterozygous for Mek1 knockout alleles did not exhibit a phenotype, whereas homozygous knockout alleles caused embryonic lethality and placental defects[38]. Germline mutations in MAP2K1 have previously been found in persons with Noonan Syndrome (NS [MIM: 163950])[39] and cardio-facio-cutaneous syndrome (CFC [MIM: 115150])[40]. However, individuals with NS or CFC exhibit cardiac malformations, including pulmonic stenosis and atrial septal defect, but not AVM[41,42]. The MAP2K1 mutations detected herein in AVMs differed from those found in NS and CFC.

The AVMs in which MAP2K1 mutations were found did not metastasize, but they enlarged over time[43]. Incompletely resected AVMs often re-expanded and attempts to embolize or ligate feeding arteries resulted in increased flow from collateral vessels[2]. Various MEK1 inhibitors are currently are in use against various cancers[21]. These drugs are likely to have therapeutic or even prophylactic efficacy for AVM. Current agents are cytostatic rather than cytotoxic, but are likely to benefit individuals with AVM if they cause mutant endothelial cells to terminally differentiate into capillary beds or prevent the regrowth of AVMs after resection or embolization.

Example 3: The Spectrum of Somatic Mutations that Cause Human AVMs

Although no published studies have examined the effects of MAP2K1 mutations in ECs, MAP2K1 is important for angiogenesis. Endothelial proliferation, migration, and tube formation are dependent on ERK phosphorylation in ECs. Inhibition of MEK-ERK signaling causes EC apoptosis and retraction of sprouting tubules. Thus, the finding herein that AVMs contain MAP2K1-activating mutations in resident ECs provides evidence that the mutation likely increases angiogenesis. Hyperproliferation and migration of ECs may dysregulate the recruitment of pericytes required for stable blood vessel formation. Consequently, irregular vasculature develops with abnormal connections between arteries and veins through a nidus or fistula. Because of the absence of a capillary bed, local hypoxia could further stimulate the system because hypoxia increases MEK-ERK signaling. This worsening cycle of abnormal blood vessel production and hypoxia may be responsible for the progression of AVMs.

Figure 5:
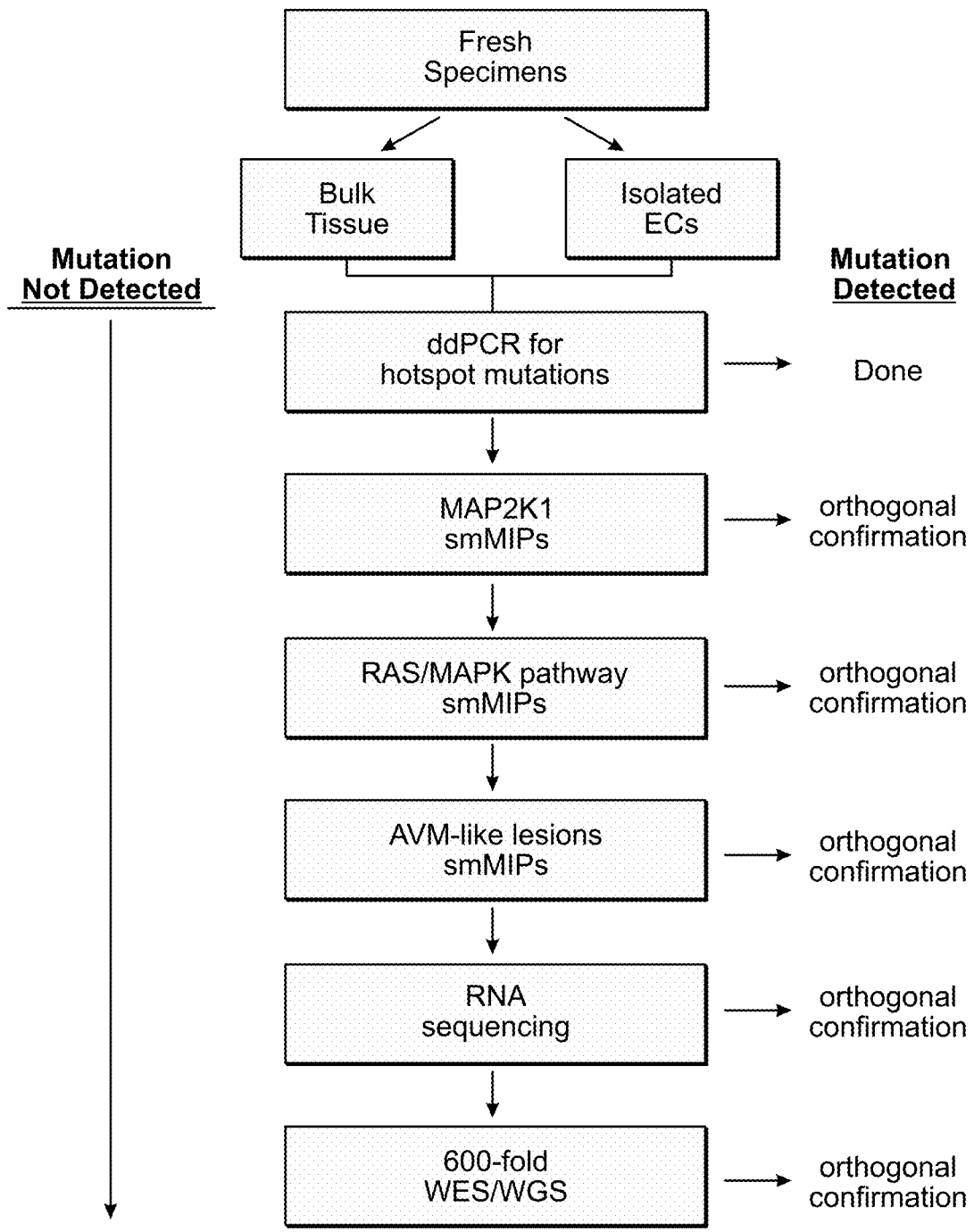
FIG. 5 is a flow diagram showing an embodiment of a method for somatic mutation discovery in extracranial AVMs.
Figure 6C:
FIGS. 6A-6E show the discovery of a somatic HRAS mutation (p.Thr58_Ala59delinsValLeuAspVal) in an MAP2K1-negative specimen.
Figure 6B:
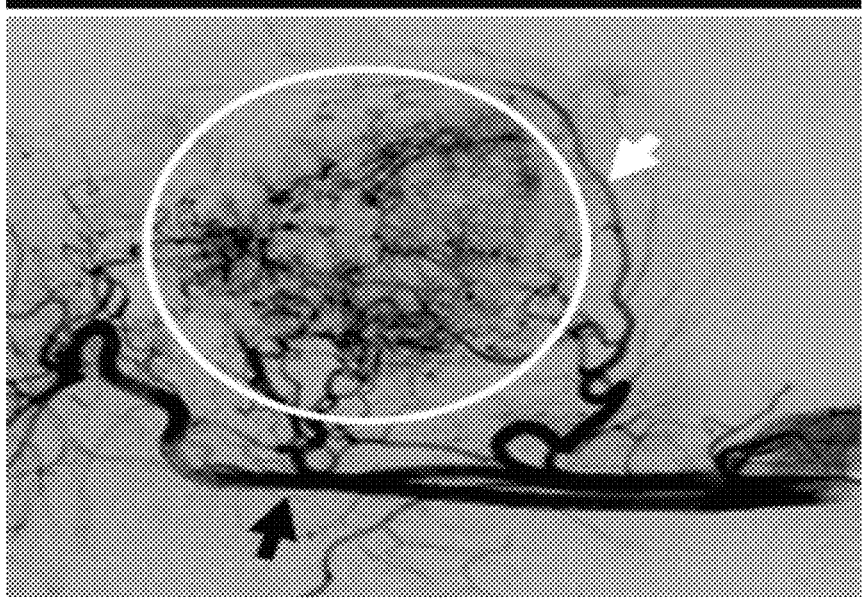
Figure 6A:
Figure 6D:
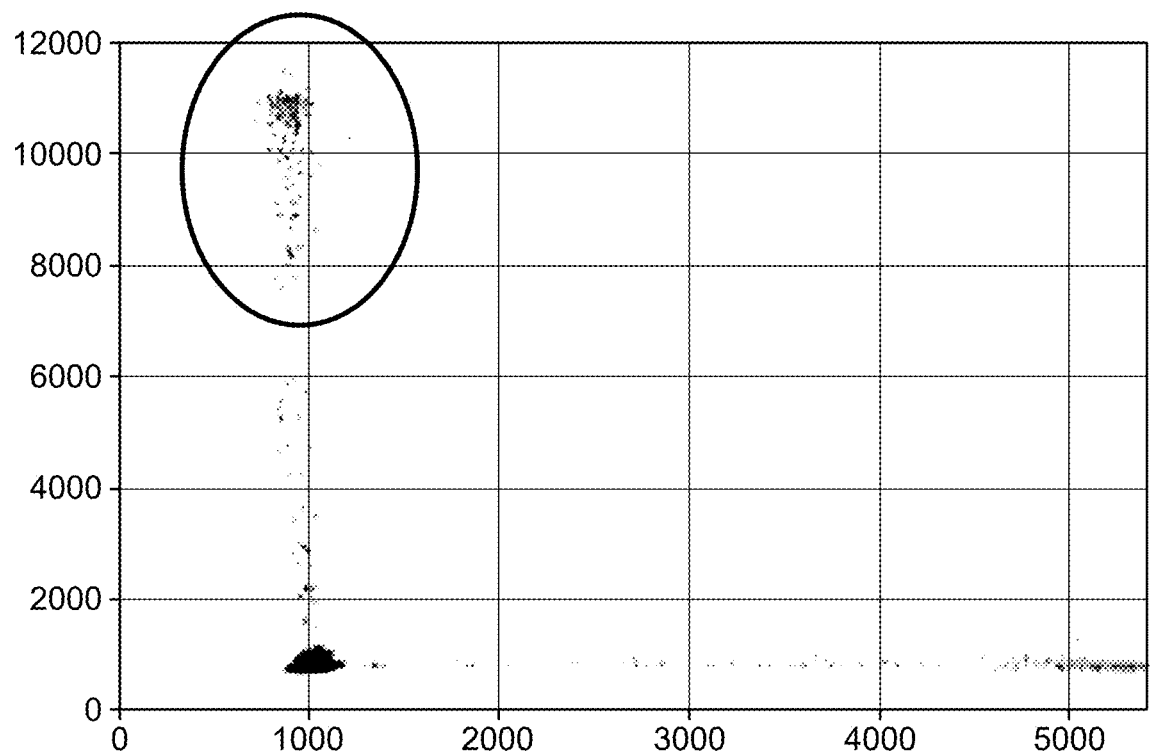
Figure 6E:
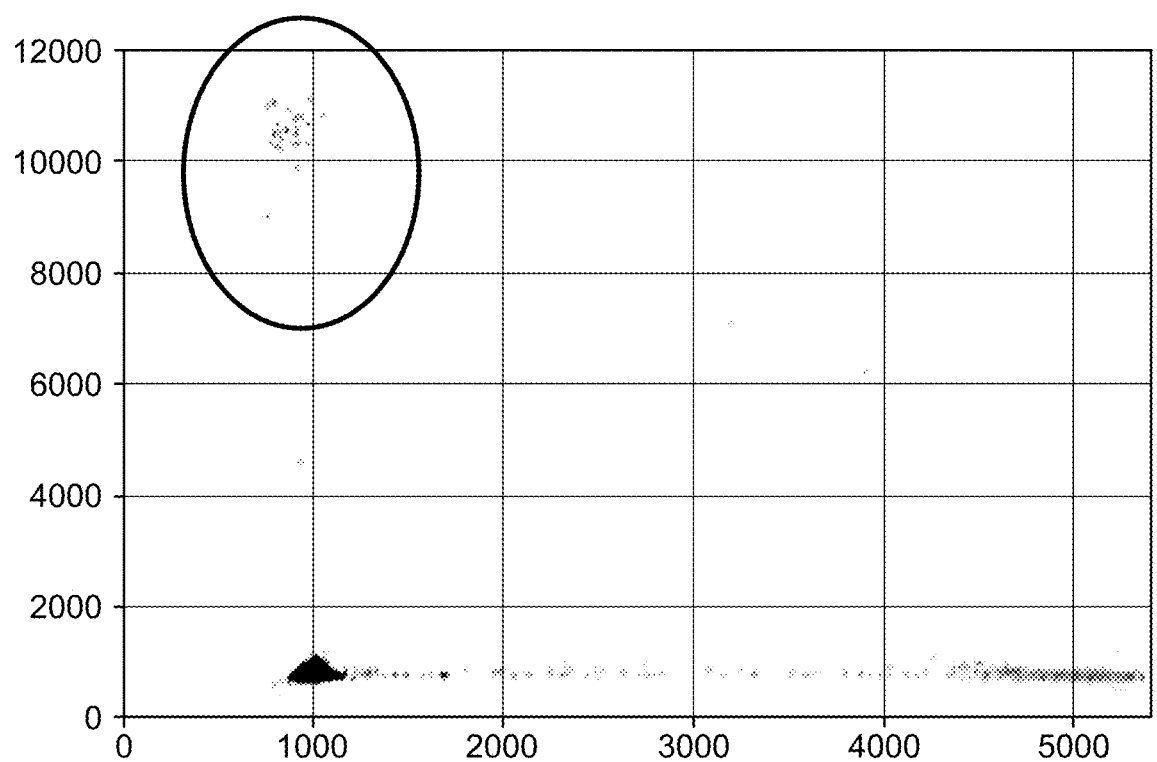

Detectable mutations were found in 16 or 25 AVM specimens that were studied; the 9 samples without a detectable mutation provide an opportunity to further understand the etiology of AVM. Possible reasons a specimen did not exhibit a mutation include: (1) it contained a MAP2K1 mutation at a level below our detection limit, (2) a MAP2K1 mutation was present but affected an amino acid residue not queried by our ddPCR assay, or (3) the AVM was caused by a mutation in another gene. Without wishing to be bound by theory, it was hypothesized that it is most likely that mutations in genes other than MAP2K1 also cause human AVMs. For example, it was found that somatic GNAQ or GNA11 mutations can cause capillary malformations (when residue p.183 is affected in either protein) and congenital hemangiomas (when residue p.209 is affected in either protein). Venous malformations can be caused by mutations in TIE2, PIK3CA, or MAP3K3. It was hypothesized that some patients with AVMs will have somatic mutations in genes other than MAP2K1. It is also possible that these other genes will encode proteins that participate upstream or downstream of MEK1 in the MAPK signaling cascade. Accordingly, the aim was to identify somatic mutations in AVM samples without identifiable MAP2K1 using the strategies shown in FIG. 5.

AVM is locus heterogeneous. A somatic HRAS mutation (compound in-frame somatic indel: p.Thr58_Ala59delinsValLeuAspVal) was identified by performing WES on isolated ECs from an AVM that was MAP2K1-negative (FIGS. 7A-7E). HRAS is located upstream of MAP2K1 in its signaling pathway. Interestingly, the patient's AVM was associated with more adipose tissue than MAP2K1-associated AVMs, providing evidence that a genotype-phenotype relationship may exist with AVMs, similar to other types of vascular anomalies. For example, diffuse capillary malformations causing overgrowth of an extremity are associated with GNA11 mutations, while capillary malformations in other parts of the body are caused by GNAQ mutations.

Molecular Inversion Probe Sequencing (MIPseq)

The inventors have 8 frozen affected tissues without an identifiable MAP2K1 mutation and expect that 2/6 fresh specimens collected annually will not have a detectable mutation based on previous data that 1/3 of samples do not contain a MAP2K1 mutation. Approximately 100 archived AVM paraffin blocks are also available in the Department of Pathology and the Vascular Anomalies Center consults on ~20 new patients year with AVM scheduled to undergo resection of their AVM elsewhere. Samples that do not have one of the 5 previously identified MAP2K1 mutations by ddPCR will be screened using single molecule molecular inversion probes (smMIPs). Advantages of using smMIP probes are that they can reliably detect mutant allele frequencies of 0.5% and screen the entire MAP2K1 coding sequence. They contain bar-codes which reduce false positive results caused by the PCR-amplification step used for smMIP-sequencing library preparation or by DNA mutations created during formalin-fixation or long-term storage of archived specimens. If no mutations are found in the entire MAP2K1 gene then smMIPs are utilized to search for mutations in other genes in the RAS/MAPK pathway (HRAS, KRAS, NRAS, ARAF, BRAF, RAF1, MAP2K2, MAPK1, MAPK3, MAP3K3), as well as for genes that cause lesions which can resemble AVM (RASA, PTEN, ENG, ACVRL1, SMAD4, and GDF2). The advantage of a targeted screen using pooled smMIPs that simultaneously cover multiple genes is that it obtains deep coverage (>600-fold) at reasonable cost. Another benefit of smMIP sequencing is that it can enables identification of exon deletion/duplication mutations in genes, such as RASA1 and PTEN, which normally cause disease due to a loss-of-function. Patient-matched unaffected tissues (white blood cell DNA) are used as control samples.

RNA-Sequencing (RNAseq)

Fresh or frozen AVM specimens that still lack an identifiable mutation following ddPCR and MIP-seq are subjected to RNAseq to obtain 100 million reads. RNAseq permits the detection of missense mutations or small insertion/deletions mutations, even if they are expressed at low frequency in affected tissue. This approach was successfully used to find somatic GNAQ and GNA11 mutations in congenital hemangiomas and capillary malformations. RNAseq also allows for identifying splicing mutations in the aforementioned candidate genes and in all genes that are expressed (RPKM>2) in affected tissue. Finally, RNAseq can detect somatic mutations that produce chimeric RNA transcripts (i.e., fusions transcripts that result from a somatic chromosomal rearrangement). It was previously shown that the mutant allele frequency is higher in RNA which facilitates identification of somatic mutations. Patient-matched unaffected tissue (white blood cell DNA) are used as control tissue.

Sequencing of Isolated Cell Populations

It was found that MAP2K1 mutations were significantly more enriched in AVM-derived endothelial cells (ECs) (31%-53%) compared to whole AVM tissue (1%-13%). Because the mutant allele frequency is elevated in ECs, identification of somatic mutations in these cells is greatly facilitated. It is expected to prospectively obtain additional ECs from at least 2 MAP2K1-negative AVM specimens each year. ECs are isolated from fresh human AVM tissue obtained from the operating room using anti-CD31 antibody conjugated to magnetic Dynabeads and/or FACS. ddPCR is performed for the MAP2K1 mutations which may show a mutation that was not able to be identified in the whole tissue because of a lower mutant allelic frequency. If a MAP2K1 mutation is not found, the cells are subjected to WES, WGS, and RNAseq using patient-matched unaffected tissue as control tissue. If a mutation is not identified, then MIPseq of MAP2K1, other genes in the RAS/MAPK signaling pathway, as well as genes associated with conditions that have AVM-like lesions is conducted. A novel HRAS mutation in isolated ECs from WES in a MAP2K1-negative AVM was identified using this strategy (FIGS. 6A-6E).

Example 4: How AVM-Causing Mutations Affect Endothelial Cells and Vasculogenesis The fundamental characteristic of AVM is that a normal capillary bed is absent and thus arteries are abnormally directly connected to veins through either a fistula and/or nidus of abnormal, tortuous vessels. The data show that both the MAP2K1 and HRAS mutations in human AVM specimens is isolated to ECs, providing evidence that this cell is drives the pathophysiology of AVM. It was hypothesized that these mutations in ECs increase downstream ERK phosphorylation which results in abnormal EC function (cell autonomous), and its ability to form normal capillary blood vessels with pericytes (cell non-autonomous). Patient-derived cells as well as genetic and pharmacologic strategies are employed to determine the effect of MAP2K1 mutations on cellular behavior. ECs were isolated from 5 AVM specimens (4 have a MAP2K1 mutation and 1 has an HRAS mutation). Human endothelial colony forming cells (ECFCs) are engineered from umbilical cord blood to express the mutant alleles. ECFCs exhibit a normal endothelial phenotype, proliferate well in vitro, and have vasculogenic potential.

AS/MAPK Signaling in Mutant MAP2K1 Endothelial Cells

Figure 7:
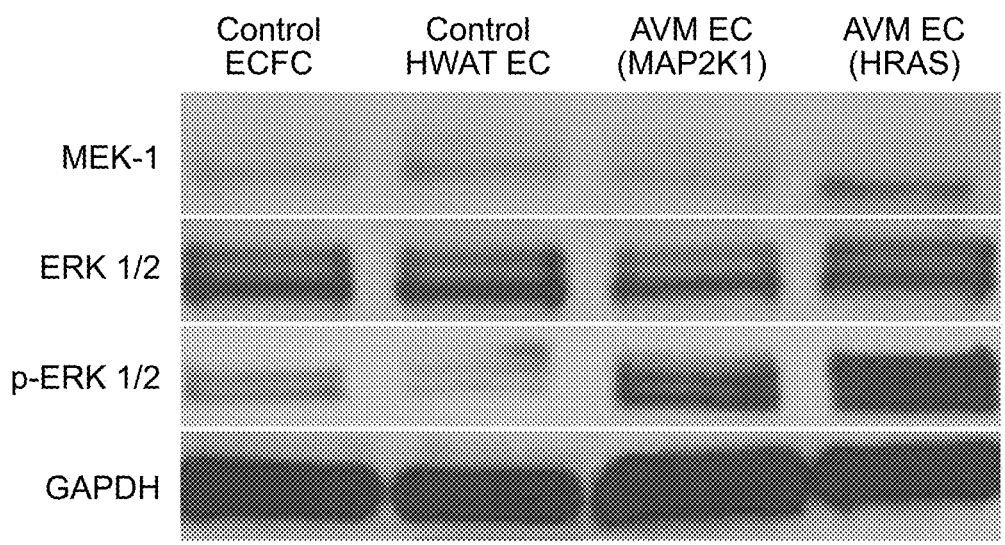
FIG. 7 shows human AVM-derived ECs have activated MEK1 signaling. Western blot showing preliminary data comparing 2 control human ECs (ECFCs and CD31$^+$ HWAT ECs) to ECs isolated from 2 human AVM specimens (one with a MAP2K1 mutation and another with a HRAS mutation). Both mutations stimulate the ERK signaling pathway as shown by increased phosphorylation of ERK. There is 176% and 352% more p-ERK1/2 in MAPK1 and HRAS mutated ECs, respectively, relative to controls (measured by densitometry).
Figure 8:
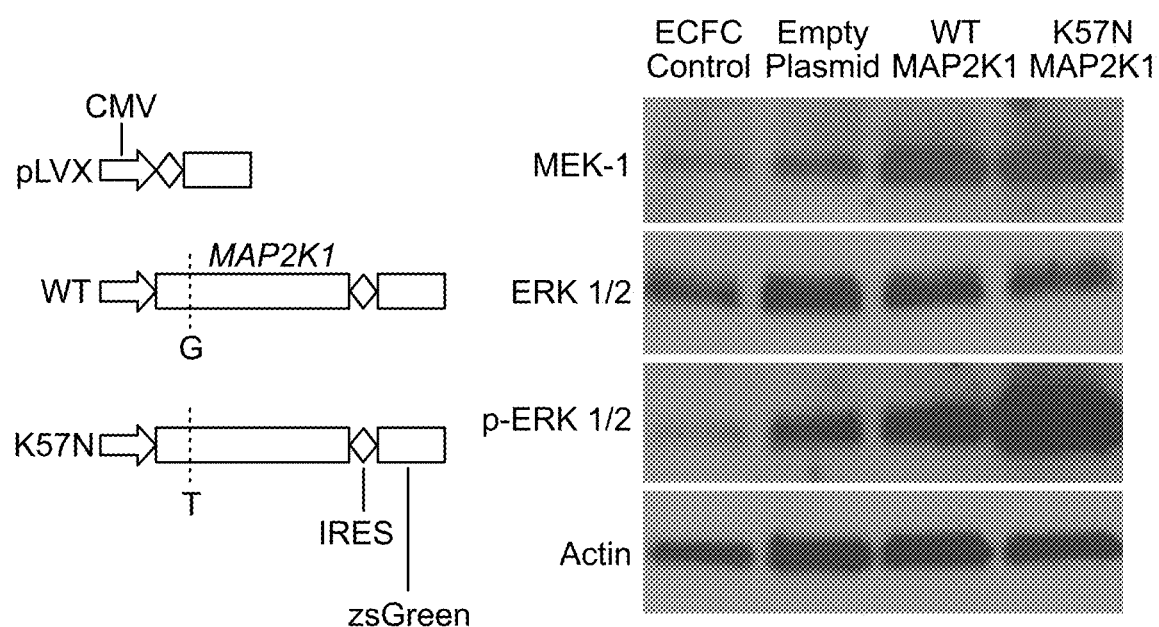
FIG. 8 shows the engineering of wild-type (WT) endothelial cells (ECs). The left panel depicts a schematic of the MEK1 expression plasmids used for transfection of ECFCs. pLVX-zsGreen1 was used as the backbone. The wild-type (WT) and K57N (G to T) mutated MAP2K1 open reading frames were cloned upstream of the IRES-zsGreen1 cassette. Expression of the green fluorescent zsGreen1 protein was used to monitor transfection efficiency. CMV=cytomegalovirus promoter, IRES=internal ribosomal entry site. The right panel is a Western blot analysis of transfected ECFCs. ECFCs were seeded in gelatinized plates and transfected with 1 μg of plasmid using the TransIT-X2 transfection reagent (6/1 TransIT-X2/DNA ratio). Cells then were lysed and 10 μg of protein was separated and transferred to a membrane. Immuno-detection was performed with antibodies against the indicated proteins (1/1000 dilution). Lane 1: non-transfected; Lane 2: transfected with pLVX-zsGr1 (empty vector control); Lane 3: transfected with pLVX-MEK1 WT-zsGr1; Lane 4: transfected with pLVX-MEK1 K57N-zsGr1. ERK phosphorylation is increased 433% by K57N MAP2K1 engineered cells compared to control ECFCs (measured by densitometry).

Because MAP2K1 mutations in other diseases have been shown to be activating, it is predicted that the mutation will constitutively increase phosphorylation of its downstream target ERK1/2. The data herein indicate the mutation is activating in ECs because it increases ERK phosphorylation both in patient-derived AVM ECs, as well as in mutant MAP2K1-engineered ECs (FIGS. 7, 8). Human MAP2K1-AVM ECs and engineered MAP2K1 K57N-ECFCs are compared to control cells: MAP2K1 wild type (WT)-ECFCs, human dermal ECs (HD-ECs), and human white adipose ECs (HWAT-ECs) (both male and female sexes will be included). The MAP2K1 K57N-ECFCs are made using the same methodology that was used to engineer the TIE2 mutation and GNAQ mutation into ECs. Western Blot analysis is conducted using anti-phosphorylated MEK1, MEK2, and ERK1/2 antibodies versus total MEK1, MEK2, ERK1/2 antibodies to determine their phosphorylation. As a complementary approach, mutated cells are treated with the two currently FDA-approved MAP2K1 inhibitors (Trametinib and Cobimetinib) to study whether these agents dampen the predicted hyperactive mutant MEK1.

Angiogenic Behavior of Mutant MAP2K1 Endothelial Cells

Because EC proliferation, migration, and tube formation are required for capillary formation, the function of human MAP2K1-AVM ECs and MAP2K1 K57N-ECFCs is compared to control cells (MAP2K1 WT-ECFCs, HD-ECs, HWAT-ECs) using standard assays. Proliferation is assessed in endothelial growth media (EGM). Migration is measured by serum-starving cells for 16 hours, placing them in the top of a Transwell chamber, and allowing them to migrate to the bottom containing EGM with an endothelial chemoattractant (e.g., VEGF, bFGF) for 6 hours. EC sprouting, branching, and tube formation is evaluated in 3-dimensional fibrin gels. In order to determine if increased or decreased angiogenic behavior results from altered MAP2K1 signaling, MAP2K1 inhibitors (Trametinib and Cobimetinib) are tested on the assays to identify whether they reverse the observed abnormality.

Blood Vessel Formation With Mutant MAP2K1 Endothelial Cells and Pericytes

Capillary formation requires the assembly of ECs and pericytes and their coordinated deposition of basement membrane. Pericytes regulate lumen size and vessel stability. Although the MAP2K1 mutation is exclusively located in ECs, histology shows disrupted and uneven mural cell coverage of vessels in AVM.[3] It was hypothesized that the MAP2K1 mutation in AVM ECs disrupts the hierarchical and regulated assembly of capillaries, veins and arteries, and that EC miscommunication with pericytes is a major contributor to this. Direct and indirect (Transwell) co-culture assays are used to study EC-pericyte interactions. Tests include whether mutant ECs are unable to: (1) direct mesenchymal progenitor cells (MPCs) to pericyte differentiation, (2) recruit pericytes, and/or (3) participate in capillary tube formation. Human AVM MAP2K1 ECs and MAP2K1 K57N-ECFCs are co-cultured separately with MPCs and are compared to control MAP2K1-WT-ECFCs and other control ECs. Differentiation of MPCs into pericytes is assessed using pericyte-specific markers (PDGFRβ and NG2) at the protein and RNA levels. A contractility assay will determine functionality of differentiated pericytes. Inhibitors of MAP2K1 (Trametinib and Cobimetinib) are tested to determine if they reverse the findings. The ability of mutant ECs to recruit normal pericytes and MPCs is determined using a Transwell migration assay. Mutant and control ECs are plated on either side of an 8 μM pore membrane that allows cell migration. Finally, the effects of a MAP2K1 mutation on the ability of ECs and pericytes to form vascular tubes with basement membranes in 3 dimensional in vitro assays is determined using fibrin gels. ECs ($2 \times 10^6$) and pericytes ($4 \times 10^5$) normally form vascular tubes with basement membrane by 3 days. Capillary morphogenesis will be quantified by labelling ECs [anti-CD31, anti-VE-cadherin, Ulex europeus-I (UAE1)], and pericytes (anti-PDGFRβ, NG2), followed by the measurement of lumen formation and branching. We will use inhibitors of MAP2K1 (Trametinib and Cobimetinib) to determine if they normalize EC-pericyte interactions.

RNA sequencing (RNAseq) of Mutant Endothelial Cells in Isolation and in Co-Culture with WT Endothelial Cells and Pericytes.

Figure 9A:
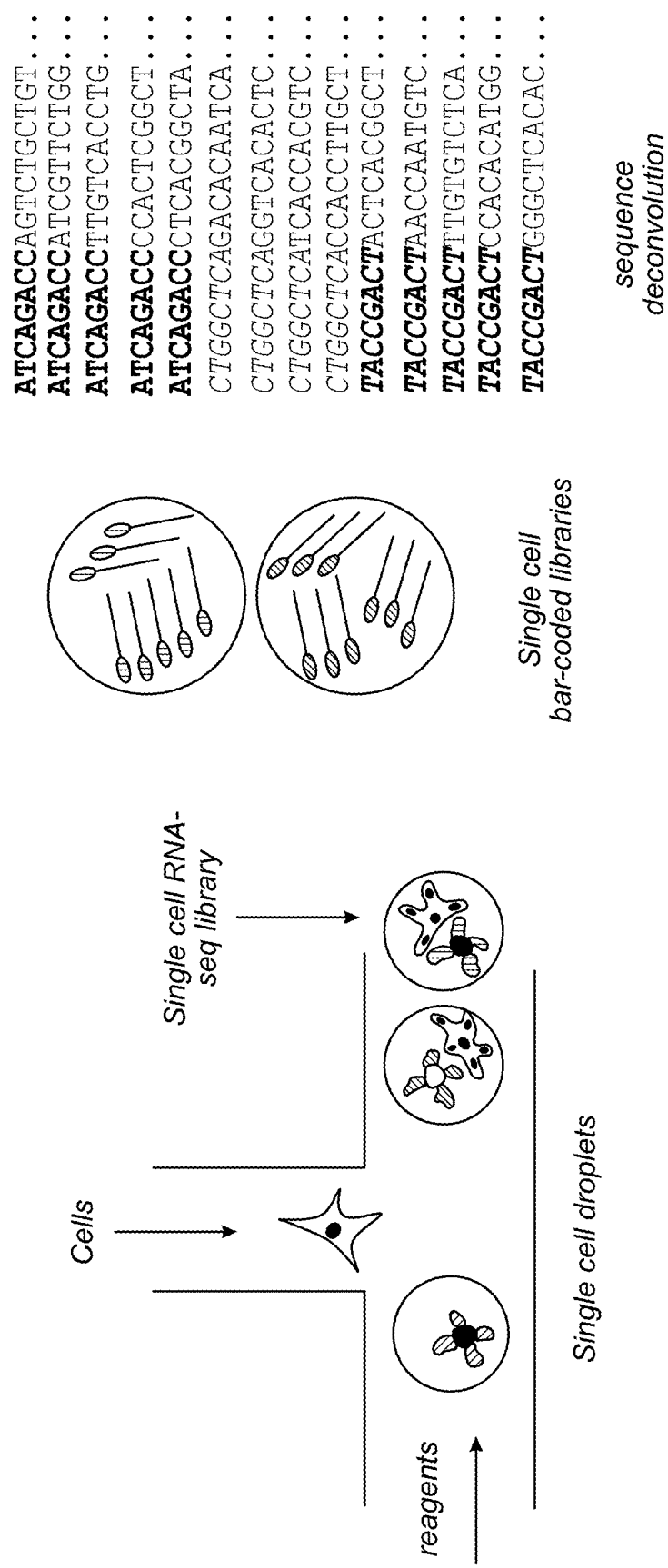
FIGS. 9A-9C show results from single cell RNA sequencing.
Figure 9B:
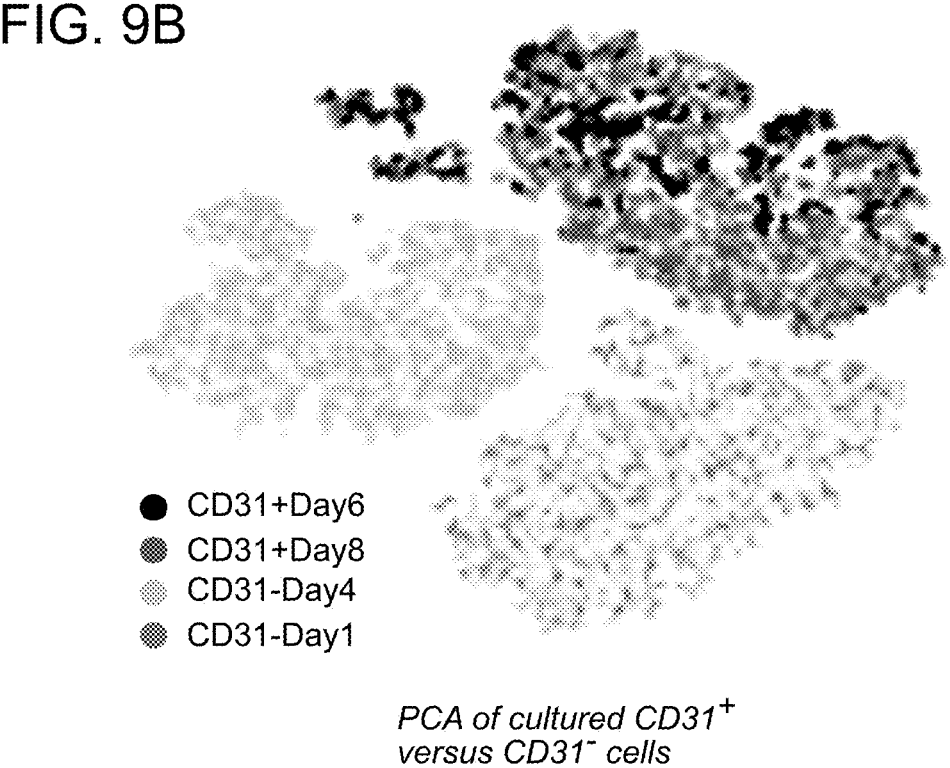
Figure 9C:
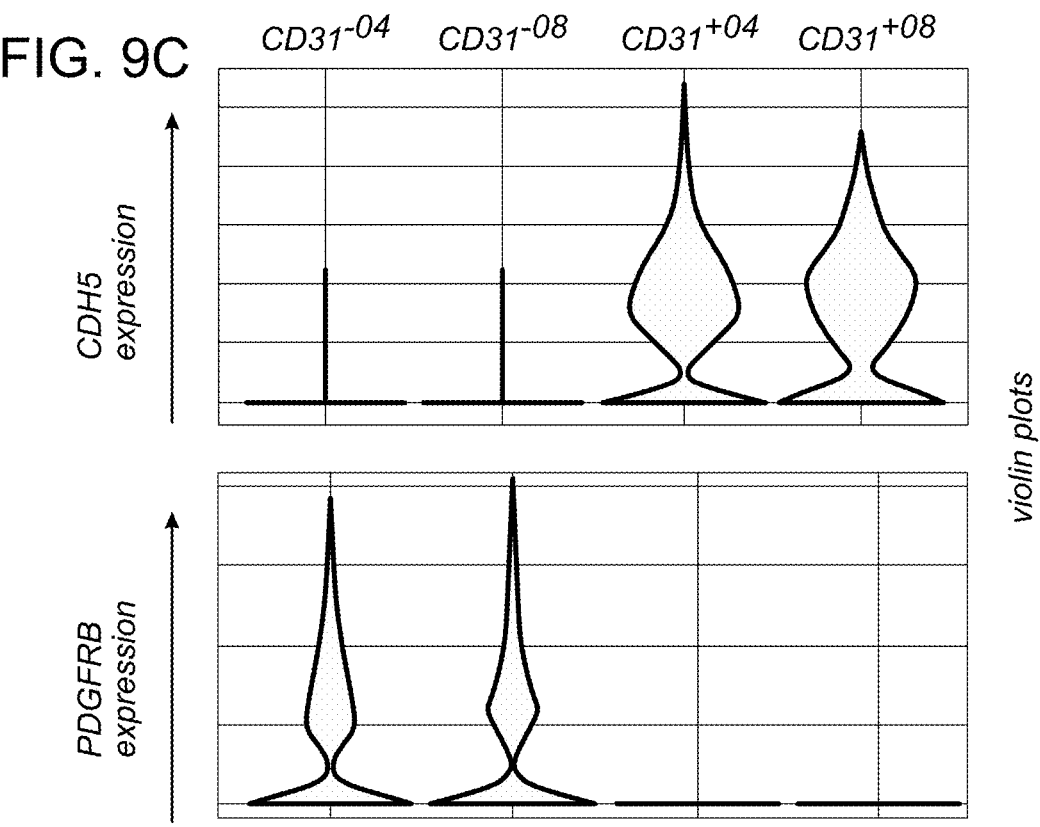

These experiments will help define cell autonomous and cell non-autonomous gene expression changes caused by MAP2K1 mutations. RNAseq is performed on wild-type EC cultures and on cultures of mutant ECs. Cells are harvested and RNAseq libraries are prepared using previously published methods. Bulk RNAseq provide insights regarding how the MAP2K1 mutation affects gene expression in mutant compared to wild-type ECs. Comparing RNAseq data among different patient-derived mutant ECs is informative as to what they share in common. In addition to performing bulk RNAseq, single cell RNAseq is performed to provide data regarding the uniformity of cultured cells with and without MAP2K1 mutations. Single cell RNAseq is conducted to look for cell non-autonomous effects of the MAP2K1 mutations. This is done in two ways. First, co-culturing of wild-type and mutant ECs and use principle components analysis to see whether mutant cells can influence gene expression in wild-type cells, and vice versa. Second, co-culturing ECs with pericytes to determine if mutant ECs affect pericyte gene expression differently than do wild-type ECs. Those genes that exhibit the greatest changes in expression are identified using principle components analysis. Of particular interest are the signaling proteins (secreted or cell membrane proteins) that could be involved in cell-cell signaling during vasculogenesis. Changes in genes for which pharmacologic agents are currently available, also will be of interest for downstream studies. Since mRNA expression need not correlate with protein abundance, transcripts with significant differences in abundance between wild-type and mutant cells are evaluated at the protein level. Immunoblotting and quantitative mass spectroscopy are conducted. Quantitative mass spectroscopy also serves as an orthogonal approach to confirm immunoblotting results. (FIGS. 9A-9C). In a preliminary experiment CD31$^+$ ECs and CD31$^-$ cells were extracted from an AVM sample, placed them into culture, and then performed single cell sequencing. The mutant ECs retained overlapping single cell transcriptomes (as indicated by principle components analysis) even after different passages. Furthermore, single cell transcriptomes from different cell types were readily distinguishable. For example, CD31$^+$ ECs expressed CDH5/VE-Cadherin whereas CD31$^-$ cells expressed the pericyte marker PDGFRβ.

Proteomic Analysis of Mutant MAP2K1 Endothelial Cells

To determine how mutant ECs affect protein synthesis Somascan proteomic assays are used. Conditioned media (100 μl) from human AVM MAP2K1 ECs and MAP2K1-ECFCs, as well as control ECs, are tested for 1310 secreted proteins. SOMAmer reagents are ssDNA-based protein binding reagents. They are chemically modified nucleotides which mimic amino acid side chains, thus enhancing the specificity and affinity of protein-nucleic acid interaction. The most upregulated and downregulated proteins in both human AVM MAP2K1 ECs and MAP2K1 K57N-ECFCs are then confirmed by PCR. Proteins that are significantly elevated or decreased will provide insight into the mechanism by which the MAP2K1 mutation affects AVM pathogenesis. In addition, potential targets may be elucidated for the testing of novel drugs. For example, data with GNAQ-mutant cells showed that ABL serine/threonine kinase was significantly elevated.

Example 5: An Animal Model of AVM

Rationale

An animal model of extracranial AVM does not exist and is needed to study the causal nature of MAP2K1 mutations, the pathophysiology of AVMs, as well as to test pharmacotherapy.

Placement of Human-Derived AVM Cells Into Immunodeficient Mice

To create an animal model of infantile hemangioma with human-derived cells,[24] human AVM-derived ECs are mixed with WT-pericytes at a 2:3 ratio ($2-5 \times 10^6$ cells total), suspended in 200 μl of Matrigel, and injected subcutaneously into the backs of 5-7 week-old athymic nu/nu mice (n=5/group). Human AVM-derived ECs (containing either a MAP2K1 or a HRAS mutation) form more vascularized implants compared to control ECs (FIGS. 10A-10D). Histologically, many vessels are present containing red blood cells in their lumen. These vascular implants are present 7 days following implantation and maintain their phenotype at least up to 21 days. Magnetic resonance (MR) imaging shows that the implants enhance after contrast administration illustrating they are vascularized, and is consistent with the clinical finding that human AVMs enhance with contrast. This animal model is further developed by continuing to collect and implant human AVM ECs. Animals are imaged by MR and Doppler ultrasound 14 days following implantation and the implants are removed and subjected to histological analysis. Sections are stained with hematoxylin and eosin (H&E) to define the morphology of the vessels. Immunohistochemistry is performed with anti CD-31, αSMA, and PDGFRβ antibodies to identify ECs and pericytes. Microvessel as well as pericyte density are calculated and compared to control implants. Microvessel density (vessels/mm$^2$) are measured by counting CD31$^+$ vessel lumens containing red blood cells (10 fields/section) as well as vessel area (10 fields/section) with ImageJ software (FIGS. 11A, 11B).

Placement of Normal Endothelial Cells Engineered with a MAP2K1 Mutation into Immunodeficient Mice In addition to implanting human AVM ECs, an animal model of AVM is created using human ECFCs engineered with MAP2K1-K57N. An animal model of venous malformation is created using ECs engineered to express TIE2, the same mutation that causes human venous malformations. ECFCs were engineered with MAP2K1 (K57N) and shown that the mutation increases ERK phosphorylation. The methods and analysis will be the same as described above for human AVM ECs. Following the establishment of the vascularized implants, the FDA-approved inhibitors of MAP2K1 (Trametinib and Cobimetinib) are tested on the models by 2 methods. First, cells are treated in vitro with the drugs prior to their implantation into mice to determine if the drugs prevent the formation of the vascularized implants. Second, mice are treated with Trametinib and Cobimetinib (intraperitoneal injection) or other MAP2K1 inhibitors that are in Phase II or III studies, immediately after cell placement, as well as after vascular implants have been established, to determine whether they prevent vessel formation or cause vessel regression, respectively.

The data using human AVM ECs shows that vascular implants form from cells with a MAP2K1 K57N mutation (data not shown) or a HRAS mutation (p.Thr58_Ala59delinsValLeuAspVal). AVM ECs from patients with different MAP2K1 mutations are tested to determine if the type of mutation affects the morphology of the implant. Additional studies to investigate the effects of a MAP2K1 mutation on EC behavior would be to back-correct mutant ECs using CRISPR to determine if it returns their phenotype to WT ECs. Other approaches to create an animal model would include: (1) using CRISPR-Cas9 methodology to introduce the MAP2K1 mutation into ECFCs and then implanting these cells into mice, (2) injecting developing limbs with a virus to cause localized increased expression of the mutation, (3) creating a transgenic AVM mouse.

REFERENCES

1. Mulliken J B, Burrows P E, Fishman S J, Mulliken J B. Mulliken and Young's vascular anomalies: hemangiomas and malformations. 2nd ed. Oxford: Oxford University Press; 2013.
2. Liu A S, Mulliken J B, Zurakowski D, Fishman S J, Greene A K. Extracranial arteriovenous malformations: natural progression and recurrence after treatment. Plastic and reconstructive surgery 2010; 125:1185-94.
3. Lin R Z, Moreno-Luna R, Munoz-Hernandez R, et al. Human white adipose tissue vasculature contains endothelial colony-forming cells with robust in vivo vasculogenic potential. Angiogenesis 2013; 16:735-44.
4. Couto J A, Vivero M P, Kozakewich H P, et al. A somatic MAP3K3 mutation is associated with verrucous venous malformation. American journal of human genetics 2015; 96:480-6.
5. Li H, Durbin R. Fast and accurate short read alignment with Burrows-Wheeler transform. Bioinformatics 2009; 25:1754-60.
6. DePristo M A, Banks E, Poplin R, et al. A framework for variation discovery and genotyping using next-generation DNA sequencing data. Nature genetics 2011; 43:491-8.
7. Huang A Y, Xu X, Ye A Y, et al. Postzygotic single-nucleotide mosaicisms in whole-genome sequences of clinically unremarkable individuals. Cell research 2014; 24:1311-27.
8. Sherry S T, Ward M H, Kholodov M, et al. dbSNP: the NCBI database of genetic variation. Nucleic acids research 2001; 29:308-11.
9. Genomes Project C, Abecasis G R, Auton A, et al. An integrated map of genetic variation from 1,092 human genomes. Nature 2012; 491:56-65.
10. Tennessen J A, Bigham A W, O'Connor T D, et al. Evolution and functional impact of rare coding variation from deep sequencing of human exomes. Science 2012; 337:64-9.
11. Lek M, Karczewski K J, Minikel E V, et al. Analysis of protein-coding genetic variation in 60,706 humans. Nature 2016; 536:285-91.
12. Adzhubei I A, Schmidt S, Peshkin L, et al. A method and server for predicting damaging missense mutations. Nature methods 2010; 7:248-9.
13. Kumar P, Henikoff S, Ng P C. Predicting the effects of coding non-synonymous variants on protein function using the SIFT algorithm. Nature protocols 2009; 4:1073-81.
14. Luks V L, Kamitaki N, Vivero M P, et al. Lymphatic and other vascular malformative/overgrowth disorders are caused by somatic mutations in PIK3CA. The Journal of pediatrics 2015; 166:1048-54 el-5.
15. Greene A K, Liu A S, Mulliken J B, Chalache K, Fishman S J. Vascular anomalies in 5,621 patients: guidelines for referral. Journal of pediatric surgery 2011; 46:1784-9.
16. Happle R. Lethal genes surviving by mosaicism: a possible explanation for sporadic birth defects involving the skin. Journal of the American Academy of Dermatology 1987; 16:899-906.
17. Kohout M P, Hansen M, Pribaz J J, Mulliken J B. Arteriovenous malformations of the head and neck: natural history and management. Plastic and reconstructive surgery 1998; 102: 643-54.
18. McDonald J, Pyeritz R E. Hereditary Hemorrhagic Telangiectasia. In: Pagon R A, Adam M P, Ardinger H H, et al., eds. GeneReviews®. Seattle (Wash.) 1993.
19. Bayrak-Toydemir P, Stevenson D. RASA1-Related Disorders. In: Pagon R A, Adam MP, Ardinger H H, et al., eds. GeneReviews®. Seattle (Wash.) 1993.
20. Eng C. PTEN Hamartoma Tumor Syndrome. In: Pagon R A, Adam M P, Ardinger H H, et al., eds. GeneReviews®. Seattle (Wash.) 1993.
21. Caunt C J, Sale M J, Smith P D, Cook S J. MEK1 and MEK2 inhibitors and cancer therapy: the long and winding road. Nature reviews Cancer 2015; 15:577-92.
22. Wortzel I, Seger R. The ERK Cascade: Distinct Functions within Various Subcellular Organelles. Genes & cancer 2011; 2:195-209.
23. Arcila M E, Drilon A, Sylvester B E, et al. MAP2K1 (MEK1) Mutations Define a Distinct Subset of Lung Adenocarcinoma Associated with Smoking. Clinical cancer research: an official journal of the American Association for Cancer Research 2015; 21:1935-43.
24. Bansal A, Ramirez R D, Minna J D. Mutation analysis of the coding sequences of MEK-1 and MEK-2 genes in human lung cancer cell lines. Oncogene 1997; 14:1231-4.
25. Chakraborty R, Hampton O A, Shen X, et al. Mutually exclusive recurrent somatic mutations in MAP2K1 and BRAF support a central role for ERK activation in LCH pathogenesis. Blood 2014; 124:3007-15.
26. Choi Y L, Soda M, Ueno T, et al. Oncogenic MAP2K1 mutations in human epithelial tumors. Carcinogenesis 2012; 33:956-61.
27. Estep A L, Palmer C, McCormick F, Rauen K A. Mutation analysis of BRAF, MEK1 and MEK2 in 15 ovarian cancer cell lines: implications for therapy. PloS one 2007; 2:e1279.
28. Nikolaev S I, Rimoldi D, Iseli C, et al. Exome sequencing identifies recurrent somatic MAP2K1 and MAP2K2 mutations in melanoma. Nature genetics 2012; 44:133-9.
29. Mansour S J, Matten W T, Hermann A S, et al. Transformation of mammalian cells by constitutively active MAP kinase kinase. Science 1994; 265:966-70.
30. Marks J L, Gong Y, Chitale D, et al. Novel MEK1 mutation identified by mutational analysis of epidermal growth factor receptor signaling pathway genes in lung adenocarcinoma. Cancer research 2008; 68:5524-8.

31. Sherry S T, Ward M, Sirotkin K. Use of molecular variation in the NCBI dbSNP database. Human mutation 2000; 15:68-75.
32. Aoki Y, Matsubara Y. Ras/MAPK syndromes and childhood hemato-oncological diseases. International journal of hematology 2013; 97:30-6.
33. Knight T, Irving J A. Ras/Raf/MEK/ERK Pathway Activation in Childhood Acute Lymphoblastic Leukemia and Its Therapeutic Targeting. Frontiers in oncology 2014; 4:160.
34. Lim Y H, Bacchiocchi A, Qiu J, et al. GNA14 Somatic Mutation Causes Congenital and Sporadic Vascular Tumors by MAPK Activation. American journal of human genetics 2016; 99:443-50.
35. Lim Y H, Douglas S R, Ko C J, et al. Somatic Activating RAS Mutations Cause Vascular Tumors Including Pyogenic Granuloma. The Journal of investigative dermatology 2015; 135:1698-700.
36. Solus J F, Kraft S. Ras, Raf, and MAP kinase in melanoma. Advances in anatomic pathology 2013; 20:217-26.
37. Zenker M. Clinical manifestations of mutations in RAS and related intracellular signal transduction factors. Current opinion in pediatrics 2011; 23:443-51.
38. Giroux S, Tremblay M, Bernard D, et al. Embryonic death of Mek1-deficient mice reveals a role for this kinase in angiogenesis in the labyrinthine region of the placenta. Current biology: CB 1999; 9:369-72.
39. Nava C, Hanna N, Michot C, et al. Cardio-facio-cutaneous and Noonan syndromes due to mutations in the RAS/MAPK signalling pathway: genotype-phenotype relationships and overlap with Costello syndrome. Journal of medical genetics 2007; 44:763-71.
40. Rodriguez-Viciana P, Tetsu O, Tidyman W E, et al. Germline mutations in genes within the MAPK pathway cause cardio-facio-cutaneous syndrome. Science 2006; 311:1287-90.
41. Allanson J E, Roberts A E. Noonan Syndrome. In: Pagon R A, Adam M P, Ardinger H H, et al., eds. GeneReviews®. Seattle (Wash.) 1993.
42. Rauen K A. Cardiofaciocutaneous Syndrome. In: Pagon R A, Adam M P, Ardinger H H, et al., eds. GeneReviews®. Seattle (Wash.) 1993.
43. Greene A K, Orbach D B. Management of arteriovenous malformations. Clinics in plastic surgery 2011; 38:95-106.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating or preventing arteriovenous malformation (AVM) in a subject, the method comprising:
   (a) identifying a subject having or at risk of AVM; and
   (b) administering a MEK1 inhibitor to the subject,
thereby treating or preventing AVM in the subject, wherein the MEK1 inhibitor is N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H)-yl}phenyl)acetamide (Trametinib), and
wherein administering is oral administration.

2. The method of claim 1, wherein the AVM comprises a somatic MAP2K1 mutation that upregulates MEK1 levels and/or in one or more genes associated with a RAS/MAPK pathway.

3. The method of claim 2, wherein the somatic MAP2K1 mutation comprising: Lys57Asn, Gln56Pro, Gln58_Glu62del, Phe53Leu/Asp67Tyr, or combinations thereof.

4. The method of claim 3, wherein the somatic MAP2K1 mutations comprise p.F53L and p.D67Y in cis.

5. The method of claim 1, wherein the AVM is a solitary extracranial AVM selected from the group consisting of a facial AVM, a scalp AVM, an ear AVM, an upper lip AVM and an abdominal AVM.

6. The method of claim 1 wherein the AVM is a Stage I, Stage II or Stage III AVM.

7. The method of claim 1, wherein the subject is a human.

8. The method of claim 1, wherein the AVM location is recited in Table 2.

9. The method of claim 1, further comprising administering an effective amount of one or more anti-angiogenic agents.

10. The method of claim 9, wherein the anti-angiogenic agent comprises
sunitinib, angiostatin K1-3, arresten, DL-a-difluoromethyl-ornithine, fumagillin, genistein, staurosporine, (±)-thalidomide, tumstatin, axitinib, bortezomib, bosutinib gefitinib, pazopanib, semaxanib, sorafenib, vandetanib, vatalanib, canertinib, cilengitide, dovitinib, dasatinib, erlotinib, everolimus, imatinib, lapatinib, masutinib, marizomib, mubitinib, lestaurtinib, pazopanib, tandutinib, vismodegib or combinations thereof.

11. The method of claim 1, further comprising administering an effective amount of one or more inhibitors of ERK1/2 comprising SCH772984, LY3214996, SC1, RasGAP, VX-11e, DEL-22379, Ulixertinib (BVD-523, VRT752271), GDC-0994, FR 180204, ERK5-IN-1, or combinations thereof.

12. The method of claim 2, wherein the one or more genes associated with the RAS/MAPK pathway, comprise: HRAS, KRAS, NRAS, ARAF, BRAF, RAF1, MAP2K2, MAPK1, MAPK3, MAP3K3, or combinations thereof.

13. The method of claim 12, wherein a mutation in HRAS is p.Thr58_Ala59delinsValLeuAspVal.

* * * * *

UNITED STATES PATENT AND TRADEMARK OFFICE
CERTIFICATE OF CORRECTION

| | |
|---|---|
| PATENT NO. | : 11,104,955 B2 |
| APPLICATION NO. | : 16/474976 |
| DATED | : August 31, 2021 |
| INVENTOR(S) | : Arin K. Greene, Matthew Warman and Yue Huang |

It is certified that error appears in the above-identified patent and that said Letters Patent is hereby corrected as shown below:

In the Specification

At Column 1, Lines 18-21:
"This invention was made with government support under Grant nos. HD082606, HD081004 and AR064231, awarded by The National Institutes of Health. The government has certain rights in the invention."
Should be replaced with:
-- This invention was made with government support under Grant Numbers HD082606, HD081004, HD093735, and AR064231, awarded by the National Institutes of Health. The government has certain rights in the invention. --

Signed and Sealed this
Thirteenth Day of December, 2022

Katherine Kelly Vidal
*Director of the United States Patent and Trademark Office*

SEQUENCE LISTING

```
<160> NUMBER OF SEQ ID NOS: 21

<210> SEQ ID NO 1
<211> LENGTH: 2603
<212> TYPE: DNA
<213> ORGANISM: Homo sapiens

<400> SEQUENCE: 1
aggcgaggct tcccttccc cgcccctccc ccggcctcca gtccctccca gggccgcttc      60
gcagagcggc taggagcacg gcggcggcgg cactttcccc ggcaggagct ggagctgggc     120
tctggtgcgc gcgcggctgt gccgcccgag ccggagggac tggttggttg agagagagag     180
aggaagggaa tcccgggctg ccgaaccgca cgttcagccc gctccgctcc tgcagggcag     240
cctttcggct ctctgcgcgc gaagccgagt cccggcggg tggggcgggg gtccactgag     300
accgctaccg gcccctcggc gctgacggga ccgcgcgggg cgcaccgct gaaggcagcc      360 ccggggccg cggcccggac ttggtcctgc gcagcgggc cggggcagcg cagcgggagg       420
aagcgagagg tgctgccctc ccccggagt tggaagcgcg ttacccgggt ccaaaatgcc      480
caagaagaag ccgacgccca tccagctgaa cccgccccc gacggctctg cagttaacgg     540
gaccagctct gcggagacca acttggaggc cttgcagaag aagctggagg agctagagct     600
tgatgagcag cagcgaaagc gccttgaggc ctttcttacc cagaagcaga aggtgggaga     660
actgaaggat gacgactttg agaagatcag tgagctgggg gctggcaatg gcggtgtggt     720
gttcaaggtc tcccacaagc cttctggcct ggtcatggcc agaaagctaa ttcatctgga     780
gatcaaaccc gcaatccgga accagatcat aagggagctg caggttctgc atgagtgcaa     840
ctctccgtac atcgtgggct tctatggtgc gttctacagc gatggcgaga tcagtatctg     900
catggagcac atggatggag gttctctgga tcaagtcctg aagaaagctg gaagaattcc     960
tgaacaaatt ttaggaaaag ttagcattgc tgtaataaaa ggcctgacat atctgaggga    1020
```

-continued

```
gaagcacaag atcatgcaca gagatgtcaa gccctccaac atcctagtca actcccgtgg    1080
ggagatcaag ctctgtgact ttggggtcag cgggcagctc atcgactcca tggccaactc    1140
cttcgtgggc acaaggtcct acatgtcgcc agaaagactc caggggactc attactctgt    1200
gcagtcagac atctggagca tgggactgtc tctggtagag atggcggttg ggaggtatcc    1260
catccctcct ccagatgcca aggagctgga gctgatgttt gggtgccagg tggaaggaga    1320
tgcggctgag accccaccca ggccaaggac ccccggagg cccttagct catacggaat      1380 ggacagccga cctcccatgg caattttga gttgttggat tacatagtca acgagcctcc     1440
tccaaaactg cccagtggag tgttcagtct ggaatttcaa gattttgtga ataaatgctt    1500
aataaaaaac cccgcagaga gagcagattt gaagcaactc atggttcatg cttttatcaa    1560
gagatctgat gctgaggaag tggattttgc aggttggctc tgctccacca tcggccttaa    1620
ccagcccagc acaccaaccc atgctgctgg cgtctaagtg tttgggaagc aacaaagagc    1680
gagtcccctg cccggtggtt tgccatgtcg cttttgggcc tccttcccat gcctgtctct    1740
gttcagatgt gcatttcacc tgtgacaaag gatgaagaac acagcatgtg ccaagattct    1800
actcttgtca tttttaatat tactgtcttt attcttatta ctattattgt tcccctaagt    1860
ggattggctt tgtgcttggg ctatttgtg tgtatgctga tgatcaaaac ctgtgccagg     1920
ctgaattaca gtgaaatttt ggtgaatgtg ggtagtcatt cttacaattg cactgctgtt    1980
cctgctccat gactggctgt ctgcctgtat tttcgggatt ctttgacatt tggtggtact    2040
ttattcttgc tgggcatact ttctctctag gagggagcct tgtgagatcc ttcacaggca    2100
gtgcatgtga agcatgcttt gctgctatga aaatgagcat cagagagtgt acatcatgtt    2160
attttattat tattatttgc ttttcatgta gaactcagca gttgacatcc aaatctagcc    2220
agagcccttc actgccatga tagctggggc ttcaccagtc tgtctactgt ggtgatctgt    2280
agacttctgg ttgtatttct atatttattt tcagtatact gtgtgggata cttagtggta    2340
tgtctcttta agttttgatt aatgtttctt aaatggaatt attttgaatg tcacaaattg    2400
atcaagatat taaaatgtcg gatttatctt tccccatatc caagtaccaa tgctgttgta    2460
aacaacgtgt atagtgccta aaattgtatg aaaatccttt taaccatttt aacctagatg    2520
tttaacaaat ctaatctctt attctaataa atatactatg aaataaaaaa aaaaggatga    2580
aagctaaaaa aaaaaaaaaa aaa                                           2603
```

<210> SEQ ID NO 2
<211> LENGTH: 393
<212> TYPE: PRT
<213> ORGANISM: Homo sapiens

<400> SEQUENCE: 2

```
Met Pro Lys Lys Lys Pro Thr Pro Ile Gln Leu Asn Pro Ala Pro Asp
1               5                   10                  15

Gly Ser Ala Val Asn Gly Thr Ser Ser Ala Glu Thr Asn Leu Glu Ala
            20                  25                  30

Leu Gln Lys Lys Leu Glu Glu Leu Glu Leu Asp Glu Gln Gln Arg Lys
        35                  40                  45

Arg Leu Glu Ala Phe Leu Thr Gln Lys Gln Lys Val Gly Glu Leu Lys
    50                  55                  60

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Val Met Ala Arg
                85                  90                  95
```

```
Lys Leu Ile His Leu Glu Ile Lys Pro Ala Ile Arg Asn Gln Ile Ile
            100                 105                 110

Arg Glu Leu Gln Val Leu His Glu Cys Asn Ser Pro Tyr Ile Val Gly
            115                 120                 125

Phe Tyr Gly Ala Phe Tyr Ser Asp Gly Glu Ile Ser Ile Cys Met Glu
    130                 135                 140

His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
                165                 170                 175

Leu Thr Tyr Leu Arg Glu Lys His Lys Ile Met His Arg Asp Val Lys
        180                 185                 190

Pro Ser Asn Ile Leu Val Asn Ser Arg Gly Glu Ile Lys Leu Cys Asp
        195                 200                 205

Phe Gly Val Ser Gly Gln Leu Ile Asp Ser Met Ala Asn Ser Phe Val
    210                 215                 220

Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
                245                 250                 255

Ala Val Gly Arg Tyr Pro Ile Pro Pro Asp Ala Lys Glu Leu Glu
        260                 265                 270

Leu Met Phe Gly Cys Gln Val Glu Gly Asp Ala Ala Glu Thr Pro Pro
        275                 280                 285

Arg Pro Arg Thr Pro Gly Arg Pro Leu Ser Ser Tyr Gly Met Asp Ser
    290                 295                 300

Arg Pro Pro Met Ala Ile Phe Glu Leu Leu Asp Tyr Ile Val Asn Glu
305                 310                 315                 320

Pro Pro Pro Lys Leu Pro Ser Gly Val Phe Ser Leu Glu Phe Gln Asp
                325                 330                 335

Phe Val Asn Lys Cys Leu Ile Lys Asn Pro Ala Glu Arg Ala Asp Leu
        340                 345                 350

Lys Gln Leu Met Val His Ala Phe Ile Lys Arg Ser Asp Ala Glu Glu
        355                 360                 365

Val Asp Phe Ala Gly Trp Leu Cys Ser Thr Ile Gly Leu Asn Gln Pro
370                 375                 380

Ser Thr Pro Thr His Ala Ala Gly Val
385                 390

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Leu Asp Val
1

<210> SEQ ID NO 4
<211> LENGTH: 11
<212> TYPE: DNA
<213> ORGANISM: Homo sapiens

<400> SEQUENCE: 4
```

```
tacccagaag c                                                        11

<210> SEQ ID NO 5
<211> LENGTH: 43
<212> TYPE: DNA
<213> ORGANISM: Homo sapiens

<400> SEQUENCE: 5
ttcttaccca gaagcagaag gtgggagaac tgaaggatga cga                     43

<210> SEQ ID NO 6
<211> LENGTH: 11
<212> TYPE: DNA
<213> ORGANISM: Homo sapiens

<400> SEQUENCE: 6
cagaagcaga a                                                        11

<210> SEQ ID NO 7
<211> LENGTH: 43
<212> TYPE: DNA
<213> ORGANISM: Homo sapiens

<400> SEQUENCE: 7
ttcttaccca gaagcagaag gtgggagaac tgaaggatga cga                     43

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
atcagaccag tctgctgt                                                 18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
atcagaccat cgttctgg                                                 18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
atcagacctt gtcacctg                                                 18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 11
atcagacccc actcggct                                                     18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
atcagaccct cacggcta                                                     18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ctggctcaga cacaatca                                                     18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ctggctcagg tcacactc                                                     18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ctggctcatc accacgtc                                                     18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ctggctcacc accttgct                                                     18

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 17
taccgactac tcacggct                                              18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
taccgactaa ccaatgtc                                              18

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
taccgacttt gtgtctca                                              18

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
taccgactcc acacatgg                                              18

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
taccgactgg gctcacac                                              18
```